United States Patent
Heit et al.

(10) Patent No.: US 12,280,256 B2
(45) Date of Patent: *Apr. 22, 2025

(54) METHODS AND SYSTEMS FOR DISEASE TREATMENT USING ELECTRICAL STIMULATION

(71) Applicant: Nevro Corp., Redwood City, CA (US)

(72) Inventors: Gary Heit, Woodside, CA (US); Bradford Evan Gliner, Sammamish, WA (US)

(73) Assignee: Nevro Corp., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/622,434

(22) Filed: Mar. 29, 2024

(65) Prior Publication Data

US 2024/0238593 A1 Jul. 18, 2024

Related U.S. Application Data

(63) Continuation of application No. 16/922,304, filed on Jul. 7, 2020, now Pat. No. 11,998,744, which is a continuation of application No. 15/870,052, filed on Jan. 12, 2018, now Pat. No. 10,751,536, which is a continuation of application No. 14/300,193, filed on Jun. 9, 2014, now Pat. No. 9,895,539.

(60) Provisional application No. 61/833,392, filed on Jun. 10, 2013.

(51) Int. Cl.
*A61N 1/36* (2006.01)

(52) U.S. Cl.
CPC ..... *A61N 1/36071* (2013.01); *A61N 1/36062* (2017.08); *A61N 1/36157* (2013.01); *A61N 1/36171* (2013.01); *A61N 1/36175* (2013.01)

(58) Field of Classification Search
CPC ............ A61N 1/36071; A61N 1/36062; A61N 1/36157; A61N 1/36171; A61N 1/36175
See application file for complete search history.

(56) References Cited

U.S. PATENT DOCUMENTS

| | | |
|---|---|---|
| 1,597,061 A | 8/1926 | Cultra |
| 3,195,540 A | 7/1965 | Waller |
| 3,724,467 A | 4/1973 | Avery et al. |
| 3,727,616 A | 4/1973 | Lenzkes |
| 3,817,254 A | 6/1974 | Maurer |

(Continued)

FOREIGN PATENT DOCUMENTS

| | | |
|---|---|---|
| AU | 2017221321 | 4/2021 |
| CN | 101175530 | 5/2008 |

(Continued)

OTHER PUBLICATIONS

U.S. Appl. No. 14/534,769, filed Nov. 6, 2014, Park.

(Continued)

*Primary Examiner* — Joseph M Dietrich
(74) *Attorney, Agent, or Firm* — Perkins Coie LLP

(57) ABSTRACT

Systems for disease treatment using electrical stimulation are disclosed. A representative method for treating a patient includes changing an activity, expression, or both activity and expression of a fast sodium channel, a glial cell, or both a fast sodium channel and a glial cell of the patient by applying to a target neural population of the patient an electrical therapy signal having a frequency in a frequency range of 1.5 kHz to 100 KHz.

30 Claims, 1 Drawing Sheet

(56) References Cited

U.S. PATENT DOCUMENTS

| | | |
|---|---|---|
| 3,822,708 A | 7/1974 | Zilber |
| 3,893,463 A | 7/1975 | Williams |
| 4,014,347 A | 3/1977 | Halleck et al. |
| 4,023,574 A | 5/1977 | Nemec |
| 4,055,190 A | 10/1977 | Tany et al. |
| 4,148,321 A | 4/1979 | Wyss et al. |
| 4,379,462 A | 4/1983 | Borkan et al. |
| 4,414,986 A | 11/1983 | Dickhudt et al. |
| 4,535,777 A | 8/1985 | Castel |
| 4,541,432 A | 9/1985 | Molina-Negro et al. |
| 4,608,985 A | 9/1986 | Crish et al. |
| 4,612,934 A | 9/1986 | Borkan et al. |
| 4,649,935 A | 3/1987 | Charmillot et al. |
| 4,735,204 A | 4/1988 | Sussman et al. |
| 4,764,132 A | 8/1988 | Stutz, Jr. |
| 4,793,353 A | 12/1988 | Borkan et al. |
| 4,841,973 A | 6/1989 | Stecker |
| RE33,420 E | 11/1990 | Sussman et al. |
| 5,002,053 A | 3/1991 | Garcia-Rill |
| 5,335,657 A | 8/1994 | Terry, Jr. et al. |
| 5,354,320 A | 10/1994 | Schaldach et al. |
| 5,514,175 A | 5/1996 | Kim et al. |
| 5,540,734 A | 7/1996 | Zabara |
| 5,562,717 A | 10/1996 | Tippey et al. |
| 5,643,330 A | 7/1997 | Holsheimer et al. |
| 5,716,377 A | 2/1998 | Rise et al. |
| 5,755,758 A | 5/1998 | Wolozko |
| 5,776,170 A | 7/1998 | MacDonald et al. |
| 5,830,151 A | 11/1998 | Hadzic et al. |
| 5,853,373 A | 12/1998 | Griffith et al. |
| 5,893,883 A | 4/1999 | Torgerson et al. |
| 5,938,690 A | 8/1999 | Law |
| 5,983,141 A | 11/1999 | Sluijter et al. |
| 5,995,872 A | 11/1999 | Bourgeois |
| 6,002,964 A | 12/1999 | Feler et al. |
| 6,014,588 A | 1/2000 | Fitz |
| 6,027,456 A | 2/2000 | Feler et al. |
| 6,049,701 A | 4/2000 | Sparksman |
| 6,161,044 A | 12/2000 | Silverstone |
| 6,161,048 A | 12/2000 | Sluijter et al. |
| 6,167,311 A | 12/2000 | Rezai |
| 6,176,242 B1 | 1/2001 | Rise |
| 6,233,488 B1 | 5/2001 | Hess |
| 6,236,892 B1 | 5/2001 | Feler et al. |
| 6,238,423 B1 | 5/2001 | Bardy |
| 6,246,912 B1 | 6/2001 | Sluijter et al. |
| 6,319,241 B1 | 11/2001 | King et al. |
| 6,341,236 B1 | 1/2002 | Osorio et al. |
| 6,356,786 B1 | 3/2002 | Rezai et al. |
| 6,366,814 B1 | 4/2002 | Boveja |
| 6,393,325 B1 | 5/2002 | Mann et al. |
| 6,397,108 B1 | 5/2002 | Camps et al. |
| 6,405,079 B1 | 6/2002 | Ansarinia |
| 6,421,566 B1 | 7/2002 | Holsheimer |
| 6,440,090 B1 | 8/2002 | Schallhorn |
| 6,473,644 B1 | 10/2002 | Terry, Jr. et al. |
| 6,505,078 B1 | 1/2003 | King et al. |
| 6,510,347 B2 | 1/2003 | Borkan |
| 6,516,227 B1 | 2/2003 | Meadows et al. |
| 6,526,318 B1 | 2/2003 | Ansarinia |
| 6,571,127 B1 | 5/2003 | Ben-Haim et al. |
| 6,584,358 B2 | 6/2003 | Carter et al. |
| 6,587,724 B2 | 7/2003 | Mann |
| 6,609,030 B1 | 8/2003 | Rezai et al. |
| 6,622,048 B1 | 9/2003 | Mann et al. |
| 6,659,968 B1 | 12/2003 | McClure |
| 6,662,051 B1 | 12/2003 | Eraker et al. |
| 6,714,822 B2 | 3/2004 | King et al. |
| 6,721,603 B2 | 4/2004 | Zabara et al. |
| 6,795,737 B2 | 9/2004 | Gielen et al. |
| 6,856,315 B2 | 2/2005 | Eberlein |
| 6,862,479 B1 | 3/2005 | Whitehurst |
| 6,871,090 B1 | 3/2005 | He et al. |
| 6,871,099 B1 | 3/2005 | Whitehurst et al. |
| 6,885,888 B2 | 4/2005 | Rezai |
| 6,892,097 B2 | 5/2005 | Holsheimer et al. |
| 6,907,293 B2 | 6/2005 | Grill et al. |
| 6,907,295 B2 | 6/2005 | Gross et al. |
| 6,923,784 B2 | 8/2005 | Stein |
| 6,928,230 B2 | 8/2005 | Squibbs |
| 6,928,320 B2 | 8/2005 | King |
| 6,950,707 B2 | 9/2005 | Whitehurst |
| 6,959,215 B2 | 10/2005 | Gliner |
| 6,968,237 B2 | 11/2005 | Doan et al. |
| 6,990,376 B2 | 1/2006 | Tanagho et al. |
| 7,024,246 B2 | 4/2006 | Acosta et al. |
| 7,047,079 B2 | 5/2006 | Erickson |
| 7,054,686 B2 | 5/2006 | MacDonald |
| 7,082,333 B1 | 7/2006 | Bauhahn et al. |
| 7,117,034 B2 | 10/2006 | Kronberg |
| 7,146,224 B2 | 12/2006 | King |
| 7,149,574 B2 | 12/2006 | Yun et al. |
| 7,162,304 B1 | 1/2007 | Bradley |
| 7,167,750 B2 | 1/2007 | Knudson et al. |
| 7,174,215 B2 | 2/2007 | Bradley |
| 7,177,702 B2 | 2/2007 | Wallace et al. |
| 7,180,760 B2 | 2/2007 | Varrichio et al. |
| 7,206,640 B1 | 4/2007 | Overstreet |
| 7,212,865 B2 | 5/2007 | Cory |
| 7,225,035 B2 | 5/2007 | Brabec et al. |
| 7,236,822 B2 | 6/2007 | Dobak, III |
| 7,236,830 B2 | 6/2007 | Gliner |
| 7,239,912 B2 | 7/2007 | Dobak, III |
| 7,252,090 B2 | 8/2007 | Goetz |
| 7,260,436 B2 | 8/2007 | Kilgore et al. |
| 7,266,412 B2 | 9/2007 | Stypulkowski |
| 7,288,062 B2 | 10/2007 | Spiegel |
| 7,313,440 B2 | 12/2007 | Miesel |
| 7,324,852 B2 | 1/2008 | Barolat et al. |
| 7,326,181 B2 | 2/2008 | Katims |
| 7,333,857 B2 | 2/2008 | Campbell |
| 7,337,005 B2 | 2/2008 | Kim et al. |
| 7,346,398 B2 | 3/2008 | Gross et al. |
| 7,349,743 B2 | 3/2008 | Tadlock |
| RE40,279 E | 4/2008 | Sluijter et al. |
| 7,359,751 B1 | 4/2008 | Erickson et al. |
| 7,363,076 B2 | 4/2008 | Yun et al. |
| 7,389,145 B2 | 6/2008 | Kilgore et al. |
| 7,393,351 B2 | 7/2008 | Woloszko et al. |
| 7,463,927 B1 | 12/2008 | Chaouat |
| 7,483,747 B2 | 1/2009 | Gliner et al. |
| 7,493,172 B2 | 2/2009 | Whitehurst et al. |
| 7,502,652 B2 | 3/2009 | Gaunt et al. |
| 7,571,007 B2 | 8/2009 | Erickson et al. |
| 7,580,753 B2 | 8/2009 | Kim et al. |
| 7,599,737 B2 | 10/2009 | Yomtov et al. |
| 7,634,317 B2 | 12/2009 | Ben-David et al. |
| 7,676,269 B2 | 3/2010 | Yun et al. |
| 7,689,276 B2 | 3/2010 | Dobak |
| 7,689,289 B2 | 3/2010 | King |
| 7,715,915 B1 | 5/2010 | Rye et al. |
| 7,734,340 B2 | 6/2010 | De Ridder |
| 7,734,355 B2 | 6/2010 | Cohen et al. |
| 7,742,810 B2 | 6/2010 | Moffitt et al. |
| 7,761,170 B2 | 7/2010 | Kaplan et al. |
| 7,778,704 B2 | 8/2010 | Rezai |
| 7,792,591 B2 | 9/2010 | Rooney et al. |
| 7,801,604 B2 | 9/2010 | Brockway et al. |
| 7,813,803 B2 | 10/2010 | Heruth et al. |
| 7,826,901 B2 | 11/2010 | Lee et al. |
| 7,853,322 B2 | 12/2010 | Bourget et al. |
| 7,860,570 B2 | 12/2010 | Whitehurst et al. |
| 7,865,243 B1 | 1/2011 | Whitehurst et al. |
| 7,877,136 B1 | 1/2011 | Moffitt et al. |
| 7,877,146 B2 | 1/2011 | Rezai |
| 7,881,805 B2 | 2/2011 | Bradley |
| 7,890,176 B2 | 2/2011 | Jaax et al. |
| 7,890,182 B2 | 2/2011 | Parramon et al. |
| 7,914,452 B2 | 3/2011 | Hartley et al. |
| 7,933,654 B2 | 4/2011 | Merfeld et al. |
| 7,937,145 B2 | 5/2011 | Dobak |
| 8,000,794 B2 | 8/2011 | Lozano |
| 8,010,198 B2 | 8/2011 | Libbus et al. |
| 8,010,203 B2 | 8/2011 | DeMulling et al. |

(56) References Cited

U.S. PATENT DOCUMENTS

| | | |
|---|---|---|
| 8,027,718 B2 | 9/2011 | Spinner et al. |
| 8,046,075 B2 | 10/2011 | Rezai |
| 8,060,208 B2 | 11/2011 | Kilgore et al. |
| 8,082,039 B2 | 12/2011 | Kim et al. |
| 8,150,531 B2 | 4/2012 | Skelton |
| 8,170,658 B2 | 5/2012 | Dacey et al. |
| 8,170,675 B2 | 5/2012 | Alataris et al. |
| 8,180,445 B1 | 5/2012 | Moffitt |
| 8,209,021 B2 | 6/2012 | Alataris et al. |
| 8,209,028 B2 | 6/2012 | Skelton et al. |
| 8,224,453 B2 | 7/2012 | De Ridder |
| 8,224,459 B1 | 7/2012 | Pianca et al. |
| 8,255,048 B2 | 8/2012 | Dal Molin et al. |
| 8,280,515 B2 | 10/2012 | Greenspan |
| 8,301,241 B2 | 10/2012 | Ternes et al. |
| 8,340,775 B1 | 12/2012 | Cullen et al. |
| 8,355,792 B2 | 1/2013 | Alataris et al. |
| 8,359,102 B2 | 1/2013 | Alataris et al. |
| 8,359,103 B2 | 1/2013 | Alataris et al. |
| 8,364,271 B2 | 1/2013 | Ridder |
| 8,364,273 B2 | 1/2013 | De Ridder |
| 2,622,601 A1 | 3/2013 | Alataris et al. |
| 8,396,559 B2 | 3/2013 | Alataris et al. |
| 8,412,338 B2 | 4/2013 | Faltys |
| 8,423,147 B2 | 4/2013 | Alataris et al. |
| 8,428,735 B2 | 4/2013 | Littlewood et al. |
| 8,428,748 B2 | 4/2013 | Alataris et al. |
| 8,467,875 B2 | 6/2013 | Bennett et al. |
| 8,483,830 B2 | 7/2013 | Tweden |
| 8,569,935 B1 | 10/2013 | Kosierkiewicz |
| 8,577,458 B1 | 11/2013 | Libbus et al. |
| 8,612,018 B2 | 12/2013 | Gillbe |
| 8,649,874 B2 | 2/2014 | Alataris et al. |
| 8,666,506 B2 | 3/2014 | King |
| 8,688,212 B2 | 4/2014 | Libbus et al. |
| 8,691,877 B2 | 4/2014 | Yun et al. |
| 8,712,534 B2 | 4/2014 | Wei |
| 8,751,009 B2 | 6/2014 | Wacnik |
| 8,768,469 B2 | 7/2014 | Tweden et al. |
| 8,805,512 B1 | 8/2014 | Greiner et al. |
| 8,825,164 B2 | 9/2014 | Tweden et al. |
| 8,825,166 B2 | 9/2014 | John |
| 8,886,326 B2 | 11/2014 | Alataris et al. |
| 8,886,328 B2 | 11/2014 | Alataris et al. |
| 8,892,209 B2 | 11/2014 | Alataris et al. |
| 8,918,172 B2 | 12/2014 | Moffitt et al. |
| 8,918,190 B2 | 12/2014 | Libbus et al. |
| 8,918,191 B2 | 12/2014 | Libbus et al. |
| 8,923,964 B2 | 12/2014 | Libbus et al. |
| 8,923,990 B2 | 12/2014 | Libbus et al. |
| 8,965,521 B2 | 2/2015 | Birkholz et al. |
| 8,996,125 B2 | 3/2015 | Greiner et al. |
| 9,002,457 B2 | 4/2015 | Hamann et al. |
| 9,002,459 B2 | 4/2015 | Lee et al. |
| 9,026,214 B2 | 5/2015 | Ternes et al. |
| 9,026,215 B2 | 5/2015 | Rossing |
| 9,026,226 B2 | 5/2015 | Gerber et al. |
| 9,067,076 B2 | 6/2015 | Nolan et al. |
| 9,101,770 B2 | 8/2015 | Arcot-Krishnamurthy et al. |
| 9,126,044 B2 | 9/2015 | Kramer et al. |
| 9,132,272 B2 | 9/2015 | Alves et al. |
| 9,180,298 B2 | 11/2015 | Alataris et al. |
| 9,205,258 B2 | 12/2015 | Simon et al. |
| 9,211,410 B2 | 12/2015 | Levine et al. |
| 9,295,840 B1 | 3/2016 | Thacker |
| 9,308,370 B2 | 4/2016 | Lima et al. |
| 9,327,127 B2 | 5/2016 | Alataris et al. |
| 9,370,659 B2 | 6/2016 | Franke et al. |
| 9,381,356 B2 | 7/2016 | Parker |
| 9,403,007 B2 | 8/2016 | Moekelke et al. |
| 9,421,355 B2 | 8/2016 | Colborn |
| 9,440,074 B2 | 9/2016 | Ternes et al. |
| 9,462,398 B2 | 10/2016 | Ridder |
| 9,480,846 B2 | 11/2016 | Strother |
| 9,533,153 B2 | 1/2017 | Libbus et al. |
| 9,561,366 B2 | 2/2017 | Wei et al. |
| 9,561,370 B2 | 2/2017 | Rezai |
| 9,572,983 B2 | 2/2017 | Levine et al. |
| 9,694,183 B2 | 7/2017 | Grandhe |
| 9,700,724 B2 | 7/2017 | Liu et al. |
| 9,724,509 B2 | 8/2017 | Su et al. |
| 9,724,511 B2 | 8/2017 | Wei et al. |
| 9,724,513 B2 | 8/2017 | Lane et al. |
| 9,833,614 B1 | 12/2017 | Gliner |
| 9,895,532 B2 | 2/2018 | Kaula et al. |
| 9,895,539 B1 | 2/2018 | Heit |
| 9,913,980 B2 | 3/2018 | Ostroff et al. |
| 9,950,173 B2 | 4/2018 | Doan |
| 9,968,732 B2 | 5/2018 | Drew et al. |
| 10,029,102 B2 | 7/2018 | Doan |
| 10,149,978 B1 | 12/2018 | Park |
| 10,188,856 B1 | 1/2019 | Libbus et al. |
| 10,207,109 B2 | 2/2019 | Zhu et al. |
| 10,220,205 B2 | 3/2019 | Bhadra et al. |
| 10,245,098 B2 | 4/2019 | Davalos |
| 10,328,264 B2 | 6/2019 | Hamann et al. |
| 10,463,861 B2 | 11/2019 | Ternes et al. |
| 10,485,975 B2 | 11/2019 | Greiner et al. |
| 10,493,275 B2 | 12/2019 | Alataris |
| 10,537,740 B2 | 1/2020 | Cabunaru |
| 10,561,845 B2 | 2/2020 | Giftakis et al. |
| 10,632,300 B2 | 4/2020 | Wagenbach et al. |
| 10,675,468 B2 | 6/2020 | Torgerson |
| 10,751,536 B1 | 8/2020 | Heit |
| 10,898,714 B2 | 1/2021 | Libbus et al. |
| 11,045,649 B2 | 6/2021 | Wei et al. |
| 11,229,792 B2 | 1/2022 | Alataris |
| 11,235,153 B2 | 2/2022 | Kibler et al. |
| 11,759,638 B2 | 9/2023 | Alataris |
| 2002/0055779 A1 | 5/2002 | Andrews |
| 2002/0087201 A1 | 7/2002 | Firlik et al. |
| 2002/0128700 A1 | 9/2002 | Cross |
| 2003/0036783 A1 | 2/2003 | Bauhahn |
| 2003/0100931 A1 | 5/2003 | Mullett |
| 2003/0120323 A1 | 6/2003 | Meadows et al. |
| 2003/0135248 A1 | 7/2003 | Stypulkowski |
| 2003/0204221 A1 | 10/2003 | Rodriguez et al. |
| 2004/0015202 A1 | 1/2004 | Chandler et al. |
| 2004/0034394 A1 | 2/2004 | Woods et al. |
| 2004/0039425 A1 | 2/2004 | Greenwood-Van Meerveld |
| 2004/0059395 A1 | 3/2004 | North et al. |
| 2004/0073273 A1 | 4/2004 | Gluckman et al. |
| 2004/0093093 A1 | 5/2004 | Andrews |
| 2004/0116977 A1 | 6/2004 | Finch et al. |
| 2004/0116978 A1 | 6/2004 | Bradley |
| 2004/0122477 A1 | 6/2004 | Whitehorse |
| 2004/0158298 A1 | 8/2004 | Gliner |
| 2004/0158839 A1 | 8/2004 | Gliner et al. |
| 2004/0162590 A1 | 8/2004 | Whitehurst et al. |
| 2004/0167584 A1 | 8/2004 | Carroll et al. |
| 2004/0186532 A1 | 9/2004 | Tadlock |
| 2004/0193228 A1 | 9/2004 | Gerber |
| 2004/0210270 A1 | 10/2004 | Erickson |
| 2004/0210271 A1 | 10/2004 | Campen et al. |
| 2004/0267330 A1 | 12/2004 | Lee et al. |
| 2005/0021104 A1 | 1/2005 | DiLorenzo |
| 2005/0033381 A1 | 2/2005 | Carter et al. |
| 2005/0038489 A1 | 2/2005 | Grill |
| 2005/0060001 A1 | 3/2005 | Singhal et al. |
| 2005/0070982 A1 | 3/2005 | Heruth et al. |
| 2005/0113877 A1 | 5/2005 | Spinelli et al. |
| 2005/0113878 A1 | 5/2005 | Gerber |
| 2005/0113882 A1 | 5/2005 | Cameron et al. |
| 2005/0119713 A1 | 6/2005 | Whitehurst et al. |
| 2005/0143783 A1 | 6/2005 | Boveja |
| 2005/0143789 A1 | 6/2005 | Whitehurst et al. |
| 2005/0149148 A1 | 7/2005 | King |
| 2005/0153885 A1 | 7/2005 | Yun et al. |
| 2005/0154435 A1 | 7/2005 | Stern et al. |
| 2005/0222641 A1 | 10/2005 | Pless |
| 2005/0240241 A1 | 10/2005 | Yun et al. |
| 2005/0245978 A1 | 11/2005 | Varrichio et al. |
| 2005/0245987 A1 | 11/2005 | Woods |
| 2005/0246006 A1 | 11/2005 | Daniels |

(56) References Cited

U.S. PATENT DOCUMENTS

| | | |
|---|---|---|
| 2005/0267545 A1 | 12/2005 | Cory |
| 2005/0278000 A1 | 12/2005 | Strother et al. |
| 2005/0288721 A1 | 12/2005 | Girouard |
| 2006/0004422 A1 | 1/2006 | De Ridder |
| 2006/0009820 A1 | 1/2006 | Royle |
| 2006/0015153 A1 | 1/2006 | Gliner et al. |
| 2006/0030895 A1 | 2/2006 | Simon et al. |
| 2006/0041285 A1 | 2/2006 | Johnson |
| 2006/0074456 A1 | 4/2006 | Pyles et al. |
| 2006/0079937 A1 | 4/2006 | King et al. |
| 2006/0095088 A1 | 5/2006 | De Ridder |
| 2006/0100671 A1 | 5/2006 | Ridder |
| 2006/0149337 A1 | 7/2006 | John |
| 2006/0161219 A1 | 7/2006 | Mock et al. |
| 2006/0161235 A1 | 7/2006 | King |
| 2006/0167512 A1 | 7/2006 | Ross et al. |
| 2006/0167525 A1 | 7/2006 | King |
| 2006/0168805 A1 | 8/2006 | Hegland et al. |
| 2006/0190044 A1 | 8/2006 | Libbus et al. |
| 2006/0190048 A1 | 8/2006 | Gerber |
| 2006/0224187 A1 | 10/2006 | Bradley et al. |
| 2006/0229687 A1 | 10/2006 | Goetz et al. |
| 2006/0253182 A1 | 11/2006 | King |
| 2006/0271108 A1 | 11/2006 | Libbus et al. |
| 2007/0021803 A1 | 1/2007 | Deem et al. |
| 2007/0032827 A1 | 2/2007 | Katims |
| 2007/0039625 A1 | 2/2007 | Heruth et al. |
| 2007/0043400 A1 | 2/2007 | Donders et al. |
| 2007/0049988 A1 | 3/2007 | Carbunaru |
| 2007/0049991 A1 | 3/2007 | Klostermann et al. |
| 2007/0060954 A1 | 3/2007 | Cameron et al. |
| 2007/0066997 A1 | 3/2007 | He et al. |
| 2007/0073353 A1 | 3/2007 | Rooney et al. |
| 2007/0073354 A1 | 3/2007 | Knudson et al. |
| 2007/0083240 A1 | 4/2007 | Peterson et al. |
| 2007/0100388 A1 | 5/2007 | Gerber |
| 2007/0106337 A1 | 5/2007 | Errico et al. |
| 2007/0106342 A1 | 5/2007 | Schumann |
| 2007/0150029 A1 | 6/2007 | Bourget et al. |
| 2007/0150034 A1 | 6/2007 | Rooney et al. |
| 2007/0156183 A1 | 7/2007 | Rhodes |
| 2007/0167992 A1 | 7/2007 | Carley |
| 2007/0179559 A1 | 8/2007 | Giftakis et al. |
| 2007/0179579 A1 | 8/2007 | Feler et al. |
| 2007/0191902 A1 | 8/2007 | Errico |
| 2007/0203537 A1 | 8/2007 | Goetz et al. |
| 2007/0213789 A1 | 9/2007 | Nolan et al. |
| 2007/0239226 A1 | 10/2007 | Overstreet |
| 2007/0244522 A1 | 10/2007 | Overstreet |
| 2007/0255118 A1 | 11/2007 | Miesel et al. |
| 2007/0265681 A1 | 11/2007 | Gerber et al. |
| 2007/0293893 A1 | 12/2007 | Stolen et al. |
| 2007/0299482 A1 | 12/2007 | Littlewood et al. |
| 2008/0033511 A1 | 2/2008 | Dobak |
| 2008/0046012 A1 | 2/2008 | Covalin et al. |
| 2008/0051839 A1 | 2/2008 | Libbus et al. |
| 2008/0065158 A1 | 3/2008 | Ben-Ezra |
| 2008/0086036 A1 | 4/2008 | Hartley |
| 2008/0097539 A1 | 4/2008 | Belalcazar |
| 2008/0103570 A1 | 5/2008 | Gerber |
| 2008/0167697 A1 | 7/2008 | Johnson |
| 2008/0183259 A1 | 7/2008 | Bly et al. |
| 2008/0234791 A1 | 9/2008 | Arle et al. |
| 2008/0269854 A1 | 10/2008 | Hegland et al. |
| 2008/0281381 A1 | 11/2008 | Gerber et al. |
| 2008/0300449 A1 | 12/2008 | Gerber |
| 2008/0319511 A1 | 12/2008 | Pless |
| 2009/0018617 A1 | 1/2009 | Skelton et al. |
| 2009/0024187 A1 | 1/2009 | Erickson et al. |
| 2009/0024189 A1 | 1/2009 | Lee et al. |
| 2009/0036945 A1 | 2/2009 | Chancellor et al. |
| 2009/0054962 A1 | 2/2009 | Lefler et al. |
| 2009/0069803 A1 | 3/2009 | Starkebaum |
| 2009/0076565 A1 | 3/2009 | Surwit |
| 2009/0083070 A1 | 3/2009 | Giftakis |
| 2009/0112282 A1 | 4/2009 | Kast et al. |
| 2009/0118777 A1 | 5/2009 | Iki |
| 2009/0125079 A1 | 5/2009 | Armstrong et al. |
| 2009/0132010 A1 | 5/2009 | Kronberg |
| 2009/0132016 A1 | 5/2009 | Putz |
| 2009/0157141 A1 | 6/2009 | Chiao et al. |
| 2009/0157149 A1 | 6/2009 | Wahlgren et al. |
| 2009/0196472 A1 | 8/2009 | Goetz et al. |
| 2009/0198306 A1 | 8/2009 | Goetz et al. |
| 2009/0204173 A1 | 8/2009 | Fang et al. |
| 2009/0204192 A1 | 8/2009 | Carlton et al. |
| 2009/0264789 A1 | 10/2009 | Molnar |
| 2009/0281595 A1 | 11/2009 | King et al. |
| 2009/0287274 A1 | 11/2009 | De Ridder |
| 2009/0287279 A1 | 11/2009 | Parramon et al. |
| 2009/0326611 A1 | 12/2009 | Gillbe |
| 2010/0010567 A1 | 1/2010 | Deem et al. |
| 2010/0016929 A1 | 1/2010 | Prochazka |
| 2010/0036454 A1 | 2/2010 | Bennett et al. |
| 2010/0042193 A1 | 2/2010 | Slavin |
| 2010/0057178 A1 | 3/2010 | Simon |
| 2010/0094375 A1 | 4/2010 | Donders et al. |
| 2010/0125313 A1 | 5/2010 | Lee et al. |
| 2010/0137938 A1 | 6/2010 | Kishawi et al. |
| 2010/0152817 A1 | 6/2010 | Gillbe |
| 2010/0191307 A1 | 7/2010 | Fang et al. |
| 2010/0198298 A1 | 8/2010 | Glukhovsky |
| 2010/0241190 A1 | 9/2010 | Kilgore et al. |
| 2010/0249875 A1 | 9/2010 | Kishawi et al. |
| 2010/0256696 A1 | 10/2010 | Schleicher et al. |
| 2010/0274312 A1 | 10/2010 | Alataris et al. |
| 2010/0274314 A1 | 10/2010 | Alataris et al. |
| 2010/0274315 A1 | 10/2010 | Alataris et al. |
| 2010/0274316 A1 | 10/2010 | Alataris et al. |
| 2010/0274317 A1 | 10/2010 | Parker et al. |
| 2010/0274318 A1 | 10/2010 | Walker et al. |
| 2010/0274320 A1 | 10/2010 | Torgerson |
| 2010/0274326 A1 | 10/2010 | Chitre et al. |
| 2010/0324630 A1 | 12/2010 | Lee et al. |
| 2010/0331916 A1 | 12/2010 | Parramon et al. |
| 2011/0009919 A1 | 1/2011 | Carbunaru et al. |
| 2011/0009923 A1 | 1/2011 | Lee |
| 2011/0009927 A1 | 1/2011 | Parker et al. |
| 2011/0022114 A1 | 1/2011 | Navarro |
| 2011/0040291 A1 | 2/2011 | Weissenrieder-Norlin et al. |
| 2011/0071589 A1 | 3/2011 | Starkebaum et al. |
| 2011/0106208 A1* | 5/2011 | Faltys ............... A61N 1/36071 607/46 |
| 2011/0184301 A1 | 7/2011 | Holmstrom et al. |
| 2011/0184486 A1 | 7/2011 | De Ridder |
| 2011/0184488 A1 | 7/2011 | De Ridder |
| 2011/0201977 A1 | 8/2011 | Tass |
| 2011/0276107 A1 | 11/2011 | Simon et al. |
| 2011/0282412 A1 | 11/2011 | Glukhovsky et al. |
| 2012/0010680 A1 | 1/2012 | Wei |
| 2012/0016437 A1 | 1/2012 | Alataris et al. |
| 2012/0016438 A1 | 1/2012 | Alataris et al. |
| 2012/0016439 A1 | 1/2012 | Alataris et al. |
| 2012/0089200 A1 | 4/2012 | Ranu et al. |
| 2012/0150252 A1 | 6/2012 | Feldman et al. |
| 2012/0083857 A1 | 8/2012 | Bradley |
| 2012/0203304 A1 | 8/2012 | Alataris et al. |
| 2012/0209349 A1 | 8/2012 | Alataris et al. |
| 2012/0277833 A1 | 11/2012 | Gerber et al. |
| 2012/0283797 A1 | 11/2012 | De Ridder |
| 2013/0006325 A1 | 1/2013 | Woods et al. |
| 2013/0023951 A1 | 1/2013 | Greenspan |
| 2013/0041425 A1 | 2/2013 | Fang et al. |
| 2013/0066411 A1 | 3/2013 | Thacker et al. |
| 2013/0079840 A1 | 3/2013 | Su et al. |
| 2013/0079841 A1 | 3/2013 | Su |
| 2013/0096643 A1 | 4/2013 | Fang et al. |
| 2013/0096644 A1 | 4/2013 | Fang et al. |
| 2013/0110196 A1 | 5/2013 | Alataris et al. |
| 2013/0123879 A1 | 5/2013 | Alataris et al. |
| 2013/0172955 A1 | 7/2013 | Alataris |
| 2013/0204173 A1 | 8/2013 | Kelly et al. |
| 2013/0204320 A1 | 8/2013 | Alataris et al. |
| 2013/0204321 A1 | 8/2013 | Alataris et al. |

(56) References Cited

U.S. PATENT DOCUMENTS

| | | |
|---|---|---|
| 2013/0204322 A1 | 8/2013 | Alataris et al. |
| 2013/0204323 A1 | 8/2013 | Thacker et al. |
| 2013/0204324 A1 | 8/2013 | Thacker et al. |
| 2013/0204338 A1 | 8/2013 | Alataris et al. |
| 2013/0211487 A1 | 8/2013 | Fang et al. |
| 2013/0237948 A1 | 9/2013 | Donders |
| 2013/0261695 A1 | 10/2013 | Thacker et al. |
| 2013/0261696 A1 | 10/2013 | Alataris et al. |
| 2013/0261697 A1 | 10/2013 | Alataris et al. |
| 2013/0282078 A1 | 10/2013 | Wacnik |
| 2013/0289659 A1 | 10/2013 | Nelson |
| 2014/0005744 A1 | 1/2014 | Hershey |
| 2014/0031896 A1 | 1/2014 | Alataris et al. |
| 2014/0142656 A1 | 5/2014 | Alataris et al. |
| 2014/0142657 A1 | 5/2014 | Alataris et al. |
| 2014/0142658 A1 | 5/2014 | Alataris et al. |
| 2014/0142659 A1 | 5/2014 | Alataris et al. |
| 2014/0142673 A1 | 5/2014 | Alataris et al. |
| 2014/0316484 A1 | 10/2014 | Edgerton |
| 2014/0343622 A1 | 11/2014 | Alataris et al. |
| 2014/0379044 A1 | 12/2014 | Walker et al. |
| 2015/0005842 A1 | 1/2015 | Lee |
| 2015/0012079 A1 | 1/2015 | Goroszeniuk et al. |
| 2015/0018896 A1 | 1/2015 | Alataris et al. |
| 2015/0032181 A1 | 1/2015 | Baynham |
| 2015/0032182 A1 | 1/2015 | Alataris et al. |
| 2015/0032183 A1 | 1/2015 | Alataris et al. |
| 2015/0039040 A1 | 2/2015 | Cowan et al. |
| 2015/0039049 A1 | 2/2015 | Alataris et al. |
| 2015/0039050 A1 | 2/2015 | Alataris et al. |
| 2015/0045853 A1 | 2/2015 | Alataris et al. |
| 2015/0045854 A1 | 2/2015 | Alataris et al. |
| 2015/0051664 A1 | 2/2015 | Alataris et al. |
| 2015/0051665 A1 | 2/2015 | Hershey et al. |
| 2015/0073510 A1 | 3/2015 | Perryman |
| 2015/0202444 A1 | 7/2015 | Franke et al. |
| 2015/0217116 A1 | 8/2015 | Parramon et al. |
| 2015/0343220 A1 | 12/2015 | Alataris et al. |
| 2016/0114165 A1 | 4/2016 | Levine et al. |
| 2016/0121119 A1 | 5/2016 | Alataris et al. |
| 2016/0256689 A1 | 9/2016 | Vallejo et al. |
| 2016/0263376 A1 | 9/2016 | Yoo et al. |
| 2016/0287872 A1 | 10/2016 | Alataris et al. |
| 2016/0287873 A1 | 10/2016 | Alataris et al. |
| 2016/0287874 A1 | 10/2016 | Alataris et al. |
| 2016/0287875 A1 | 10/2016 | Thacker et al. |
| 2016/0287888 A1 | 10/2016 | Alataris et al. |
| 2016/0303374 A1 | 10/2016 | Alataris et al. |
| 2016/0339239 A1 | 11/2016 | Yoo et al. |
| 2017/0001003 A1 | 1/2017 | Pivonka |
| 2017/0036020 A1 | 2/2017 | Harrah |
| 2017/0050021 A1 | 2/2017 | Cosman, Sr. |
| 2017/0087369 A1 | 3/2017 | Bokil |
| 2017/0095669 A1 | 4/2017 | Libbus et al. |
| 2017/0128722 A1 | 5/2017 | Perez |
| 2017/0165485 A1 | 6/2017 | Sullivan et al. |
| 2017/0216602 A1 | 8/2017 | Waataja et al. |
| 2017/0239470 A1 | 8/2017 | Wei et al. |
| 2017/0274209 A1 | 9/2017 | Edgerton |
| 2017/0348526 A1 | 12/2017 | Southwell |
| 2018/0123780 A1 | 5/2018 | Ikarashi et al. |
| 2018/0256906 A1 | 9/2018 | Pivonka |
| 2018/0272132 A1 | 9/2018 | Subbaroyan |
| 2018/0353758 A1 | 12/2018 | Vallejo |
| 2019/0001135 A1 | 1/2019 | Yoo et al. |
| 2019/0060647 A1 | 2/2019 | Su |
| 2019/0321641 A1 | 10/2019 | Baldoni |
| 2019/0329025 A1 | 10/2019 | Moffitt et al. |
| 2020/0139138 A1 | 5/2020 | Sit |
| 2022/0273950 A1 | 9/2022 | Alataris et al. |

FOREIGN PATENT DOCUMENTS

| | | |
|---|---|---|
| DE | 10318071 A1 | 11/2004 |
| EP | 1070518 | 1/2001 |
| EP | 1181947 A2 | 2/2002 |
| EP | 2243511 A2 | 10/2010 |
| EP | 2448633 A1 | 5/2012 |
| EP | 2630984 A1 | 8/2013 |
| EP | 2586491 | 8/2016 |
| GB | 2449546 A | 11/2008 |
| JP | 2002200179 A | 7/2002 |
| JP | 2007528774 A | 10/2007 |
| JP | 2008500086 | 1/2008 |
| SU | 1512625 A1 | 10/1989 |
| SU | 1690727 A1 | 11/1991 |
| WO | WO-02065896 A2 | 8/2002 |
| WO | WO-02/085448 | 10/2002 |
| WO | WO-02092165 A1 | 11/2002 |
| WO | WO-03015863 A2 | 2/2003 |
| WO | WO-03066154 A2 | 8/2003 |
| WO | WO-2004007018 A1 | 1/2004 |
| WO | WO-2005087314 | 9/2005 |
| WO | WO-2005115532 A2 | 12/2005 |
| WO | WO-2006007048 | 1/2006 |
| WO | WO-2006057734 A1 | 6/2006 |
| WO | WO-2006063458 | 6/2006 |
| WO | WO-2006084635 A2 | 8/2006 |
| WO | WO-2006119046 A1 | 11/2006 |
| WO | WO-2007035925 A2 | 3/2007 |
| WO | WO-2007082382 A1 | 7/2007 |
| WO | WO-2007103324 A1 | 9/2007 |
| WO | WO-2007117232 A1 | 10/2007 |
| WO | WO-2008039982 A2 | 4/2008 |
| WO | WO-2008045434 A2 | 4/2008 |
| WO | WO-2008106174 A1 | 9/2008 |
| WO | WO-2008121891 A1 | 10/2008 |
| WO | WO-2008140940 | 11/2008 |
| WO | WO-2008142402 A1 | 11/2008 |
| WO | WO-2008153726 A2 | 12/2008 |
| WO | WO-2009018518 A1 | 2/2009 |
| WO | WO-2009061813 A1 | 5/2009 |
| WO | WO-2009097224 | 8/2009 |
| WO | WO-20090129329 A1 | 10/2009 |
| WO | WO-2010111358 A2 | 9/2010 |
| WO | WO-2011014570 A1 | 2/2011 |
| WO | WO-2012154985 | 11/2012 |
| WO | WO-2016154091 A1 | 9/2016 |
| WO | WO-2017044904 | 3/2017 |
| WO | WO-2017146658 | 8/2017 |
| WO | WO-2020236946 | 11/2020 |
| WO | WO-2020254794 | 12/2020 |

OTHER PUBLICATIONS

U.S. Appl. No. 15/606,869, filed May 26, 2017, Lee.
Defendant's Boston Scientific Corporation's and Boston Scientific Neuromodulation Corporation's Preliminary Invalidity Contentions, Case No. 3:16-cv-06830-VC, filed Mar. 17, 2017, 159 pages.
Exhibit A1: Invalidity Chart v. MacDonald (U.S. Pat. No. 5,776,170), Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), Mar. 17, 2017, 294 pages.
Exhibit A2: Invalidity Chart v. Spinner (U.S. Patent Application Publication No. 2007/0213771), Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), Mar. 17, 2017, 235 pages.
Exhibit A3: Invalidity Chart v. Knudson (U.S. Patent Application Publication No. 2007/0073354), Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), Mar. 17, 2017, 301 pages.
Exhibit A4: Invalidity Chart v. Butukhanov (Soviet Union Publication No. 1512625), Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), Mar. 17, 2017, 233 pages.

(56) References Cited

OTHER PUBLICATIONS

Exhibit A5: Invalidity Chart v. Sluijter (U.S. Pat. No. 6,246,912), Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), Mar. 17, 2017, 226 pages.

Exhibit A6: Invalidity Chart v. Kilgore (U.S. Pat. No. 7,389,145), Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), Mar. 17, 2017, 219 pages.

Exhibit A7: Invalidity Chart v. Royle (U.S. Patent Application Publication No. 2006/0009820), Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), Mar. 17, 2017, 188 pages.

Exhibit A8: Invalidity Chart v. King (U.S. Patent Application Publication No. 2007/0149148), Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), Mar. 17, 2017, 222 pages.

Exhibit A9: Invalidity Chart v. DeRidder (U.S. Patent Application Publication No. 2011/0184488), Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), Mar. 17, 2017, 266 pages.

Exhibit B1: Invalidity Chart v. Boston Scientific's Precision Spinal Cord Stimulation System, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), Mar. 17, 2017, 337 pages.

Exhibit C1: 35 U.S.C. § 103(a) Invalidity Chart, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), Mar. 17, 2017, 400 pages.

Boston Scientific's Answer to First Amended Complaint and Defense, *Nevro Corp. vs. Boston Scientific Corporation and Boston Scientific Neuromodulation Corporation*, Case No. 3:16-cv-06830-VC, Jul. 13, 2017, 22 pages.

Defendant's First Amended Preliminary Invalidity Contentions, *Nevro Corp. v. Boston Scientific Corporation and Boston Scientific Neuromodulation Corporation*, Case No. 3:16-cv-06830-VC, Jun. 17, 2017, 93 pages.

Amended Exhibit C1 (amendments redlined): 35 U.S.C. § 103(a) Invalidity Chart, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), Jun. 13, 2017, 423 pages.

First Amended Complaint for Patent Infringement and Declaratory Judgment, *Nevro Corp. v. Boston Scientific Corporation and Boston Scientific Neuromodulation Corporation*, Case No. 3:16-cv-06830-VC, Jun. 29, 2017, 45 pages.

Defendant's Second Amended Preliminary Invalidity Contentions, *Nevro Corp. vs. Boston Scientific Corporation and Boston Scientific Neuromodulation Corporation*, Case No. 3:16-cv-06830-VC, Aug. 10, 2017, 108 pages.

Exhibit A10: Invalidity Chart v. Fang (U.S. Patent Application Publication No. 2009/0204173), Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), Mar. 17, 2017, 191 pages.

Exhibit A1 for Defendant's Second Amended Preliminary Invalidity Contentions: Invalidity Chart v. MacDonald (U.S. Pat. No. 5,776,170), Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), Aug. 10, 2017, 168 pages.

Exhibit A2 for Defendant's Second Amended Preliminary Invalidity Contentions: Invalidity Chart v. Spinner (U.S. Patent Application Publication No. 2007/0213771), Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), Aug. 10, 2017, 129 pages.

Exhibit A3 for Defendant's Second Amended Preliminary Invalidity Contentions: Invalidity Chart v. Knudson (U.S. Patent Application Publication No. 2007/0073354), Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), Aug. 10, 2017, 173 pages.

Exhibit A5 for Defendant's Second Amended Preliminary Invalidity Contentions: Invalidity Chart v. Sluijter (U.S. Pat. No. 6,246,912), Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), Aug. 10, 2017, 135 pages.

Exhibit A6 for Defendant's Second Amended Preliminary Invalidity Contentions: Invalidity Chart v. Kilgore (U.S. Pat. No. 7,389,145), Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), Aug. 10, 2017, 110 pages.

Exhibit A7 for Defendant's Second Amended Preliminary Invalidity Contentions: Invalidity Chart v. Royle (U.S. Patent Application Publication No. 2006/0009820), Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3: 16-cv-06830-VC (N.D. Cal.), Aug. 10, 2017, 111 pages.

Exhibit A9 for Defendant's Second Amended Preliminary Invalidity Contentions: Invalidity Chart v. DeRidder (U.S. Patent Application Publication No. 2011/0184488), Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), Aug. 10, 2017, 160 pages.

Exhibit A10 for Defendant's Second Amended Preliminary Invalidity Contentions: Invalidity Chart v. Fang (U.S. Patent Application Publication No. 2009/0204173), Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), Aug. 10, 2017, 114 pages.

Exhibit A11 for Defendant's Second Amended Preliminary Invalidity Contentions: Invalidity Chart v. Alataris (U.S. Pat. No. 8,712,533), Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), Aug. 10, 2017, 13 pages.

Exhibit A12 for Defendant's Second Amended Preliminary Invalidity Contentions: Invalidity Chart v. Gaunt (U.S. Patent Publication No. 2006/0184211), Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), Aug. 10, 2017, 113 pages.

Exhibit B1 for Defendant's Second Amended Preliminary Invalidity Contentions: Invalidity Chart v. Boston Scientific's Precision Spinal Cord Stimulation System, Boston Scientific Corporation's and

(56) References Cited

OTHER PUBLICATIONS

Boston Scientific Neuromodulation Corporation's Invalidity Contentions, *Nevro Corp.* v. *Boston Scientific Corporation and Boston Scientific Neuromodulation Corporation*, Case No. 3:16-cv-06830-VC (N.D. Cal.), Aug. 10, 2017, 180 pages.
Exhibit C1 for Defendant's Second Amended Preliminary Invalidity Contentions: 35 U.S.C. § 103(a) Invalidity Chart, Boston Scientific Corporation's and Boston Scientific Neuromodulation Corporation's Invalidity Contentions, *Nevro Corp.* v. *Boston Scientific Corporation and Boston Scientific Neuromodulation Corporation*, Case No. 3:16-cv-06830-VC (N.D. Cal.), Aug. 10, 2017, 174 pages.
Corrected Exhibit C1 for Defendant's Second Amended Preliminary Invalidity Contentions: 35 U.S.C. § 103(a) Invalidity Chart, Boston Scientific Corporation's and Boston Scientific Neuromodulation Corporation's Invalidity Contentions, *Nevro Corp.* v. *Boston Scientific Corporation and Boston Scientific Neuromodulation Corporation*, Case No. 3:16-cv-06830-VC (N.D. Cal.), Aug. 10, 2017, 171 pages.
Statement of Grounds of Appeal for the Opposition of European Patent No. 2421600 (Appeal No. T1450/17-3.4.01) by Boston Scientific Neuromodulation Corporation, Aug. 14, 2017, 17 pages.
Nevro's Notice of Appeal for Opposition by Medtronic, Inc., and Boston Scientific Neuromodulation Corporation for European Patent No. 2243510, mailed Aug. 3, 2017, 1 page.
Provision of Minutes in accordance with Rule 124(4) EPC for Opposition by Medtronic, Inc., and Boston Scientific Neuromodulation Corporation for European Patent No. 2243510, mailed Jul. 27, 2017, 23 pages.
Decision Revoking the European Patent for Opposition by Medtronic, Inc., and Boston Scientific Neuromodulation Corporation for European Patent No. 2243510, mailed Jul. 27, 2017, 37 pages.
Nevro's Reply of the Patentee to the Notices of Opposition filed by Medtronic, Inc., and Boston Scientific Neuromodulation Corporation for EP2853285, filed Nov. 3, 2017, 34 pages.
Corrected Rebuttal Expert Report of Ben Pless Regarding Validity on behalf of Plaintiff Nevro Corp., regarding Invalidity of U.S. Pat. Nos. 8,712,533, 9,327,125, 8,359,102, 9,480,842, 9,333,357, 8,792,988, and 8,768,472, *Nevro Corp.* vs. *Boston Scientific Corporation and Boston Scientific Neuromodulation Corporation*, Case No. 3:16-cv-06830-VC-MEJ, Mar. 5, 2018, 785 pages.
Expert Report of Richard T. Mihran, Ph.D., regarding Invalidity of U.S. Pat. Nos. 8,712,533, 9,327,125, 8,359,102, 9,480,842, 9,333,357, 8,792,988, and 8,768,472, *Nevro Corp.* vs. *Boston Scientific Corporation and Boston Scientific Neuromodulation Corporation*, Case No. 3:16-cv-06830-VC-MEJ, Jan. 18, 2018, 958 pages.
Rebuttal Expert Report of Richard T. Mihran, Ph.D., regarding Invalidity of U.S. Pat. Nos. 8,712,533, 9,327,125, 8,359,102, 9,480,842, 9,333,357, 8,792,988, and 8,768,472, *Nevro Corp.* vs. *Boston Scientific Corporation and Boston Scientific Neuromodulation Corporation*, Case No. 3:16-cv-06830-VC-MEJ, Feb. 14, 2018, 195 pages.
Nevro Observations and Response to Notice of Oppositions filed by Medtronic Inc., and Boston Scientific for European Patent No. 2207587, mailed Aug. 26, 2016, 16 pages.
Nevro Response to Notice of Oppositions filed by Boston Scientific for European Patent No. 2421600, mailed Jul. 22, 2015, 16 pages.
Nevro Response to Notice of Oppositions filed by Medtronic and Boston Scientific for European Patent No. 2630984, mailed Dec. 7, 2015, 26 pages.
Nevro Response to Opposition of Division's Comments and Summons to Oral Proceedings for European Patent No. 2630984, mailed Oct. 25, 2016, 8 pages.
Nevro Written Submissions and Response to Notice of Oppositions filed by Medtronic Inc., and Boston Scientific for European Patent No. 2243510, mailed Aug. 28, 2015, 17 pages.
Nevro's Response to Preliminary Opinion for Opposition by Medtronic, Inc., and Boston Scientific Neuromodulation Corporation for European Patent No. 2243510, mailed Feb. 3, 2017, 36 pages.
Nevro's Statement of Grounds of Appeal for EP2243510 (Appeal No. T 17484/17-3.4.01), filed Nov. 30, 2017, 16 pages.
Nevro's Response to Further Submission by Medtronic, Inc., and Boston Scientific Neuromodulation Corporation for European Patent No. 2243510, mailed Feb. 24, 2017, 9 pages.
Nevros Response to Opponent Submission of Declaration of Jonathan Miller in European Patent No. 2630984, mailed Nov. 18, 2016, 4 pages.
Notice of Opposition to a European Patent for European Patent No. 2853285, Proprietor of the Patent: Nevro Corporation, Opponent: Medtronic, Inc., Apr. 19, 2017, 40 pages.
Notice of Opposition to a European Patent for European Patent No. 2853285, Proprietor of the Patent: Nevro Corporation, Opponent: Boston Scientific Neuromodulation Corporation, May 16, 2017, 18 pages.
Notice of Opposition to a European Patent for European Patent No. 2586488, Proprietor of the Patent: Nevro Corporation, Opponent: Medtronic, Inc., Mar. 15, 2017, 7 pages.
Notice of Opposition to a European Patent, Argument and Facts for European Patent No. 2630984, Proprietor of the Patent: Nevro Corporation; Opponent: Medtronic, Mar. 17, 2015, 17 pages.
Notice of Opposition to a European Patent, Argument and Facts, and Annex for European Patent No. 2630984, Proprietor of the Patent: Nevro Corporation; Opponent: Boston Scientific Neuromodulation Corporation, Mar. 17, 2015, 21 pages.
Notice of Opposition to a European Patent, Argument and Facts, and Annex for European Patent No. 2421600, Proprietor of the Patent: Nevro Corporation; Opponent: Boston Scientific Neuromodulation Corporation, Dec. 4, 2014, 22 pages.
Notice of Opposition to a European Patent, Argument and Facts, for European Patent No. 2243510, Proprietor of the Patent: Nevro Corporation, Opponent: Medtronic, Jan. 8, 2015, 22 pages.
Notice of Opposition to a European Patent, Argument and Facts, and Annex for European Patent No. 2243510, Proprietor of the Patent: Nevro Corporation; Opponent: Boston Scientific Neuromodulation Corporation, Jan. 8, 2015, 28 pages.
Notice of Opposition to a European Patent, Argument and Facts, for European Patent No. 2207587, Proprietor of the Patent: Nevro Corporation; Opponent: Medtronic, Inc., Jan. 12, 2016, 22 pages.
Notice of Opposition to a European Patent, Argument and Facts, for European Patent No. 2207587, Proprietor of the Patent: Nevro Corporation; Opponent: Boston Scientific Neuromodulation Corporation, Jan. 8, 2016, 17 pages.
Notice of Opposition to a European Patent, Argument and Facts, for European Patent No. 2586488, Proprietor of the Patent: Nevro Corporation; Opponent: Boston Scientific Neuromodulation Corporation, Dec. 15, 2017, 35 pages.
Opponent Boston Scientific: Response to Attend Oral Proceedings for European Patent No. 2630984, mailed Oct. 25, 2016, 21 pages.
Opponent Response to Patent Proprietor Comments to Declaration of Dr. Jonathan Miller for European Patent No. 2630984, mailed Nov. 22, 2016, 3 pages.
Opponents Boston Scientific Neuromodulation Corp.: Additional Observations in view of Oral Proceedings for European Patent No. 2243510, mailed Feb. 3, 2017, 8 pages.
Opponents Boston Scientific Neuromodulation Corporation: Response to Nov. 9, 2017 Brief Communication in Opposition for European Patent No. 2853285, mailed Feb. 13, 2018, 9 pages.
Opponents Boston Scientific: Response to Summons to Attend Oral Proceedings for European Patent No. 2421600, mailed Jan. 2, 2017, 15 pages.
Opponents Medtronic, Inc.: Additional Observations in view of Oral Proceedings for European Patent No. 2243510, mailed Feb. 3, 2017, 10 pages.
Opponents Medtronic, Inc.: Facts and Arguments in Support of Opposition for European Patent No. 2586488, mailed Dec. 15, 2017, 18 pages.
Opponents Medtronic, Inc.: Response to Attend Oral Proceedings for European Patent No. 2630984, mailed Oct. 25, 2016, 26 pages.
Opponents Medtronic: Response to Nevro Requests and Submission for European Patent No. 22453510, mailed Mar. 29, 2017, 3 pages.
Opponents Response to Patentee's (Nevro) Written Submissions for European Patent No. 2243510, mailed Feb. 22, 2016, 21 pages.

(56) References Cited

OTHER PUBLICATIONS

Nevro's Motion for Summary Adjudication—Notice of Motion, Motion and Memorandum of Points and Authorities in the Support of Nevro's Motion for Summary Adjudication (Document 461), *Nevro Corp.* vs. *Boston Scientific Corporation and Boston Scientific Neuromodulation Corporation*, Case No. 3:16-cv-06830-VC-MEJ, filed Jul. 30, 2018, 50 pages.
Declaration of Konstantinos Alataris in Support of Nevro's Motion of Summary Adjudication (Document 342-1), *Nevro Corp.* vs. *Boston Scientific Corporation and Boston Scientific Neuromodulation Corporation*, Case No. 3:16-cv-06830-VC-MEJ, Apr. 11, 2018, 3 pages.
Exhibit 1 for Declaration of Konstantinos Alataris in Support of Nevro's Motion of Summary Adjudication (Document 342-2), Notes from NBI Mayo Physician Meeting Dec. 4, 2016, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), Apr. 12, 2018, 3 pages.
Exhibit 2 for Declaration of Konstantinos Alataris in Support of Nevro's Motion of Summary Adjudication (Document 342-3), Notes from NBI Development—Mayo Clinic Dec. 4, 2016, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 11 pages.
Exhibit 3 for Declaration of Konstantinos Alataris in Support of Nevro's Motion of Summary Adjudication (Document 342-4), Sep. 2007 Email between O. Filho and Konstantinos Alataris, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 4 pages.
Exhibit 4 for Declaration of Konstantinos Alataris in Support of Nevro's Motion of Summary Adjudication (Document 342-5) NBI Development Inc., Jun. 12, 2007 Board Meeting, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 31 pages.
Declaration of Ben Pless in Support of Nevro's Motion for Summary Adjudication (Updated Redacted Version of EFC No. 347-24), *Nevro Corp. v. Boston Scientific Corporation and Boston Scientific Neuromodulation Corporation*, Case No. 3:16-cv-06830-VC-MEJ, Apr. 11, 2018, 64 pages.
Exhibit A for Declaration of Ben Pless in Support of Nevro's Motion for Summary Adjudication (Document 342-7) Curriculum Vitae of Benjamin Pless, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Jul. 30, 2018, 15 pages.
Declaration of Eric C. Pai in Support of Nevro's Motion for Summary Adjudication (Document 343), *Nevro Corp. v. Boston Scientific Corporation and Boston Scientific Neuromodulation Corporation*, Case No. 3:16-cv-06830-VC-MEJ, Apr. 12, 2018, 11 pages.
Exhibit 1 for Declaration of Eric C. Pai in Support of Nevro's Motion for Summary Adjudication (Document 343-1) Chart—Asserted Claims with Disputed Terms Underlined, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 5 pages.
Exhibit 2 for Declaration of Eric C. Pai in Support of Nevro's Motion for Summary Adjudication (Document 343-2) Certified Copy of U.S. Pat. No. 8,359,102, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 34 pages.
Exhibit 3 for Declaration of Eric C. Pai in Support of Nevro's Motion for Summary Adjudication (Document 343-3) Certified Copy of U.S. Pat. No. 8,712,533, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 37 pages.
Exhibit 4 for Declaration of Eric C. Pai in Support of Nevro's Motion for Summary Adjudication (Document 343-4) Certified Copy of U.S. Pat. No. 8,768,472, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 37 pages.
Exhibit 5 for Declaration of Eric C. Pai in Support of Nevro's Motion for Summary Adjudication (Document 343-5) Certified Copy of U.S. Pat. No. 8,792,988, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 35 pages.
Exhibit 6 for Declaration of Eric C. Pai in Support of Nevro's Motion for Summary Adjudication (Document 343-6) Certified Copy of U.S. Pat. No. 9,327,125, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 40 pages.
Exhibit 7 for Declaration of Eric C. Pai in Support of Nevro's Motion for Summary Adjudication (Document 343-7) Certified Copy of U.S. Pat. No. 9,333,357, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 39 pages.
Exhibit 8 for Declaration of Eric C. Pai in Support of Nevro's Motion for Summary Adjudication (Document 343-8) Certified Copy of U.S. Pat. No. 9,480,842, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 38 pages.
Exhibit 9 for Declaration of Eric C. Pai in Support of Nevro's Motion for Summary Adjudication (Document 343-9) Article by Leonardo Kapural et al., Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 11 pages.
Exhibit 10 for Declaration of Eric C. Pai in Support of Nevro's Motion for Summary Adjudication (Document 343-10) Article by Antonio Foletti et al., Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 15 pages.
Exhibit 11 for Declaration of Eric C. Pai in Support of Nevro's Motion for Summary Adjudication (Document 343-11) Article by Leonardo Kapural et al., Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 12 pages.
Exhibit 12 for Declaration of Eric C. Pai in Support of Nevro's Motion for Summary Adjudication (Document 343-12) Poster by Mark Wallace et al., Boston Scientific Corporation's and Boston

(56) References Cited

OTHER PUBLICATIONS

Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 2 pages.
Exhibit 13 for Declaration of Eric C. Pai in Support of Nevro's Motion for Summary Adjudication (Document 343-13) Summary of Safety and Effectiveness Data (SSED), Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 6 pages.
Exhibit 14 for Declaration of Eric C. Pai in Support of Nevro's Motion for Summary Adjudication (Document 343-14) Nevro—Notes from Las Vegas and Our Survey of 50 US pain docs, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 19 pages.
Exhibit 15 for Declaration of Eric C. Pai in Support of Nevro's Motion for Summary Adjudication (Document 343-15) Apr. 2012 Email between K. Bradley and J. Cassidy, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 5 pages.
Exhibit 16 for Declaration of Eric C. Pai in Support of Nevro's Motion for Summary Adjudication (Document 343-16) Entire Document Sealed, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 1 page.
Exhibit 17 for Declaration of Eric C. Pai in Support of Nevro's Motion for Summary Adjudication (Document 343-17) Entire Document Sealed, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 1 page.
Exhibit 18 for Declaration of Eric C. Pai in Support of Nevro's Motion for Summary Adjudication (Document 343-18) Entire Document Sealed, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 1 page.
Exhibit 19 for Declaration of Eric C. Pai in Support of Nevro's Motion for Summary Adjudication (Document 343-19) Entire Document Sealed, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 1 page.
Exhibit 20 for Declaration of Eric C. Pai in Support of Nevro's Motion for Summary Adjudication (Document 343-20) Redacted Version of Document Sought to be Sealed—Excerpts from May 18, 2018 Deposition of R. Carbunaru, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 12 pages.
Exhibit 21 for Declaration of Eric C. Pai in Support of Nevro's Motion for Summary Adjudication (Document 343-21) Certified Copy of U.S. Pat. No. 8,792,988, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 9 pages.

Exhibit 22 for Declaration of Eric C. Pai in Support of Nevro's Motion for Summary Adjudication (Document 462) Updated Redacted Version of ECF No. 347-10—Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Jul. 30, 2018, 9 pages.
Exhibit 23 for Declaration of Eric C. Pai in Support of Nevro's Motion for Summary Adjudication (Document 463) Updated Redacted Version of ECF No. 347-12, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Jul. 30, 2018, 23 pages.
Exhibit 24 for Declaration of Eric C. Pai in Support of Nevro's Motion for Summary Adjudication (Document 343-24) Redacted Version of Document Sought to Be Sealed—BSC's Supplemental Responses and Objections to Nevro First Set of Interrogatory Request, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 11 pages.
Exhibit 25 for Declaration of Eric C. Pai in Support of Nevro's Motion for Summary Adjudication (Document 464) Updated Redacted Version of ECF No. 347-16—BSC's Second Supplemental Responses and Objections to Nevro First Set of Interrogatory Request, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 12 pages.
Exhibit 26 for Declaration of Eric C. Pai in Support of Nevro's Motion for Summary Adjudication (Document 343-26) Decision Denying Institution of Inter Partes Review 37 CFR § 42.108—IPR2015-01203 U.S. Pat. No. 8,359,102, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 21 pages.
Exhibit 27 for Declaration of Eric C. Pai in Support of Nevro's Motion for Summary Adjudication (Document 343-27) Decision Denying Institution of Inter Partes Review 37 CFR § 42.108—IPR2015-01204 U.S. Pat. No. 8,359,102, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 15 pages.
Exhibit 28 for Declaration of Eric C. Pai in Support of Nevro's Motion for Summary Adjudication (Document 343-28) Certified Copy of U.S. Pat. No. 9,333,357, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 13 pages.
Exhibit 29 for Declaration of Eric C. Pai in Support of Nevro's Motion for Summary Adjudication (Document 343-29) Rebuttal Expert Report and Declaration of Gene Fridman, Ph.D., regarding Claim Construction—Feb. 14, 2018, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 13 pages.
Exhibit 30 for Declaration of Eric C. Pai in Support of Nevro's Motion for Summary Adjudication (Document 343-30) Deposition of Dr. Gene Fridman on Mar. 7, 2018, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 49 pages.
Exhibit 31 for Declaration of Eric C. Pai in Support of Nevro's Motion for Summary Adjudication (Document 343-31) Rebuttal Expert Report and Declaration of Gene Fridman, Ph.D., regarding

(56) References Cited

OTHER PUBLICATIONS

Claim Construction—Jan. 18, 2018, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 12 pages.
Exhibit 32 for Declaration of Eric C. Pai in Support of Nevro's Motion for Summary Adjudication (Document 343-32) Deposition of Kaoru Lee Adair—May 10, 2017, Entire Document Sought to be Sealed, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 1 page.
Exhibit 33 for Declaration of Eric C. Pai in Support of Nevro's Motion for Summary Adjudication (Document 343-33) Expert Report and Declaration of Adam Lipson, M.D., pursuant to Federal Rule of Civil Procedure 26(A)(2)(B) dated Jan. 18, 2017, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 4 pages.
Exhibit 34 for Declaration of Eric C. Pai in Support of Nevro's Motion for Summary Adjudication (Document 343-34) Stedman's Medical Dictionary 27th Edition, definition "paresthesia", Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 4 pages.
Exhibit 35 for Declaration of Eric C. Pai in Support of Nevro's Motion for Summary Adjudication (Document 343-35) Dorland's Illustrated Medical Dictionary, definition "paresthesia", Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 4 pages.
Exhibit 36 for Declaration of Eric C. Pai in Support of Nevro's Motion for Summary Adjudication (Document 343-36) Mosby's Medical Dictionary, definition "paresthesia", Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 5 pages.
Exhibit 37 for Declaration of Eric C. Pai in Support of Nevro's Motion for Summary Adjudication (Document 343-37) National Institute of Neurological Disorders and Stroke—Paresthesia Information Page, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 4 pages.
Exhibit 38 for Declaration of Eric C. Pai in Support of Nevro's Motion for Summary Adjudication (Document 343-38) Videotaped Deposition of Richard T. Mihran, Ph.D. on Mar. 12, 2018, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 10 pages.
Exhibit 39 for Declaration of Eric C. Pai in Support of Nevro's Motion for Summary Adjudication (Document 343-39) Boston Scientific—Precision Spinal Cord Stimulator System with MultiWave Technology Clinician Manual,, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 68 pages.

Exhibit 40 for Declaration of Eric C. Pai in Support of Nevro's Motion for Summary Adjudication (Document 343-40) BSC's Amended and Supplemental Responses and Objections to Nevro's Second Set of Interrogatories (Nos. 9, 10) dated Aug. 24, 2017, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 18 pages.
Exhibit 41 for Declaration of Eric C. Pai in Support of Nevro's Motion for Summary Adjudication (Document 343-41) Rebuttal Expert Report of Richard T. Mihran, Ph.D. dated Feb. 14, 2018, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 23 pages.
Exhibit 42 for Declaration of Eric C. Pai in Support of Nevro's Motion for Summary Adjudication (Document 343-42) Redacted Version of Document Sought to be Sealed—Videotaped Deposition of Nevro Corp. with designated corporate representative Jim Cassidy on May 17, 2017, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 5 pages.
Exhibit 43 for Declaration of Eric C. Pai in Support of Nevro's Motion for Summary Adjudication (Document 343-43) Entire Document Sought to be Sealed—Deposition of Kaoru Lee Adair taken on May 10, 2017, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 1 page.
Exhibit 44 for Declaration of Eric C. Pai in Support of Nevro's Motion for Summary Adjudication (Document 343-44) Entire Document Sought to be Sealed—Deposition of Kaoru Lee Adair taken on May 10, 2017, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 1 page.
Exhibit 45 for Declaration of Eric C. Pai in Support of Nevro's Motion for Summary Adjudication (Document 343-45) Entire Document Sought to be Sealed—Deposition of Kaoru Lee Adair taken on May 10, 2017, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 1 page.
Exhibit 46 for Declaration of Eric C. Pai in Support of Nevro's Motion for Summary Adjudication (Document 343-46) Entire Document Sought to be Sealed—Deposition of Kaoru Lee Adair taken on May 10, 2017, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 1 page.
Exhibit 47 for Declaration of Eric C. Pai in Support of Nevro's Motion for Summary Adjudication (Document 343-47) Entire Document Sought to be Sealed—Deposition of Kaoru Lee Adair taken on May 10, 2017, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 1 page.
Exhibit 48 for Declaration of Eric C. Pai in Support of Nevro's Motion for Summary Adjudication (Document 343-48) Defendant's Identification of 40 Prior Art Grounds for Invalidity dated Dec. 22, 2017, Boston Scientific Corporation's and Boston Scientific Neuromodulation Corporation's Invalidity Contentions, *Nevro Corp.*

(56) References Cited

OTHER PUBLICATIONS v. *Boston Scientific Corporation and Boston Scientific Neuromodulation Corporation*, Case No. 3:16-cv-06830-VC (N.D. Cal.), filed Apr. 12, 2018, 4 pages.
Exhibit 49 for Declaration of Eric C. Pai in Support of Nevro's Motion for Summary Adjudication (Document 343-49) Defendant's Second Amended Preliminary Invalidity Contentions dated Aug. 10, 2017, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 47 pages.
Exhibit 50 for Declaration of Eric C. Pai in Support of Nevro's Motion for Summary Adjudication (Document 343-50) Declaration of Rafael Carbunaru in Support of Boston Scientific's Invalidity Contentions dated Mar. 17, 2017, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 6 pages.
Exhibit 51 for Declaration of Eric C. Pai in Support of Nevro's Motion for Summary Adjudication (Document 343-51) Declaration of Kaoru Lee Adair in Support of Boston Scientific's Motion to Dismiss Nevro's Declaratory Judgment Claims dated Dec. 27, 2016, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 5 pages.
Exhibit 52 for Declaration of Eric C. Pai in Support of Nevro's Motion for Summary Adjudication (Document 343-52) Expert Report of Richard T. Mihran, Ph.D., regarding Invalidity of U.S. Pat. Nos. 8,712,533; 9,327,125; 8,359,102; 9,480,842; 9,333,357; 8,792,988; and 8,768,472 dated Jan. 18, 2018, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 78 pages.
Exhibit 53 for Declaration of Eric C. Pai in Support of Nevro's Motion for Summary Adjudication (Document 343-53) Redacted Version of Document Sought to be Sealed—Rebuttal Expert Report and Declaration of Daniel Lanovaz dated Feb. 14, 2017, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 6 pages.
Exhibit 54 for Declaration of Eric C. Pai in Support of Nevro's Motion for Summary Adjudication (Document 343-54) Certified Copy of U.S. Pat. No. 8,712,533, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 13 pages.
Exhibit 55 for Declaration of Eric C. Pai in Support of Nevro's Motion for Summary Adjudication (Document 343-55) U.S. Patent Application No. 2009/0204173 to Fang et al., Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 33 pages.
Exhibit 56 for Declaration of Eric C. Pai in Support of Nevro's Motion for Summary Adjudication (Document 343-56) Deposition of Konstantinos Alataris dated Nov. 14, 2017, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 34 pages.
Exhibit 57 for Declaration of Eric C. Pai in Support of Nevro's Motion for Summary Adjudication (Document 343-57) Videotaped Deposition of Andre B. Walker dated Nov. 10, 2017, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 26 pages.
Exhibit 58 for Declaration of Eric C. Pai in Support of Nevro's Motion for Summary Adjudication (Document 343-58) Videotaped Deposition of Zi-Ping Fang dated Nov. 2, 2017, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 12 pages.
Exhibit 59 for Declaration of Eric C. Pai in Support of Nevro's Motion for Summary Adjudication (Document 343-59) Videotaped Deposition of Anthony Vincent Caparso dated Nov. 2, 2017, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 8 pages.
Exhibit 60 for Declaration of Eric C. Pai in Support of Nevro's Motion for Summary Adjudication (Document 343-60) Videotaped Deposition of Brian Erickson dated Dec. 15, 2017, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 44 pages.
Exhibit 61 for Declaration of Eric C. Pai in Support of Nevro's Motion for Summary Adjudication (Document 343-61) Deposition of Yougandh Chitre dated Nov. 20, 2017, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 6 pages.
Exhibit 62 for Declaration of Eric C. Pai in Support of Nevro's Motion for Summary Adjudication (Document 343-62) Deposition of Sangsoo Wesley Park dated Nov. 27, 2017, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 8 pages.
Exhibit 63 for Declaration of Eric C. Pai in Support of Nevro's Motion for Summary Adjudication (Document 343-63) Deposition of Jon Parker dated Nov. 16, 2017, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 8 pages.
Exhibit 64 for Declaration of Eric C. Pai in Support of Nevro's Motion for Summary Adjudication (Document 343-64) Videotaped James Thacker dated Dec. 7, 2017 (vol. 1), Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 10 pages.
Exhibit 65 for Declaration of Eric C. Pai in Support of Nevro's Motion for Summary Adjudication (Document 343-65) Sep. 2007 Email between O. Filho and K. Alataris, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 4 pages.

(56) References Cited

OTHER PUBLICATIONS

Exhibit 66 for Declaration of Eric C. Pai in Support of Nevro's Motion for Summary Adjudication (Document 343-66) Redacted Version of Document Sought to be Sealed—BSC's Dec. 1, 2017 Supplemental Responses and Objections to Nevro's Second Set of Interrogatories (Nos. 10 and 14), Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 13 pages.

Exhibit 67 for Declaration of Eric C. Pai in Support of Nevro's Motion for Summary Adjudication (Document 343-67) Certified Copy of U.S. Appl. No. 60/985,353, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 63 pages.

Exhibit 68 for Declaration of Eric C. Pai in Support of Nevro's Motion for Summary Adjudication (Document 343-68) Certified Copy of U.S. Appl. No. 12/264,836, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 67 pages.

Exhibit 69 for Declaration of Eric C. Pai in Support of Nevro's Motion for Summary Adjudication (Document 343-69) Certified Copy File Wrapper for U.S. Appl. No. 12/264,836, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 119 pages.

Exhibit 70 for Declaration of Eric C. Pai in Support of Nevro's Motion for Summary Adjudication (Document 343-70) Request to Add to Originally Named Inventors for U.S. Appl. No. 12/264,836, filed Aug. 13, 2012, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 27 pages.

Exhibit 71 for Declaration of Eric C. Pai in Support of Nevro's Motion for Summary Adjudication (Document 343-71) Poster by Yearwood et al., Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 8 pages.

Exhibit 72 for Declaration of Eric C. Pai in Support of Nevro's Motion for Summary Adjudication (Document 343-72) Case Report by Yearwood et al., Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 3 pages.

Exhibit 73 for Declaration of Eric C. Pai in Support of Nevro's Motion for Summary Adjudication (Document 343-73) Entire Document Sought to be Sealed—Deposition of Rafael Carbunaru taken on Nov. 14, 2017, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 1 page.

Exhibit 74 for Declaration of Eric C. Pai in Support of Nevro's Motion for Summary Adjudication (Document 343-74) Deposition of David Caraway dated Nov. 14, 2017, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 9 pages.

Exhibit 75 for Declaration of Eric C. Pai in Support of Nevro's Motion for Summary Adjudication (Document 343-75) Boston Scientific document, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 5 pages.

Declaration of Carson D. Anderson in Support of Nevro's Administrative Motion to File under Seal Portions of Nevro's Motion for Summary Adjudication and Supporting Documents (Document 348), *Nevro Corp. v. Boston Scientific Corporation and Boston Scientific Neuromodulation Corporation*, Case No. 3:16-cv-06830-VC-MEJ, Apr. 16, 2018, 10 pages.

Exhibit A for Declaration of Carson D. Anderson in Support of Nevro's Administrative Motion to File under Seal Portions of Nevro's Motion for Summary Adjudication and Supporting Documents (Document 347-1) Redacted Version of Document Sought to Be Filed under Seal—Nevro's Notice of Motion, *Nevro Corp. vs. Boston Scientific Corporation and Boston Scientific Neuromodulation Corporation*, Case No. 3:16-cv-06830-VC-MEJ, Apr. 16, 2018, 50 pages.

Exhibit A—Updated—for Declaration of Carson D. Anderson in Support of Nevro's Administrative Motion to File under Seal Portions of Nevro's Motion for Summary Adjudication and Supporting Documents (Document 347-2 / Document 461) Redacted Version of Document Sought to Be Filed under Seal—Nevro's Motion for Summary Adjudication, *Nevro Corp. vs. Boston Scientific Corporation and Boston Scientific Neuromodulation Corporation*, Case No. 3:16-cv-06830-VC-MEJ, Jul. 30, 2018, 50 pages.

Exhibit B for Declaration of Carson D. Anderson in Support of Nevro's Administrative Motion to File under Seal Portions of Nevro's Motion for Summary Adjudication and Supporting Documents (Document 347-3) Redacted Version of Document Sought to Be Filed under Seal—Videotaped Deposition of Rafael Carbunaru, Ph.D., taken Nov. 15, 2017,*Nevro Corp. vs. Boston Scientific Corporation and Boston Scientific Neuromodulation Corporation*, Case No. 3:16-cv-06830-VC-MEJ, filed Apr. 16, 2018, 46 pages.

Exhibit C for Declaration of Carson D. Anderson in Support of Nevro's Administrative Motion to File under Seal Portions of Nevro's Motion for Summary Adjudication and Supporting Documents (Document 347-5) Boston Scientific Neuromodulation -—Sprint High Rate—Product Opportunity Proposal, *Nevro Corp. vs. Boston Scientific Corporation and Boston Scientific Neuromodulation Corporation*, Case No. 3:16-cv-06830-VC-MEJ, filed Apr. 16, 2018, 14 pages.

Exhibit D for Declaration of Carson D. Anderson in Support of Nevro's Administrative Motion to File under Seal Portions of Nevro's Motion for Summary Adjudication and Supporting Documents (Document 347-7) Redacted Version of Document Sought to be Filed under Seal—Boston Scientific Neuromodulation—Sprint High Rate—Project Authorization Review, *Nevro Corp. vs. Boston Scientific Corporation and Boston Scientific Neuromodulation Corporation*, Case No. 3:16-cv-06830-VC-MEJ, filed Apr. 16, 2018, 7 pages.

Exhibit E for Declaration of Carson D. Anderson in Support of Nevro's Administrative Motion to File under Seal Portions of Nevro's Motion for Summary Adjudication and Supporting Documents (Document 347-9) Redacted Version of Document Sought to be Filed under Seal—Videotaped Deposition of Kaoru Lee Adair, *Nevro Corp. vs. Boston Scientific Corporation and Boston Scientific Neuromodulation Corporation*, Case No. 3:16-cv-06830-VC-MEJ, filed Apr. 16, 2018, 12 pages.

Exhibit E—Updated —for Declaration of Carson D. Anderson in Support of Nevro's Administrative Motion to File under Seal Portions of Nevro's Motion for Summary Adjudication and Supporting Documents (Document 347-10) Redacted Version of Document Sought to be Filed under Seal—Videotaped Deposition of Kaoru Lee Adair, taken Nov. 17, 2017, *Nevro Corp. vs. Boston Scientific Corporation and Boston Scientific Neuromodulation Corporation*, Case No. 3:16-cv-06830-VC-MEJ, filed Apr. 16, 2018, 12 pages.

Exhibit F for Declaration of Carson D. Anderson in Support of Nevro's Administrative Motion to File under Seal Portions of

(56) References Cited

OTHER PUBLICATIONS

Nevro's Motion for Summary Adjudication and Supporting Documents (Document 347-11) Redacted Version of Document Sought to be Filed under Seal - Videotaped Deposition of Kaoru Lee Adair, taken May 10, 2017, *Nevro Corp. vs. Boston Scientific Corporation and Boston Scientific Neuromodulation Corporation*, Case No. 3:16-cv-06830-VC-MEJ, filed Apr. 16, 2018, 23 pages.
Exhibit F—Updated—for Declaration of Carson D. Anderson in Support of Nevro's Administrative Motion to File under Seal Portions of Nevro's Motion for Summary Adjudication and Supporting Documents (Document 347-12) Redacted Version of Document Sought to be Filed under Seal—Videotaped Deposition of Kaoru Lee Adair, taken May 10, 2017, *Nevro Corp. vs. Boston Scientific Corporation and Boston Scientific Neuromodulation Corporation*, Case No. 3:16-cv-06830-VC-MEJ, filed Apr. 16, 2018, 23 pages.
Exhibit G for Declaration of Carson D. Anderson in Support of Nevro's Administrative Motion to File under Seal Portions of Nevro's Motion for Summary Adjudication and Supporting Documents (Document 347-13) BSC's Supplemental Responses and Objections to Nevro's First Set of Interrogatory Requests (1-8), *Nevro Corp. vs. Boston Scientific Corporation and Boston Scientific Neuromodulation Corporation*, Case No. 3:16-cv-06830-VC-MEJ, filed Apr. 16, 2018, 12 pages.
Exhibit H for Declaration of Carson D. Anderson in Support of Nevro's Administrative Motion to File under Seal Portions of Nevro's Motion for Summary Adjudication and Supporting Documents (Document 347-15) Redacted Version of Document Sought to be Filed under Seal—BSC's Second Supplemental Responses and Objections to Nevro's First Set of Interrogatory Requests (1-8), *Nevro Corp. vs. Boston Scientific Corporation and Boston Scientific Neuromodulation Corporation*, Case No. 3:16-cv-06830-VC-MEJ, filed Apr. 16, 2018, 12 pages.
Exhibit H—Updated—for Declaration of Carson D. Anderson in Support of Nevro's Administrative Motion to File under Seal Portions of Nevro's Motion for Summary Adjudication and Supporting Documents (Document 347-16) Updated Redacted Version of Document Sought to be Filed under Seal—BSC's Second Supplemental Responses and Objections to Nevro's First Set of Interrogatory Requests (1-8), *Nevro Corp. vs. Boston Scientific Corporation and Boston Scientific Neuromodulation Corporation*, Case No. 3:16-cv-06830-VC-MEJ, filed Apr. 16, 2018, 12 pages.
Exhibit I for Declaration of Carson D. Anderson in Support of Nevro's Administrative Motion to File under Seal Portions of Nevro's Motion for Summary Adjudication and Supporting Documents (Document 347-17) Redacted Version of Document Sought to be Filed under Seal—Rebuttal Expert Report of Richard T. Mihran, Ph.D., *Nevro Corp. vs. Boston Scientific Corporation and Boston Scientific Neuromodulation Corporation*, Case No. 3:16-cv-06830-VC-MEJ, filed Apr. 16, 2018, 24 pages.
Exhibit J for Declaration of Carson D. Anderson in Support of Nevro's Administrative Motion to File under Seal Portions of Nevro's Motion for Summary Adjudication and Supporting Documents (Document 347-19) Redacted Version of Document Sought to be Filed under Seal—Oct. 24, 2016 Boston Scientific Letter to U.S. Food and Drug Administration, *Nevro Corp. vs. Boston Scientific Corporation and Boston Scientific Neuromodulation Corporation*, Case No. 3:16-cv-06830-VC-MEJ, filed Apr. 16, 2018, 5 pages.
Exhibit K for Declaration of Carson D. Anderson in Support of Nevro's Administrative Motion to File under Seal Portions of Nevro's Motion for Summary Adjudication and Supporting Documents (Document 347-21) Redacted Version of Document Sought to be Filed under Seal—Rebuttal Expert Report and Declaration of Daniel Lanovaz dated Feb. 14, 2017, *Nevro Corp. vs. Boston Scientific Corporation and Boston Scientific Neuromodulation Corporation*, Case No. 3:16-cv-06830-VC-MEJ, filed Apr. 16, 2018, 7 pages.
Exhibit L for Declaration of Carson D. Anderson in Support of Nevro's Administrative Motion to File under Seal Portions of Nevro's Motion for Summary Adjudication and Supporting Documents (Document 347-23) Redacted Version of Document Sought to be Filed under Seal—Declaration of Ben Pless in Support of Nevro's Motion of Summary Adjudication dated Apr. 12, 2018, *Nevro Corp. vs. Boston Scientific Corporation and Boston Scientific Neuromodulation Corporation*, Case No. 3:16-cv-06830-VC-MEJ, filed Apr. 16, 2018, 64 pages.
Exhibit L—Updated—for Declaration of Carson D. Anderson in Support of Nevro's Administrative Motion to File under Seal Portions of Nevro's Motion for Summary Adjudication and Supporting Documents (Document 347-24) Updated Redacted Version of Document Sought to be Filed under Seal—Declaration of Ben Pless in Support of Nevro's Motion of Summary Adjudication dated Apr. 12, 2018, *Nevro Corp. vs. Boston Scientific Corporation and Boston Scientific Neuromodulation Corporation*, Case No. 3:16-cv-06830-VC-MEJ, filed Apr. 16, 2018, 64 pages.
Declaration of Rafael Carbunaru in Support of Nevro's Administrative Motion to File under Seal Portions of Nevro's Motion for Summary Adjudication and Supporting Documents (Document 347-25), *Nevro Corp. vs. Boston Scientific Corporation and Boston Scientific Neuromodulation Corporation*, Case No. 3:16-cv-06830-VC-MEJ, filed Apr. 16, 2018, 13 pages.
[Proposed] Order Granting Administrative Motion to File under Seal Portions of Nevro's Administrative Motion to File under Seal Portions of Nevro's Motion for Summary Adjudication and Supporting Documents (ECF No. 341) (Document 347-26), *Nevro Corp. vs. Boston Scientific Corporation and Boston Scientific Neuromodulation Corporation*, Case No. 3:16-cv-06830-VC-MEJ, filed Apr. 16, 2018, 5 pages.
Boston Scientific's Responsive Claim Construction Brief, Opposition to Nevro's Motion for Summary Adjudication and Supporting Documents (Document 466), Updated Redacted Version of ECF No. 357-4, *Nevro Corp. vs. Boston Scientific Corporation and Boston Scientific Neuromodulation Corporation*, Case No. 3:16-cv-06830-VC-MEJ, filed Jul. 30, 2018, 61 pages.
Expert Report and Declaration of Gene Fridman, Ph.D., regarding Claim Construction (Document 358-1), *Nevro Corp. vs. Boston Scientific Corporation and Boston Scientific Neuromodulation Corporation*, Case No. 3:16-cv-06830-VC-MEJ, filed Apr. 26, 2018, 18 pages.
Rebuttal Expert Report and Declaration of Gene Fridman, Ph.D., regarding Claim Construction (Document 358-2), *Nevro Corp. vs. Boston Scientific Corporation and Boston Scientific Neuromodulation Corporation*, Case No. 3:16-cv-06830-VC-MEJ, filed Apr. 26, 2018, 11 pages.
Declaration of Richard T. Mihran, Ph.D., regarding Claim Construction Brief (Document 358-3), *Nevro Corp. vs. Boston Scientific Corporation and Boston Scientific Neuromodulation Corporation*, Case No. 3:16-cv-06830-VC-MEJ, filed Apr. 26, 2018, 2 pages.
Exhibit A for Declaration of Richard T. Mihran, Ph.D., regarding Claim Construction Brief (Document 358-4), Expert Report of Richard T. Mihran, Ph.D. regarding Invalidity of U.S. Pat. Nos. 8,712,533; 9,327,125; 8,359,102; 9,480,842; 9,333,357; 8,792,988; and 8,768,472, *Nevro Corp. vs. Boston Scientific Corporation and Boston Scientific Neuromodulation Corporation*, Case No. 3:16-cv-06830-VC-MEJ, filed Apr. 26, 2018, 129 pages.
Exhibit B Declaration of Richard T. Mihran, Ph.D., regarding Claim Construction Brief (Document 358-5), Redacted Version of Document Sought to be Filed under Seal—Rebuttal Expert Report of Richard T. Mihran, Ph.D., *Nevro Corp. vs. Boston Scientific Corporation and Boston Scientific Neuromodulation Corporation*, Case No. 3:16-cv-06830-VC-MEJ, filed Apr. 26, 2018, 79 pages.
Declaration of Clara W. Wang in Support of Boston Scientific's Responsive regarding Claim Construction Brief; Opposition to Nevro's Motion for Summary Judgement and Opening Motion for Summary Judgement (Document 358-6), *Nevro Corp. vs. Boston Scientific Corporation and Boston Scientific Neuromodulation Corporation*, Case No. 3:16-cv-06830-VC-MEJ, filed Apr. 26, 2018, 8 pages.
Exhibit 1 for Declaration of Clara W. Wang in Support of Boston Scientific's Responsive regarding Claim Construction Brief; Opposition to Nevro's Motion for Summary Judgement and Opening Motion for Summary Judgement (Document 358-7), Sep. 2005

(56) References Cited

OTHER PUBLICATIONS

Email between K. Bradley and M. Moffitt, *Nevro Corp. vs. Boston Scientific Corporation and Boston Scientific Neuromodulation Corporation*, Case No. 3:16-cv-06830-VC-MEJ, filed Apr. 26, 2018, 2 pages.
Exhibit 2 for Declaration of Clara W. Wang in Support of Boston Scientific's Responsive regarding Claim Construction Brief; Opposition to Nevro's Motion for Summary Judgement and Opening Motion for Summary Judgement (Document 358-8), Filed under Seal—Document NEVRO_BSXCA0165810-52, *Nevro Corp. vs. Boston Scientific Corporation and Boston Scientific Neuromodulation Corporation*, Case No. 3:16-cv-06830-VC-MEJ, filed Apr. 26, 2018, 1 page.
Exhibit 3 for Declaration of Clara W. Wang in Support of Boston Scientific's Responsive regarding Claim Construction Brief; Opposition to Nevro's Motion for Summary Judgement and Opening Motion for Summary Judgement (Document 358-9), Filed under Seal—Document NEVRO_BSXCA0389050-100, *Nevro Corp. vs. Boston Scientific Corporation and Boston Scientific Neuromodulation Corporation*, Case No. 3:16-cv-06830-VC-MEJ, filed Apr. 26, 2018, 1 page.
Exhibit 4 for Declaration of Clara W. Wang in Support of Boston Scientific's Responsive regarding Claim Construction Brief; Opposition to Nevro's Motion for Summary Judgement and Opening Motion for Summary Judgement (Document 358-10), Summary of Safety and Effectiveness Data (SSED), *Nevro Corp. vs. Boston Scientific Corporation and Boston Scientific Neuromodulation Corporation*, Case No. 3:16-cv-06830-VC-MEJ, filed Apr. 26, 2018, 57 pages.
Exhibit 5 for Declaration of Clara W. Wang in Support of Boston Scientific's Responsive regarding Claim Construction Brief; Opposition to Nevro's Motion for Summary Judgement and Opening Motion for Summary Judgement (Document 358-11), Article by Andres et al., *Nevro Corp. vs. Boston Scientific Corporation and Boston Scientific Neuromodulation Corporation*, Case No. 3:16-cv-06830-VC-MEJ, filed Apr. 26, 2018, 22 pages.
Exhibit 6 for Declaration of Clara W. Wang in Support of Boston Scientific's Responsive regarding Claim Construction Brief; Opposition to Nevro's Motion for Summary Judgement and Opening Motion for Summary Judgement (Document 358-12), Article by Thomson et al., *Nevro Corp. vs. Boston Scientific Corporation and Boston Scientific Neuromodulation Corporation*, Case No. 3:16-cv-06830-VC-MEJ, filed Apr. 26, 2018, 11 pages.
Exhibit 7 for Declaration of Clara W. Wang in Support of Boston Scientific's Responsive regarding Claim Construction Brief; Opposition to Nevro's Motion for Summary Judgement and Opening Motion for Summary Judgement (Document 358-13), Filed under Seal—Document labeled NEVRO_BSXCA0053540-89, *Nevro Corp. vs. Boston Scientific Corporation and Boston Scientific Neuromodulation Corporation*, Case No. 3:16-cv-06830-VC-MEJ, filed Apr. 26, 2018, 1 page.
Exhibit 8 for Declaration of Clara W. Wang in Support of Boston Scientific's Responsive regarding Claim Construction Brief; Opposition to Nevro's Motion for Summary Judgement and Opening Motion for Summary Judgement (Document 358-14), Filed under Seal—Document labeled NEVRO_BSXCA0055766-70, *Nevro Corp. vs. Boston Scientific Corporation and Boston Scientific Neuromodulation Corporation*, Case No. 3:16-cv-06830-VC-MEJ, filed Apr. 26, 2018, 1 page.
Exhibit 9 for Declaration of Clara W. Wang in Support of Boston Scientific's Responsive regarding Claim Construction Brief; Opposition to Nevro's Motion for Summary Judgement and Opening Motion for Summary Judgement (Document 358-15), Filed under Seal—Document labeled NEVRO_BSXCA0049348-69, *Nevro Corp. vs. Boston Scientific Corporation and Boston Scientific Neuromodulation Corporation*, Case No. 3:16-cv-06830-VC-MEJ, filed Apr. 26, 2018, 1 page.
Exhibit 10 for Declaration of Clara W. Wang in Support of Boston Scientific's Responsive regarding Claim Construction Brief; Opposition to Nevro's Motion for Summary Judgement and Opening Motion for Summary Judgement (Document 358-16), Videotaped Deposition of Rafael Carbunaru, Ph.D., taken on Nov. 15, 2017, *Nevro Corp. vs. Boston Scientific Corporation and Boston Scientific Neuromodulation Corporation*, Case No. 3:16-cv-06830-VC-MEJ, filed Apr. 26, 2018, 9 pages.
Exhibit 11 for Declaration of Clara W. Wang in Support of Boston Scientific's Responsive regarding Claim Construction Brief; Opposition to Nevro's Motion for Summary Judgement and Opening Motion for Summary Judgement (Document 358-17), Redacted Version of Document Sought to be Filed under Sealed—Videotaped Deposition of Jim Cassidy, taken on Nov. 29, 2017, *Nevro Corp. vs. Boston Scientific Corporation and Boston Scientific Neuromodulation Corporation*, Case No. 3:16-cv-06830-VC-MEJ, filed Apr. 26, 2018, 9 pages.
Exhibit 12 for Declaration of Clara W. Wang in Support of Boston Scientific's Responsive regarding Claim Construction Brief; Opposition to Nevro's Motion for Summary Judgement and Opening Motion for Summary Judgement (Document 467), Filed under Sealed—Videotaped Deposition of Kaoru Lee Adair, taken on Nov. 17, 2017, *Nevro Corp. vs. Boston Scientific Corporation and Boston Scientific Neuromodulation Corporation*, Case No. 3:16-cv-06830-VC-MEJ, filed Apr. 26, 2018, 10 pages.
Exhibit 13 for Declaration of Clara W. Wang in Support of Boston Scientific's Responsive regarding Claim Construction Brief; Opposition to Nevro's Motion for Summary Judgement and Opening Motion for Summary Judgement (Document 358-19), Redacted Version of Document Sought to be Filed under Seal—Videotaped Deposition of Jim Cassidy, taken on Nov. 30, 2017, *Nevro Corp. vs. Boston Scientific Corporation and Boston Scientific Neuromodulation Corporation*, Case No. 3:16-cv-06830-VC-MEJ, filed Apr. 26, 2018, 10 pages.
Exhibit 14 for Declaration of Clara W. Wang in Support of Boston Scientific's Responsive regarding Claim Construction Brief; Opposition to Nevro's Motion for Summary Judgement and Opening Motion for Summary Judgement (Document 358-20), Apr. 2018 Email between K. Carter and MoFo-NevroBSX, taken on Nov. 30, 2017, *Nevro Corp. vs. Boston Scientific Corporation and Boston Scientific Neuromodulation Corporation*, Case No. 3:16-cv-06830-VC-MEJ, filed Apr. 26, 2018, 2 pages.
Exhibit 15 for Declaration of Clara W. Wang in Support of Boston Scientific's Responsive regarding Claim Construction Brief; Opposition to Nevro's Motion for Summary Judgement and Opening Motion for Summary Judgement (Document 358-21), Boston Scientific Advancing Science for Life—Technical Sales Training, *Nevro Corp. vs. Boston Scientific Corporation and Boston Scientific Neuromodulation Corporation*, Case No. 3:16-cv-06830-VC-MEJ, filed Apr. 26, 2018, 3 pages.
Exhibit 16 for Declaration of Clara W. Wang in Support of Boston Scientific's Responsive regarding Claim Construction Brief; Opposition to Nevro's Motion for Summary Judgement and Opening Motion for Summary Judgement (Document 358-22), Product Specification for Ninja System, *Nevro Corp. vs. Boston Scientific Corporation and Boston Scientific Neuromodulation Corporation*, Case No. 3:16-cv-06830-VC-MEJ, filed Apr. 26, 2018, 3 pages.
Exhibit 17 for Declaration of Clara W. Wang in Support of Boston Scientific's Responsive regarding Claim Construction Brief; Opposition to Nevro's Motion for Summary Judgement (Document 358-23), Deposition of Ben Pless, taken on Apr. 10, 2018, *Nevro Corp. vs. Boston Scientific Corporation and Boston Scientific Neuromodulation Corporation*, Case No. 3:16-cv-06830-VC-MEJ, filed Apr. 26, 2018, 3 pages.
Exhibit 18 for Declaration of Clara W. Wang in Support of Boston Scientific's Responsive regarding Claim Construction Brief; Opposition to Nevro's Motion for Summary Judgement and Opening Motion for Summary Judgement (Document 358-24), Merriam-Webster's Collegiate Dictionary, *Nevro Corp. vs. Boston Scientific Corporation and Boston Scientific Neuromodulation Corporation*, Case No. 3:16-cv-06830-VC-MEJ, filed Apr. 26, 2018, 5 pages.
Exhibit 19 for Declaration of Clara W. Wang in Support of Boston Scientific's Responsive regarding Claim Construction Brief; Opposition to Nevro's Motion for Summary Judgement and Opening Motion for Summary Judgement (Document 358-25), Merriam-Webster's Collegiate Dictionary, *Nevro Corp. vs. Boston Scientific*

(56) References Cited

OTHER PUBLICATIONS

*Corporation and Boston Scientific Neuromodulation Corporation,* Case No. 3:16-cv-06830-VC-MEJ, filed Apr. 26, 2018, 5 pages.
Exhibit 20 for Declaration of Clara W. Wang in Support of Boston Scientific's Responsive regarding Claim Construction Brief; Opposition to Nevro's Motion for Summary Judgement and Opening Motion for Summary Judgement (Document 358-26), Concise Oxford Dictionary, *Nevro Corp. vs. Boston Scientific Corporation and Boston Scientific Neuromodulation Corporation,* Case No. 3:16-cv-06830-VC-MEJ, filed Apr. 26, 2018, 5 pages.
Exhibit 21 for Declaration of Clara W. Wang in Support of Boston Scientific's Responsive regarding Claim Construction Brief; Opposition to Nevro's Motion for Summary Judgement and Opening Motion for Summary Judgement (Document 358-27), Final Office Action for U.S. Appl. No. 15/134,285, issued Nov. 28, 2017, *Nevro Corp. vs. Boston Scientific Corporation and Boston Scientific Neuromodulation Corporation,* Case No. 3:16-cv-06830-VC-MEJ, filed Apr. 26, 2018, 22 pages.
Exhibit 22 for Declaration of Clara W. Wang in Support of Boston Scientific's Responsive regarding Claim Construction Brief; Opposition to Nevro's Motion for Summary Judgement and Opening Motion for Summary Judgement (Document 358-28), U.S. Pat. No. 8,355,797 by Caparso et al., *Nevro Corp. vs. Boston Scientific Corporation and Boston Scientific Neuromodulation Corporation,* Case No. 3:16-cv-06830-VC-MEJ, filed Apr. 26, 2018, 21 pages.
Exhibit 23 for Declaration of Clara W. Wang in Support of Boston Scientific's Responsive regarding Claim Construction Brief; Opposition to Nevro's Motion for Summary Judgement and Opening Motion for Summary Judgement (Document 358-29), Redacted Version of the Document Sought to be Filed under Seal—Deposition of Jon Parker dated Nov. 16, 2017, *Nevro Corp. vs. Boston Scientific Corporation and Boston Scientific Neuromodulation Corporation,* Case No. 3:16-cv-06830-VC-MEJ, filed Apr. 26, 2018, 12 pages.
Exhibit 24 for Declaration of Clara W. Wang in Support of Boston Scientific's Responsive regarding Claim Construction Brief; Opposition to Nevro's Motion for Summary Judgement and Opening Motion for Summary Judgement (Document 358-30), Redacted Version of the Document Sought to be Filed under Seal—Corrected Rebuttal Expert Report of Ben Plesss regarding Validity dated Mar. 5, 2018, *Nevro Corp. vs. Boston Scientific Corporation and Boston Scientific Neuromodulation Corporation,* Case No. 3:16-cv-06830-VC-MEJ, filed Apr. 26, 2018, 55 pages.
Exhibit 25 for Declaration of Clara W. Wang in Support of Boston Scientific's Responsive regarding Claim Construction Brief; Opposition to Nevro's Motion for Summary Judgement and Opening Motion for Summary Judgement (Document 358-31), Deposition of Dr. Gene Fridman dated Mar. 7, 2018, *Nevro Corp. vs. Boston Scientific Corporation and Boston Scientific Neuromodulation Corporation,* Case No. 3:16-cv-06830-VC-MEJ, filed Apr. 26, 2018, 14 pages.
Exhibit 26 for Declaration of Clara W. Wang in Support of Boston Scientific's Responsive regarding Claim Construction Brief; Opposition to Nevro's Motion for Summary Judgement and Opening Motion for Summary Judgement (Document 358-32), Redacted Version of Document Sought to be Filed under Seal—Opening Expert Report of Ben Pless regarding Infringement dated Jan. 18, 2018, *Nevro Corp. vs. Boston Scientific Corporation and Boston Scientific Neuromodulation Corporation,* Case No. 3:16-cv-06830-VC-MEJ, filed Apr. 26, 2018, 23 pages.
Exhibit 27 for Declaration of Clara W. Wang in Support of Boston Scientific's Responsive regarding Claim Construction Brief; Opposition to Nevro's Motion for Summary Judgement and Opening Motion for Summary Judgement (Document 358-33), U.S. Patent Application Publication No. 2017/0050021 to Cosman Sr., *Nevro Corp. vs. Boston Scientific Corporation and Boston Scientific Neuromodulation Corporation,* Case No. 3:16-cv-06830-VC-MEJ, filed Apr. 26, 2018, 32 pages.
Exhibit 28 for Declaration of Clara W. Wang in Support of Boston Scientific's Responsive regarding Claim Construction Brief; Opposition to Nevro's Motion for Summary Judgement and Opening Motion for Summary Judgement (Document 358-34), Expert Report of William S. Rosenberg, MD, FAANS, dated Jan. 18, 2018, *Nevro Corp. vs. Boston Scientific Corporation and Boston Scientific Neuromodulation Corporation,* Case No. 3:16-cv-06830-VC-MEJ, filed Apr. 26, 2018, 4 pages.
Exhibit 29 for Declaration of Clara W. Wang in Support of Boston Scientific's Responsive regarding Claim Construction Brief; Opposition to Nevro's Motion for Summary Judgement and Opening Motion for Summary Judgement (Document 358-35), Declaration of David Caraway, M.D. Ph.D., dated Feb. 16, 2016, *Nevro Corp. vs. Boston Scientific Corporation and Boston Scientific Neuromodulation Corporation,* Case No. 3:16-cv-06830-VC-MEJ, filed Apr. 26, 2018, 8 pages.
Exhibit 30 for Declaration of Clara W. Wang in Support of Boston Scientific's Responsive regarding Claim Construction Brief; Opposition to Nevro's Motion for Summary Judgement and Opening Motion for Summary Judgement (Document 358-36), Filed under Seal—Document NEVRO_BSXCA0073295-300, *Nevro Corp. vs. Boston Scientific Corporation and Boston Scientific Neuromodulation Corporation,* Case No. 3:16-cv-06830-VC-MEJ, filed Apr. 26, 2018, 1 page.
Exhibit 31 for Declaration of Clara W. Wang in Support of Boston Scientific's Responsive regarding Claim Construction Brief; Opposition to Nevro's Motion for Summary Judgement and Opening Motion for Summary Judgement (Document 358-37), Article by Alexander J.R. Macdonald et al., *Nevro Corp. vs. Boston Scientific Corporation and Boston Scientific Neuromodulation Corporation,* Case No. 3:16-cv-06830-VC-MEJ, filed Apr. 26, 2018, 10 pages.
Exhibit 32 for Declaration of Clara W. Wang in Support of Boston Scientific's Responsive regarding Claim Construction Brief; Opposition to Nevro's Motion for Summary Judgement and Opening Motion for Summary Judgement (Document 358-38), U.S. Pat. No. 5,776,170 to MacDonald et al., *Nevro Corp. vs. Boston Scientific Corporation and Boston Scientific Neuromodulation Corporation,* Case No. 3:16-cv-06830-VC-MEJ, filed Apr. 26, 2018, 12 pages.
Exhibit 33 for Declaration of Clara W. Wang in Support of Boston Scientific's Responsive regarding Claim Construction Brief; Opposition to Nevro's Motion for Summary Judgement and Opening Motion for Summary Judgement (Document 358-39), File History for U.S. Appl. No. 14/525, 134, issued Mar. 12, 2015, *Nevro Corp. vs. Boston Scientific Corporation and Boston Scientific Neuromodulation Corporation,* Case No. 3:16-cv-06830-VC-MEJ, filed Apr. 26, 2018, 34 pages.
Exhibit 34 for Declaration of Clara W. Wang in Support of Boston Scientific's Responsive regarding Claim Construction Brief; Opposition to Nevro's Motion for Summary Judgement and Opening Motion for Summary Judgement (Document 358-40), Filed under Seal—Document NEVRO_BSXCA0108347-8, *Nevro Corp. vs. Boston Scientific Corporation and Boston Scientific Neuromodulation Corporation,* Case No. 3:16-cv-06830-VC-MEJ, filed Apr. 26, 2018, 1 page.
Exhibit 35 for Declaration of Clara W. Wang in Support of Boston Scientific's Responsive regarding Claim Construction Brief; Opposition to Nevro's Motion for Summary Judgement and Opening Motion for Summary Judgement (Document 358-41), Non-Final Office Action for U.S. Appl. No. 14/503,259, issued Dec. 3, 2015, *Nevro Corp. vs. Boston Scientific Corporation and Boston Scientific Neuromodulation Corporation,* Case No. 3:16-cv-06830-VC-MEJ, filed Apr. 26, 2018, 11 pages.
Exhibit 36 for Declaration of Clara W. Wang in Support of Boston Scientific's Responsive regarding Claim Construction Brief; Opposition to Nevro's Motion for Summary Judgement and Opening Motion for Summary Judgement (Document 358-42), Documents from File History for U.S. Appl. No. 14/261,369, *Nevro Corp. vs. Boston Scientific Corporation and Boston Scientific Neuromodulation Corporation,* Case No. 3:16-cv-06830-VC-MEJ, filed Apr. 26, 2018, 59 pages.
Exhibit 37 for Declaration of Clara W. Wang in Support of Boston Scientific's Responsive regarding Claim Construction Brief; Opposition to Nevro's Motion for Summary Judgement and Opening Motion for Summary Judgement (Document 358-43), Final Office Action for U.S. Appl. No. 15/134,285, issued Nov. 28, 2017, *Nevro*

(56) References Cited

OTHER PUBLICATIONS

*Corp.* vs. *Boston Scientific Corporation and Boston Scientific Neuromodulation Corporation*, Case No. 3:16-cv-06830-VC-MEJ, filed Apr. 26, 2018, 22 pages.
Exhibit 38 for Declaration of Clara W. Wang in Support of Boston Scientific's Responsive regarding Claim Construction Brief; Opposition to Nevro's Motion for Summary Judgement and Opening Motion for Summary Judgement (Document 358-44), U.S. National Library of Medicine—ClinicalTrials.gov, *Nevro Corp.* vs. *Boston Scientific Corporation and Boston Scientific Neuromodulation Corporation*, Case No. 3:16-cv-06830-VC-MEJ, filed Apr. 26, 2018, 6 pages.
Exhibit 39 for Declaration of Clara W. Wang in Support of Boston Scientific's Responsive regarding Claim Construction Brief; Opposition to Nevro's Motion for Summary Judgement and Opening Motion for Summary Judgement (Document 358-45), Redacted Version of Document Sought to be Filed under Seal—Jan. 23, 2014 Correspondence to Boston Scientific Corporation, *Nevro Corp.* vs. *Boston Scientific Corporation and Boston Scientific Neuromodulation Corporation*, Case No. 3:16-cv-06830-VC-MEJ, filed Apr. 26, 2018, 10 pages.
Exhibit 40 for Declaration of Clara W. Wang in Support of Boston Scientific's Responsive regarding Claim Construction Brief; Opposition to Nevro's Motion for Summary Judgement and Opening Motion for Summary Judgement (Document 358-46), Redacted Version of Document Sought to be Filed under Seal—Nov. 23, 2016 Email and Correspondence to Kaoru Adair, *Nevro Corp.* vs. *Boston Scientific Corporation and Boston Scientific Neuromodulation Corporation*, Case No. 3:16-cv-06830-VC-MEJ, filed Apr. 26, 2018, 8 pages.
Exhibit 41 for Declaration of Clara W. Wang in Support of Boston Scientific's Responsive regarding Claim Construction Brief; Opposition to Nevro's Motion for Summary Judgement and Opening Motion for Summary Judgement (Document 358-47), Boston Scientific—Investigational Device Exemption (IDE) Application, submission date Feb. 21, 2013, *Nevro Corp.* vs. *Boston Scientific Corporation and Boston Scientific Neuromodulation Corporation*, Case No. 3:16-cv-06830-VC-MEJ, filed Apr. 26, 2018, 5 pages.
Exhibit 42 for Declaration of Clara W. Wang in Support of Boston Scientific's Responsive regarding Claim Construction Brief; Opposition to Nevro's Motion for Summary Judgement and Opening Motion for Summary Judgement (Document 358-48), Redacted Version of Document Sought to be Filed under Seal—Boston Scientific—A Randomized Controlled Study to Evaluate the Safety and Effectiveness of the Precision Spinal Cord Stimulator System Adapted for High-Rate Spinal Cord Stimulation, *Nevro Corp.* vs. *Boston Scientific Corporation and Boston Scientific Neuromodulation Corporation*, Case No. 3:16-cv-06830-VC-MEJ, filed Apr. 26, 2018, 5 pages.
Exhibit 43 for Declaration of Clara W. Wang in Support of Boston Scientific's Responsive regarding Claim Construction Brief; Opposition to Nevro's Motion for Summary Judgement and Opening Motion for Summary Judgement (Document 358-49), World Medical Association —WMA Declaration of Helsinki—Ethical Principles for Medical Research Involving Human Subjects, *Nevro Corp.* vs. *Boston Scientific Corporation and Boston Scientific Neuromodulation Corporation*, Case No. 3:16-cv-06830-VC-MEJ, filed Apr. 26, 2018, 3 pages.
Exhibit 44 for Declaration of Clara W. Wang in Support of Boston Scientific's Responsive regarding Claim Construction Brief; Opposition to Nevro's Motion for Summary Judgement and Opening Motion for Summary Judgement (Document 358-50), U.S. Patent Application Publication No. 2007/0073354 to Knudson et al., *Nevro Corp.* vs. *Boston Scientific Corporation and Boston Scientific Neuromodulation Corporation*, Case No. 3:16-cv-06830-VC-MEJ, filed Apr. 26, 2018, 15 pages.
Exhibit 45 for Declaration of Clara W. Wang in Support of Boston Scientific's Responsive regarding Claim Construction Brief; Opposition to Nevro's Motion for Summary Judgement and Opening Motion for Summary Judgement (Document 358-51), U.S. Patent Application Publication No. 2007/0060954 to Cameron et al., *Nevro Corp.* vs. *Boston Scientific Corporation and Boston Scientific Neuromodulation Corporation*, Case No. 3:16-cv-06830-VC-MEJ, filed Apr. 26, 2018, 21 pages.
Exhibit 46 for Declaration of Clara W. Wang in Support of Boston Scientific's Responsive regarding Claim Construction Brief; Opposition to Nevro's Motion for Summary Judgement and Opening Motion for Summary Judgement (Document 358-52), Documents from File History for U.S. Appl. No. 12/765,747, *Nevro Corp.* vs. *Boston Scientific Corporation and Boston Scientific Neuromodulation Corporation*, Case No. 3:16-cv-06830-VC-MEJ, filed Apr. 26, 2018, 57 pages.
Exhibit 47 for Declaration of Clara W. Wang in Support of Boston Scientific's Responsive regarding Claim Construction Brief; Opposition to Nevro's Motion for Summary Judgement and Opening Motion for Summary Judgement (Document 358-53), Response to Final Office Action for U.S. Appl. No. 14/292,671, filed Jan. 17, 2017, *Nevro Corp.* vs. *Boston Scientific Corporation and Boston Scientific Neuromodulation Corporation*, ase No. 3:16-cv-06830-VC-MEJ, filed Apr. 26, 2018, 12 pages.
Exhibit 48 for Declaration of Clara W. Wang in Support of Boston Scientific's Responsive regarding Claim Construction Brief; Opposition to Nevro's Motion for Summary Judgement and Opening Motion for Summary Judgement (Document 358-54), Response to Non-Final Office Action for U.S. Appl. No. 14/503,259, filed Mar. 16, 2015, *Nevro Corp.* vs. *Boston Scientific Corporation and Boston Scientific Neuromodulation Corporation*, Case No. 3:16-cv-06830-VC-MEJ, filed Apr. 26, 2018, 30 pages.
Exhibit 49 for Declaration of Clara W. Wang in Support of Boston Scientific's Responsive regarding Claim Construction Brief; Opposition to Nevro's Motion for Summary Judgement and Opening Motion for Summary Judgement (Document 358-55), Redacted Version of Document Sought to be Filed under Seal—Deposition of Konstantinos Alataris dated Nov. 14, 2017, *Nevro Corp.* vs. *Boston Scientific Corporation and Boston Scientific Neuromodulation Corporation*, Case No. 3:16-cv-06830-VC-MEJ, filed Apr. 26, 2018, 21 pages.
Exhibit 50 for Declaration of Clara W. Wang in Support of Boston Scientific's Responsive regarding Claim Construction Brief; Opposition to Nevro's Motion for Summary Judgement and Opening Motion for Summary Judgement (Document 358-56), Chart for Asserted Claims by Limitation Category, *Nevro Corp.* vs. *Boston Scientific Corporation and Boston Scientific Neuromodulation Corporation*, Case No. 3:16-cv-06830-VC-MEJ, filed Apr. 26, 2018, 12 pages.
Exhibit 51 for Declaration of Clara W. Wang in Support of Boston Scientific's Responsive regarding Claim Construction Brief; Opposition to Nevro's Motion for Summary Judgement and Opening Motion for Summary Judgement (Document 358-57), U.S. Patent Application Publication No. 2009/0204173 to Fang et al., *Nevro Corp.* vs. *Boston Scientific Corporation and Boston Scientific Neuromodulation Corporation*, Case No. 3:16-cv-06830-VC-MEJ, filed Apr. 26, 2018, 33 pages.
Exhibit 52 for Declaration of Clara W. Wang in Support of Boston Scientific's Responsive regarding Claim Construction Brief; Opposition to Nevro's Motion for Summary Judgement and Opening Motion for Summary Judgement (Document 358-58), Applicant-Initiated Interview Summary for U.S. Appl. No. 14/037,262, issued Feb. 25, 2014, *Nevro Corp.* vs. *Boston Scientific Corporation and Boston Scientific Neuromodulation Corporation*, Case No. 3:16-cv-06830-VC-MEJ, filed Apr. 26, 2018, 5 pages.
Exhibit 53 for Declaration of Clara W. Wang in Support of Boston Scientific's Responsive regarding Claim Construction Brief; Opposition to Nevro's Motion for Summary Judgement and Opening Motion for Summary Judgement (Document 358-59), Redacted Version of Document Sought to be Filed under Seal—Videotaped Deposition of Zi-Ping Fang dated Nov. 2, 2017, *Nevro Corp.* vs. *Boston Scientific Corporation and Boston Scientific Neuromodulation Corporation*, Case No. 3:16-cv-06830-VC-MEJ, filed Apr. 26, 2018, 16 pages.
Exhibit 54 for Declaration of Clara W. Wang in Support of Boston Scientific's Responsive regarding Claim Construction Brief; Opposition to Nevro's Motion for Summary Judgement and Opening

(56) References Cited

OTHER PUBLICATIONS

Motion for Summary Judgement (Document 358-60), Handwritten Figure, *Nevro Corp. vs. Boston Scientific Corporation and Boston Scientific Neuromodulation Corporation*, Case No. 3:16-cv-06830-VC-MEJ, filed Apr. 26, 2018, 3 pages.
Exhibit 55 for Declaration of Clara W. Wang in Support of Boston Scientific's Responsive regarding Claim Construction Brief; Opposition to Nevro's Motion for Summary Judgement and Opening Motion for Summary Judgement (Document 358-61), Handwritten Figure, *Nevro Corp. vs. Boston Scientific Corporation and Boston Scientific Neuromodulation Corporation*, Case No. 3:16-cv-06830-VC-MEJ, filed Apr. 26, 2018, 3 pages.
Exhibit 56 for Declaration of Clara W. Wang in Support of Boston Scientific's Responsive regarding Claim Construction Brief; Opposition to Nevro's Motion for Summary Judgement and Opening Motion for Summary Judgement (Document 358-62), Declaration of Rafael Cabunaru in Support of Boston Scientific's Invalidity Contentions, *Nevro Corp. vs. Boston Scientific Corporation and Boston Scientific Neuromodulation Corporation*, Case No. 3:16-cv-06830-VC-MEJ, filed Apr. 26, 2018, 132 pages.
Exhibit 57 for Declaration of Clara W. Wang in Support of Boston Scientific's Responsive regarding Claim Construction Brief; Opposition to Nevro's Motion for Summary Judgement and Opening Motion for Summary Judgement (Document 358-63), Deposition of David Caraway, M.D., Ph.D., dated Nov. 14, 2017, *Nevro Corp. vs. Boston Scientific Corporation and Boston Scientific Neuromodulation Corporation*, Case No. 3:16-cv-06830-VC-MEJ, filed Apr. 26, 2018, 15 pages.
Exhibit 58 for Declaration of Clara W. Wang in Support of Boston Scientific's Responsive regarding Claim Construction Brief; Opposition to Nevro's Motion for Summary Judgement and Opening Motion for Summary Judgement (Document 358-64), Filed under Seal—Document NEVRO_BSXCA0209790-812, *Nevro Corp. vs. Boston Scientific Corporation and Boston Scientific Neuromodulation Corporation*, Case No. 3:16-cv-06830-VC-MEJ, filed Apr. 26, 2018, 1 page.
Exhibit 59 for Declaration of Clara W. Wang in Support of Boston Scientific's Responsive regarding Claim Construction Brief; Opposition to Nevro's Motion for Summary Judgement and Opening Motion for Summary Judgement (Document 358-65), Videotaped Deposition of Dr. James North taken on Nov. 18, 2017, *Nevro Corp. vs. Boston Scientific Corporation and Boston Scientific Neuromodulation Corporation*, Case No. 3:16-cv-06830-VC-MEJ, filed Apr. 26, 2018, 11 pages.
Exhibit 60 for Declaration of Clara W. Wang in Support of Boston Scientific's Responsive regarding Claim Construction Brief; Opposition to Nevro's Motion for Summary Judgement and Opening Motion for Summary Judgement (Document 358-66), Videotaped Deposition of Robert Nathan taken on Nov. 15, 2017, *Nevro Corp. vs. Boston Scientific Corporation and Boston Scientific Neuromodulation Corporation*, Case No. 3:16-cv-06830-VC-MEJ, filed Apr. 26, 2018, 11 pages.
Exhibit 61 for Declaration of Clara W. Wang in Support of Boston Scientific's Responsive regarding Claim Construction Brief; Opposition to Nevro's Motion for Summary Judgement and Opening Motion for Summary Judgement (Document 358-67), Case Report by Yearwood et al., *Nevro Corp. vs. Boston Scientific Corporation and Boston Scientific Neuromodulation Corporation*, Case No. 3:16-cv-06830-VC-MEJ, filed Apr. 26, 2018, 3 pages.
Exhibit 62 for Declaration of Clara W. Wang in Support of Boston Scientific's Responsive regarding Claim Construction Brief; Opposition to Nevro's Motion for Summary Judgement and Opening Motion for Summary Judgement (Document 358-68), Videotaped Deposition of Dr. William S. Rosenberg dated Mar. 21, 2018, *Nevro Corp. vs. Boston Scientific Corporation and Boston Scientific Neuromodulation Corporation*, Case No. 3:16-cv-06830-VC-MEJ, filed Apr. 26, 2018, 11 pages.
Exhibit 63 for Declaration of Clara W. Wang in Support of Boston Scientific's Responsive regarding Claim Construction Brief; Opposition to Nevro's Motion for Summary Judgement and Opening Motion for Summary Judgement (Document 358-69), Document by Yearwood et al., *Nevro Corp. vs. Boston Scientific Corporation and Boston Scientific Neuromodulation Corporation*, Case No. 3:16-cv-06830-VC-MEJ, filed Apr. 26, 2018, 8 pages.
Exhibit 64 for Declaration of Clara W. Wang in Support of Boston Scientific's Responsive regarding Claim Construction Brief; Opposition to Nevro's Motion for Summary Judgement and Opening Motion for Summary Judgement (Document 358-70), Redacted Version of Document Sought to be Filed under Seal—Videotaped Deposition of James Thacker (vol. I) dated Dec. 7, 2017, *Nevro Corp. vs. Boston Scientific Corporation and Boston Scientific Neuromodulation Corporation*, Case No. 3:16-cv-06830-VC-MEJ, filed Apr. 26, 2018, 35 pages.
Exhibit 65 for Declaration of Clara W. Wang in Support of Boston Scientific's Responsive regarding Claim Construction Brief; Opposition to Nevro's Motion for Summary Judgement and Opening Motion for Summary Judgement (Document 358-71), Filed under Seal—Document NEVRO_BSXCA0118164-203, *Nevro Corp. vs. Boston Scientific Corporation and Boston Scientific Neuromodulation Corporation*, Case No. 3:16-cv-06830-VC-MEJ, filed Apr. 26, 2018, 1 page.
Exhibit 66 for Declaration of Clara W. Wang in Support of Boston Scientific's Responsive regarding Claim Construction Brief; Opposition to Nevro's Motion for Summary Judgement and Opening Motion for Summary Judgement (Document 358-72), Videotaped Deposition of Kerry Bradley dated Nov. 8, 2017, *Nevro Corp. vs. Boston Scientific Corporation and Boston Scientific Neuromodulation Corporation*, Case No. 3:16-cv-06830-VC-MEJ, filed Apr. 26, 2018, 10 pages.
Exhibit 67 for Declaration of Clara W. Wang in Support of Boston Scientific's Responsive regarding Claim Construction Brief; Opposition to Nevro's Motion for Summary Judgement and Opening Motion for Summary Judgement (Document 358-73), Response to Final Office Action for U.S. Appl. No. 12/765,685, filed Sep. 19, 2013, *Nevro Corp. vs. Boston Scientific Corporation and Boston Scientific Neuromodulation Corporation*, Case No. 3:16-cv-06830-VC-MEJ, filed Apr. 26, 2018, 15 pages.
Exhibit 68 for Declaration of Clara W. Wang in Support of Boston Scientific's Responsive regarding Claim Construction Brief; Opposition to Nevro's Motion for Summary Judgement and Opening Motion for Summary Judgement (Document 358-74), Response to Non-Final Office Action for U.S. Appl. No. 13/830,992, filed Feb. 24, 2014, *Nevro Corp. vs. Boston Scientific Corporation and Boston Scientific Neuromodulation Corporation*, Case No. 3:16-cv-06830-VC-MEJ, filed Apr. 26, 2018, 15 pages.
Rebuttal Expert Report and Declaration of Daniel Lanovaz (Document 359), *Nevro Corp. vs. Boston Scientific Corporation and Boston Scientific Neuromodulation Corporation*, Case No. 3:16-cv-06830-VC-MEJ, filed Apr. 26, 2018, 10 pages.
Nevro's Reply in Support of its Motion for Summary Adjudication and Opposition to BSC's Motion for Summary Judgement (Document 468), Updated Redacted Version of ECF No. 382-2, *Nevro Corp. vs. Boston Scientific Corporation and Boston Scientific Neuromodulation Corporation*, Case No. 3:16-cv-06830-VC-MEJ, filed Jul. 30, 2018, 40 pages.
Declaration of Joshua Goshorn in Support of Nevro's Reply in Support of Motion for Summary Adjudication and Opposition to BSC's Motion for Summary Judgement (Document 375), *Nevro Corp. vs. Boston Scientific Corporation and Boston Scientific Neuromodulation Corporation*, Case No. 3:16-cv-06830-VC-MEJ, filed May 10, 2018, 2 pages.
Exhibit A for Declaration of Joshua Goshorn in Support of Nevro's Reply in Support of Motion for Summary Adjudication and Opposition to BSC's Motion for Summary Judgement (Document 375-1), Entire Document Sought—Joshua Goshorn opening Expert Report, *Nevro Corp. vs. Boston Scientific Corporation and Boston Scientific Neuromodulation Corporation*, Case No. 3:16-cv-06830-VC-MEJ, filed May 10, 2018, 1 page.
Declaration of Ben Pless in Support of Nevro's Reply in Support of Motion for Summary Adjudication and Opposition to BSC's Motion for Summary Judgement (Document 376), *Nevro Corp. vs. Boston*

(56) References Cited

OTHER PUBLICATIONS

*Scientific Corporation and Boston Scientific Neuromodulation Corporation*, Case No. 3:16-cv-06830-VC-MEJ, filed May 10, 2018, 2 pages.
Exhibit A for Declaration of Ben Pless in Support of Nevro's Reply in Support of Motion for Summary Adjudication and Opposition to BSC's Motion for Summary Judgement (Document 376-1), Redacted Version of Document Sought to be Sealed—Opening Expert Report of Ben Pless, *Nevro Corp. vs. Boston Scientific Corporation and Boston Scientific Neuromodulation Corporation*, Case No. 3:16-cv-06830-VC-MEJ, filed May 10, 2018, 151 pages.
Exhibit B for Declaration of Ben Pless in Support of Nevro's Reply in Support of Motion for Summary Adjudication and Opposition to BSC's Motion for Summary Judgement (Document 376-2), Redacted Version of Document Sought to be Sealed—Corrected Rebuttal Expert Report of Ben Pless regarding Validity, dated Mar. 5, 2018, *Nevro Corp. vs. Boston Scientific Corporation and Boston Scientific Neuromodulation Corporation*, Case No. 3:16-cv-06830-VC-MEJ, filed May 10, 2018, 116 pages.
Declaration of William Sanford Rosenberg in Support of Nevro's Reply in Support of Motion for Summary Adjudication and Opposition to BSC's Motion for Summary Judgement (Document 377), *Nevro Corp. vs. Boston Scientific Corporation and Boston Scientific Neuromodulation Corporation*, Case No. 3:16-cv-06830-VC-MEJ, filed May 10, 2018, 2 pages.
Exhibit A for Declaration of William Sanford Rosenberg in Support of Nevro's Reply in Support of Motion for Summary Adjudication and Opposition to BSC's Motion for Summary Judgement (Document 377-1), Curriculum Vitae of William Sanford Rosenberg, M.D., *Nevro Corp. vs. Boston Scientific Corporation and Boston Scientific Neuromodulation Corporation*, Case No. 3:16-cv-06830-VC-MEJ, filed May 10, 2018, 21 pages.
Exhibit B for Declaration of William Sanford Rosenberg in Support of Nevro's Reply in Support of Motion for Summary Adjudication and Opposition to BSC's Motion for Summary Judgement (Document 377-2), Redacted Version of Document Sought to be Sealed—Deposition of William Sanford Rosenberg, M.D. FAAMS, *Nevro Corp. vs. Boston Scientific Corporation and Boston Scientific Neuromodulation Corporation*, Case No. 3:16-cv-06830-VC-MEJ, filed May 10, 2018, 40 pages.
Declaration of Robert Schiff in Support of Nevro's Reply in Support of Motion for Summary Adjudication and Opposition to BSC's Motion for Summary Judgement (Document 378), *Nevro Corp. vs. Boston Scientific Corporation and Boston Scientific Neuromodulation Corporation*, Case No. 3:16-cv-06830-VC-MEJ, filed May 10, 2018, 2 pages.
Exhibit A—Updated—for Declaration of Robert Schiff in Support of Nevro's Reply in Support of Motion for Summary Adjudication and Opposition to BSC's Motion for Summary Judgement (Document 410), Redacted Version of ECF No. 382-10—Exhibit A to the May 9, 2018 Declaration of Robert Schiff, *Nevro Corp. vs. Boston Sc7ntific Corporation and Boston Scientific Neuromodulation Corporation*, Case No. 3:16-cv-06830-VC-MEJ, filed May 10, 2018, 72 pages.
Declaration of Nicholas Fung in Support of Nevro's Reply in Support of Motion for Summary Adjudication and Opposition to BSC's Motion for Summary Judgement (Document 379), *Nevro Corp. vs. Boston Scientific Corporation and Boston Scientific Neuromodulation Corporation*, Case No. 3:16-cv-06830-VC-MEJ, filed May 10, 2018, 5 pages.
Exhibit 1 for Declaration of Nicholas Fung in Support of Nevro's Reply in Support of Motion for Summary Adjudication and Opposition to BSC's Motion for Summary Judgement (Document 379-1), Claims Chart, *Nevro Corp. vs. Boston Scientific Corporation and Boston Scientific Neuromodulation Corporation*, Case No. 3:16-cv-06830-VC-MEJ, filed May 10, 2018, 3 pages.
Exhibit 2 for Declaration of Nicholas Fung in Support of Nevro's Reply in Support of Motion for Summary Adjudication and Opposition to BSC's Motion for Summary Judgement (Document 379-2), Entire Document Sought to be Sealed—Document BSC-NVRO_ 00713169-172, *Nevro Corp. vs. Boston Scientific Corporation and Boston Scientific Neuromodulation Corporation*, Case No. 3:16-cv-06830-VC-MEJ, filed May 10, 2018, 1 page.
Exhibit 3 for Declaration of Nicholas Fung in Support of Nevro's Reply in Support of Motion for Summary Adjudication and Opposition to BSC's Motion for Summary Judgement (Document 379-3), Redacted Version of Document Sought to be Sealed—BSC's Second Supplemental Responses and Objections to Nevro's First Set of Interrogatory Request (1-8), *Nevro Corp. vs. Boston Scientific Corporation and Boston Scientific Neuromodulation Corporation*, Case No. 3:16-cv-06830-VC-MEJ, filed May 10, 2018, 13 pages.
Exhibit 4 for Declaration of Nicholas Fung in Support of Nevro's Reply in Support of Motion for Summary Adjudication and Opposition to BSC's Motion for Summary Judgement (Document 379-4), Redacted Version of Document Sought to be Sealed—Videotaped Deposition of Sridhar Kothandaraman, *Nevro Corp. vs. Boston Scientific Corporation and Boston Scientific Neuromodulation Corporation*, Case No. 3:16-cv-06830-VC-MEJ, filed May 10, 2018, 14 pages.
Exhibit 5 for Declaration of Nicholas Fung in Support of Nevro's Reply in Support of Motion for Summary Adjudication and Opposition to BSC's Motion for Summary Judgement (Document 379-5), Videotaped Deposition of Brian Erickson dated Dec. 15, 2017, *Nevro Corp. vs. Boston Scientific Corporation and Boston Scientific Neuromodulation Corporation*, Case No. 3:16-cv-06830-VC-MEJ, filed May 10, 2018, 7 pages.
Exhibit 6 for Declaration of Nicholas Fung in Support of Nevro's Reply in Support of Motion for Summary Adjudication and Opposition to BSC's Motion for Summary Judgement (Document 379-6), Plaintiff's Brief regarding Claim Construction of the "Adapted to" Claim Term, *Nevro Corp. vs. Boston Scientific Corporation and Boston Scientific Neuromodulation Corporation*, Case No. 3:16-cv-06830-VC-MEJ, filed May 10, 2018, 7 pages.
Exhibit 7 for Declaration of Nicholas Fung in Support of Nevro's Reply in Support of Motion for Summary Adjudication and Opposition to BSC's Motion for Summary Judgement (Document 379-7), Plaintiff's Response Brief regarding Claim Construction of the "Adapted to" Claim Term, *Nevro Corp. vs. Boston Scientific Corporation and Boston Scientific Neuromodulation Corporation*, Case No. 3:16-cv-06830-VC-MEJ, filed May 10, 2018, 6 pages.
Exhibit 8 for Declaration of Nicholas Fung in Support of Nevro's Reply in Support of Motion for Summary Adjudication and Opposition to BSC's Motion for Summary Judgement (Document 379-8), Deposition of Ben Pless dated Apr. 10, 2018, *Nevro Corp. vs. Boston Scientific Corporation and Boston Scientific Neuromodulation Corporation*, Case No. 3:16-cv-06830-VC-MEJ, filed May 10, 2018, 31 pages.
Exhibit 9 for Declaration of Nicholas Fung in Support of Nevro's Reply in Support of Motion for Summary Adjudication and Opposition to BSC's Motion for Summary Judgement (Document 379-9), Deposition of Dr. Gene Fridman dated Mar. 7, 2018, *Nevro Corp. vs. Boston Scientific Corporation and Boston Scientific Neuromodulation Corporation*, Case No. 3:16-cv-06830-VC-MEJ, filed May 10, 2018, 62 pages.
Exhibit 10 for Declaration of Nicholas Fung in Support of Nevro's Reply in Support of Motion for Summary Adjudication and Opposition to BSC's Motion for Summary Judgement (Document 379-10), Expert Report and Declaration of Gene Fridman, Ph.D., regarding Claim Construction, *Nevro Corp. vs. Boston Scientific Corporation and Boston Scientific Neuromodulation Corporation*, Case No. 3:16-cv-06830-VC-MEJ, filed May 10, 2018, 6 pages.
Exhibit 11 for Declaration of Nicholas Fung in Support of Nevro's Reply in Support of Motion for Summary Adjudication and Opposition to BSC's Motion for Summary Judgement (Document 379-11), Article by Tan et al., *Nevro Corp. vs. Boston Scientific Corporation and Boston Scientific Neuromodulation Corporation*, Case No. 3:16-cv-06830-VC-MEJ, filed May 10, 2018, 8 pages.
Exhibit 12 for Declaration of Nicholas Fung in Support of Nevro's Reply in Support of Motion for Summary Adjudication and Opposition to BSC's Motion for Summary Judgement (Document 379-12), Decision Denying Institution of Inter Partes Review for U.S. Pat. No. 8,359, 102 (Case IPR2015-01203), *Nevro Corp. vs. Boston*

(56) References Cited

OTHER PUBLICATIONS

*Scientific Corporation and Boston Scientific Neuromodulation Corporation*, Case No. 3:16-cv-06830-VC-MEJ, filed May 10, 2018, 21 pages.
Exhibit 13 for Declaration of Nicholas Fung in Support of Nevro's Reply in Support of Motion for Summary Adjudication and Opposition to BSC's Motion for Summary Judgement (Document 379-13), Certified U.S. Pat. No. 9,327,125, *Nevro Corp. vs. Boston Scientific Corporation and Boston Scientific Neuromodulation Corporation*, Case No. 3: 16-cv-06830-VC-MEJ, filed May 10, 2018, 66 pages.
Exhibit 14 for Declaration of Nicholas Fung in Support of Nevro's Reply in Support of Motion for Summary Adjudication and Opposition to BSC's Motion for Summary Judgement (Document 379-14), U.S. Pat. No. 9,492,664, *Nevro Corp. vs. Boston Scientific Corporation and Boston Scientific Neuromodulation Corporation*, Case No. 3:16-cv-06830-VC-MEJ, filed May 10, 2018, 25 pages.
Exhibit 15 for Declaration of Nicholas Fung in Support of Nevro's Reply in Support of Motion for Summary Adjudication and Opposition to BSC's Motion for Summary Judgement (Document 379-15), U.S. Pat. No. 9,339,655, *Nevro Corp. vs. Boston Scientific Corporation and Boston Scientific Neuromodulation Corporation*, Case No. 3:16-cv-06830-VC-MEJ, filed May 10, 2018, 23 pages.
Exhibit 16 for Declaration of Nicholas Fung in Support of Nevro's Reply in Support of Motion for Summary Adjudication and Opposition to BSC's Motion for Summary Judgement (Document 379-16), Redacted Version of Document Sought to be Sealed—Videotaped Deposition of Richard T. Mihran, Ph.D., dated Mar. 12, 2018, *Nevro Corp. vs. Boston Scientific Corporation and Boston Scientific Neuromodulation Corporation*, Case No. 3:16-cv-06830-VC-MEJ, filed May 10, 2018, 29 pages.
Exhibit 17 for Declaration of Nicholas Fung in Support of Nevro's Reply in Support of Motion for Summary Adjudication and Opposition to BSC's Motion for Summary Judgement (Document 379-17), Redacted Version of Document Sought to be Sealed—Videotaped Deposition of Jim Cassidy, dated May 17, 2017, *Nevro Corp. vs. Boston Scientific Corporation and Boston Scientific Neuromodulation Corporation*, Case No. 3:16-cv-06830-VC-MEJ, filed May 10, 2018, 13 pages.
Exhibit 18 for Declaration of Nicholas Fung in Support of Nevro's Reply in Support of Motion for Summary Adjudication and Opposition to BSC's Motion for Summary Judgement (Document 379-18), Redacted Version of Document Sought to be Sealed—Deposition of Adam Lipson, M.D., dated Apr. 12, 2018, *Nevro Corp. vs. Boston Scientific Corporation and Boston Scientific Neuromodulation Corporation*, Case No. 3:16-cv-06830-VC-MEJ, filed May 10, 2018, 10 pages.
Exhibit 19 for Declaration of Nicholas Fung in Support of Nevro's Reply in Support of Motion for Summary Adjudication and Opposition to BSC's Motion for Summary Judgement (Document 379-19), Redacted Version of Document Sought to be Sealed—BSC's Nov. 10, 17 Supplemental Responses and Objections to Nevro's Interrogatory Requests Nos. 2, 4, 5, and 7, *Nevro Corp. vs. Boston Scientific Corporation and Boston Scientific Neuromodulation Corporation*, Case No. 3:16-cv-06830-VC-MEJ, filed May 10, 2018, 9 pages.
Exhibit 20 for Declaration of Nicholas Fung in Support of Nevro's Reply in Support of Motion for Summary Adjudication and Opposition to BSC's Motion for Summary Judgement (Document 379-20), Entire Document Sought to be Sealed—Deposition of Kaoru Adair, *Nevro Corp. vs. Boston Scientific Corporation and Boston Scientific Neuromodulation Corporation*, Case No. 3:16-cv-06830-VC-MEJ, filed May 10, 2018, 1 page.
Exhibit 21—Updated—for Declaration of Nicholas Fung in Support of Nevro's Reply in Support of Motion for Summary Adjudication and Opposition to BSC's Motion for Summary Judgement (Document 471), Redacted Version of ECF No. 382-24—Videotaped Deposition of Kaoru Adair dated May 10, 2017, *Nevro Corp. vs. Boston Scientific Corporation and Boston Scientific Neuromodulation Corporation*, Case No. 3:16-cv-06830-VC-MEJ, filed May 10, 2018, 18 pages.
Exhibit 22 Declaration of Nicholas Fung in Support of Nevro's Reply in Support of Motion for Summary Adjudication and Opposition to BSC's Motion for Summary Judgement (Document 379-22), Redacted Version of Document Sought to be Sealed—Nevro Corp.'s First Amended Disclosure of Asserted Claims and Infringement Contentions, *Nevro Corp. vs. Boston Scientific Corporation and Boston Scientific Neuromodulation Corporation*, Case No. 3:16-cv-06830-VC-MEJ, filed May 10, 2018, 6 pages.
Exhibit 23 for Declaration of Nicholas Fung in Support of Nevro's Reply in Support of Motion for Summary Adjudication and Opposition to BSC's Motion for Summary Judgement (Document 379-23), Entire Document Sought to be Sealed—Document BSC-NVRO_00720938-940, *Nevro Corp. vs. Boston Scientific Corporation and Boston Scientific Neuromodulation Corporation*, Case No. 3:16-cv-06830-VC-MEJ, filed May 10, 2018, 1 page.
Exhibit 24 for Declaration of Nicholas Fung in Support of Nevro's Reply in Support of Motion for Summary Adjudication and Opposition to BSC's Motion for Summary Judgement (Document 379-24), Redacted Version of Document Sought to be Sealed—Deposition of Joshua Goshorn, dated Mar. 23, 2018, *Nevro Corp. vs. Boston Scientific Corporation and Boston Scientific Neuromodulation Corporation*, Case No. 3:16-cv-06830-VC-MEJ, filed May 10, 2018, 15 pages.
Exhibit 25 for Declaration of Nicholas Fung in Support of Nevro's Reply in Support of Motion for Summary Adjudication and Opposition to BSC's Motion for Summary Judgement (Document 379-25), Redacted Version of Document Sought to be Sealed—Videotaped Deposition of Daniel Lanovaz, dated Mar. 21, 2018, *Nevro Corp. vs. Boston Scientific Corporation and Boston Scientific Neuromodulation Corporation*, Case No. 3:16-cv-06830-VC-MEJ, filed May 10, 2018, 11 pages.
Exhibit 26 for Declaration of Nicholas Fung in Support of Nevro's Reply in Support of Motion for Summary Adjudication and Opposition to BSC's Motion for Summary Judgement (Document 379-26), Redacted Version of Document Sought to be Sealed —Rebuttal Expert Report of Richard T. Mihran, Ph.D. dated Feb. 14, 2018, *Nevro Corp. vs. Boston Scientific Corporation and Boston Scientific Neuromodulation Corporation*, Corporation, Case No. 3:16-cv-06830-VC-MEJ, filed May 10, 2018, 23 pages.
Exhibit 27 for Declaration of Nicholas Fung in Support of Nevro's Reply in Support of Motion for Summary Adjudication and Opposition to BSC's Motion for Summary Judgement (Document 379-27), Expert Report of Richard T. Mihran, Ph.D., regarding Invalidity of U.S. Pat. Nos. 8,712,533; 9,327,125; 8,359,102; 9,480,842; 9,333,357; 8,792,988, and 8,768,472, *Nevro Corp. vs. Boston Scientific Corporation and Boston Scientific Neuromodulation Corporation*, Case No. 3:16-cv-06830-VC-MEJ, filed May 10, 2018, 6 pages.
Exhibit 28 for Declaration of Nicholas Fung in Support of Nevro's Reply in Support of Motion for Summary Adjudication and Opposition to BSC's Motion for Summary Judgement (Document 379-28), Declaration of Rafael Carbunaru in Support of Boston Scientific's Invalidity Contentions, *Nevro Corp. vs. Boston Scientific Corporation and Boston Scientific Neuromodulation Corporation*, Case No. 3:16-cv-06830-VC-MEJ, filed May 10, 2018, 13 pages.
Exhibit 29 for Declaration of Nicholas Fung in Support of Nevro's Reply in Support of Motion for Summary Adjudication and Opposition to BSC's Motion for Summary Judgement (Document 379-29), Redacted Version of Document Sought to be Sealed—Videotaped Deposition of Nevro Corp., with designated corporate representative Rafael Carbunaru, dated May 18, 2017, *Nevro Corp. vs. Boston Scientific Corporation and Boston Scientific Neuromodulation Corporation*, Case No. 3:16-cv-06830-VC-MEJ, filed May 10, 2018, 8 pages.
Declaration of Carson D. Anderson in Support of Nevro's Administrative Motion to File under Seal Portions of Nevro's Reply in Support of It's Motion for Summary Adjudication and Opposition to BSC's Motion for Summary Judgement (Document 382), *Nevro*

(56) References Cited

OTHER PUBLICATIONS

*Corp.* vs. *Boston Scientific Corporation and Boston Scientific Neuromodulation Corporation*, Case No. 3:16-cv-06830-VC-MEJ, filed May 14, 2018, 13 pages.

Exhibit A—Updated—for Declaration of Carson D. Anderson in Support of Nevro's Administrative Motion to File under Seal Portions of Nevro's Reply in Support of It's Motion for Summary Adjudication and Opposition to BSC's Motion for Summary Judgement (Document 468), Redacted Version of ECF No. 382-2—Nevro's Reply in Support of its Motion for Summary Adjudication and Opposition to BSC's Motion for Summary Judgment, *Nevro Corp.* vs. *Boston Scientific Corporation and Boston Scientific Neuromodulation Corporation*, Case No. 3:16-cv-06830-VC-MEJ, filed May 14, 2018, 40 pages.

Exhibit B for Declaration of Carson D. Anderson in Support of Nevro's Administrative Motion to File under Seal Portions of Nevro's Reply in Support of It's Motion for Summary Adjudication and Opposition to BSC's Motion for Summary Judgement (Document 382-3), Redacted Version of Document Sought to be Filed under Seal—Expert Report of Joshua Goshorn, *Nevro Corp.* vs. *Boston Scientific Corporation and Boston Scientific Neuromodulation Corporation*, Case No. 3:16-cv-06830-VC-MEJ, filed May 14, 2018, 15 pages.

Exhibit C for Declaration of Carson D. Anderson in Support of Nevro's Administrative Motion to File under Seal Portions of Nevro's Reply in Support of It's Motion for Summary Adjudication and Opposition to BSC's Motion for Summary Judgement (Document 382-5), Redacted Version of Document Sought to be Filed under Seal—Expert Report of William S. Rosenberg, M.D., Faans, *Nevro Corp.* vs. *Boston Scientific Corporation and Boston Scientific Neuromodulation Corporation*, Case No. 3:16-cv-06830-VC-MEJ, filed May 14, 2018, 41 pages.

Exhibit D—Updated—for Declaration of Carson D. Anderson in Support of Nevro's Administrative Motion to File under Seal Portions of Nevro's Reply in Support of It's Motion for Summary Adjudication and Opposition to BSC's Motion for Summary Judgement (Document 469), Redacted Version of ECF No. 382-8—Opening Expert Report of Ben Pless regarding Infringement, dated Jan. 18, 2018, *Nevro Corp.* vs. *Boston Scientific Corporation and Boston Scientific Neuromodulation Corporation*, Case No. 3:16-cv-06830-VC-MEJ, filed May 14, 2018, 152 pages.

Exhibit E—Updated—for Declaration of Carson D. Anderson in Support of Nevro's Administrative Motion to File under Seal Portions of Nevro's Reply in Support of It's Motion for Summary Adjudication and Opposition to BSC's Motion for Summary Judgement (Document 470), Redacted Version of ECF No. 382-10—Expert Report of Robert Schiff, Ph.D., RAC, CQA, FRAPS, *Nevro Corp.* vs. *Boston Scientific Corporation and Boston Scientific Neuromodulation Corporation*, Case No. 3:16-cv-06830-VC-MEJ, filed May 14, 2018, 72 pages.

Exhibit F for Declaration of Carson D. Anderson in Support of Nevro's Administrative Motion to File under Seal Portions of Nevro's Reply in Support of It's Motion for Summary Adjudication and Opposition to BSC's Motion for Summary Judgement (Document 382-11), Redacted Version of Document Sought to be Filed under Seal—Cross-Border HCP Arrangement Request, N*Nevro Corp.* vs. *Boston Scientific Corporation and Boston Scientific Neuromodulation Corporation*, Case No. 3:16-cv-06830-VC-MEJ, filed May 14, 2018, 6 pages.

Exhibit G for Declaration of Carson D. Anderson in Support of Nevro's Administrative Motion to File under Seal Portions of Nevro's Reply in Support of It's Motion for Summary Judgement (Document 382-13), Redacted Version of Document Sought to be Filed under Seal—BSC's Second Supplemental Responses and Objections to Nevro's First Set of Interrogatory Request (1-8), *Nevro Corp.* vs. *Boston Scientific Corporation and Boston Scientific Neuromodulation Corporation*, Case No. 3:16-cv-06830-VC-MEJ, filed May 14, 2018, 14 pages.

Exhibit H for Declaration of Carson D. Anderson in Support of Nevro's Administrative Motion to File under Seal Portions of Nevro's Reply in Support of It's Motion for Summary Adjudication and Opposition to BSC's Motion for Summary Judgement (Document 382-15), Redacted Version of Document Sought to be Filed under Seal—Videotaped Deposition of Sridhar Kothandaraman, dated Nov. 17, 2017, *Nevro Corp.* vs. *Boston Scientific Corporation and Boston Scientific Neuromodulation Corporation*, Case No. 3:16-cv-06830-VC-MEJ, filed May 14, 2018, 15 pages.

Exhibit I for Declaration of Carson D. Anderson in Support of Nevro's Administrative Motion to File under Seal Portions of Nevro's Reply in Support of It's Motion for Summary Adjudication and Opposition to BSC's Motion for Summary Judgement (Document 382-17), Redacted Version of Document Sought to be Filed under Seal—Videotaped Deposition of Richard T. Mihran, dated Mar. 12, 2018, *Nevro Corp.* vs. *Boston Scientific Corporation and Boston Scientific Neuromodulation Corporation*, Case No. 3:16-cv-06830-VC-MEJ, filed May 14, 2018, 30 pages.

Exhibit J for Declaration of Carson D. Anderson in Support of Nevro's Administrative Motion to File under Seal Portions of Nevro's Reply in Support of It's Motion for Summary Adjudication and Opposition to BSC's Motion for Summary Judgement (Document 382-19), Redacted Version of Document Sought to be Filed under Seal—BSC's Nov. 10, 2017 Supplemental Responses and Objections to Nevro's Interrogatory Requests Nos. 2, 4, 5, and 7, *Nevro Corp.* vs. *Boston Scientific Corporation and Boston Scientific Neuromodulation Corporation*, Case No. 3:16-cv-06830-VC-MEJ, filed May 14, 2018, 10 pages.

Exhibit K for Declaration of Carson D. Anderson in Support of Nevro's Administrative Motion to File under Seal Portions of Nevro's Reply in Support of It's Motion for Summary Adjudication and Opposition to BSC's Motion for Summary Judgement (Document 382-21), Redacted Version of Document Sought to be Filed under Seal—Dec. 14, 2016 Correspondence between Boston Scientific and U.S. Food and Drug Administration, *Nevro Corp.* vs. *Boston Scientific Corporation and Boston Scientific Neuromodulation Corporation*, Case No. 3:16-cv-06830-VC-MEJ, filed May 14, 2018, 23 pages.

Exhibit L —Updated for Declaration of Carson D. Anderson in Support of Nevro's Administrative Motion to File under Seal Portions of Nevro's Reply in Support of It's Motion for Summary Adjudication and Opposition to BSC's Motion for Summary Judgement (Document 471), Updated Redacted Version of ECF No. 382-24—Videotaped Deposition of Kaoru Lee Adair, dated May 10, 2017, *Nevro Corp.* vs. *Boston Scientific Corporation and Boston Scientific Neuromodulation Corporation*, Case No. 3:16-cv-06830-VC-MEJ, filed May 14, 2018, 18 pages.

Exhibit M for Declaration of Carson D. Anderson in Support of Nevro's Administrative Motion to File under Seal Portions of Nevro's Reply in Support of It's Motion for Summary Adjudication and Opposition to BSC's Motion for Summary Judgement (Document 382-25), Redacted Version of Document Sought to be Filed under Seal—Nevro Corp.'s First Amended Disclosure of Asserted Claims and Infringement Contentions, *Nevro Corp.* vs. *Boston Scientific Corporation and Boston Scientific Neuromodulation Corporation*, Case No. 3:16-cv-06830-VC-MEJ, filed May 14, 2018, 7 pages.

Exhibit N for Declaration of Carson D. Anderson in Support of Nevro's Administrative Motion to File under Seal Portions of Nevro's Reply in Support of It's Motion for Summary Adjudication and Opposition to BSC's Motion for Summary Judgement (Document 382-27), Redacted Version of Document Sought to be Filed under Seal—Feb. 2016 Email regarding Precision 10K Training Follow-up, *Nevro Corp.* vs. *Boston Scientific Corporation and Boston Scientific Neuromodulation Corporation*, Case No. 3:16-cv-06830-VC-MEJ, filed May 14, 2018, 5 pages.

Exhibit O for Declaration of Carson D. Anderson in Support of Nevro's Administrative Motion to File under Seal Portions of Nevro's Reply in Support of It's Motion for Summary Adjudication and Opposition to BSC's Motion for Summary Judgement (Document 382-29), Redacted Version of Document Sought to be Filed under Seal—Deposition of Joshua Goshorn dated Mar. 23, 2018,

(56) References Cited

OTHER PUBLICATIONS

*Nevro Corp.* vs. *Boston Scientific Corporation and Boston Scientific Neuromodulation Corporation*, Case No. 3:16-cv-06830-VC-MEJ, filed May 14, 2018, 16 pages.
Exhibit P for Declaration of Carson D. Anderson in Support of Nevro's Administrative Motion to File under Seal Portions of Nevro's Reply in Support of It's Motion for Summary Adjudication and Opposition to BSC's Motion for Summary Judgement (Document 382-31), Redacted Version of Document Sought to be Filed under Seal—Videotaped Deposition of Daniel Lanovaz dated Mar. 21, 2018, *Nevro Corp.* vs. *Boston Scientific Corporation and Boston Scientific Neuromodulation Corporation*, Case No. 3:16-cv-06830-VC-MEJ, filed May 14, 2018, 12 pages.
[Proposed] Order Granting Administrative Motion to File under Seal Portions of Nevro's Reply in Support of It's Motion for Summary Adjudication and Opposition to BSC's Motion for Summary Judgement and Supporing Documents (Document 382-33), *Nevro Corp.* vs. *Boston Scientific Corporation and Boston Scientific Neuromodulation Corporation*, Case No. 3:16-cv-06830-VC-MEJ, filed May 14, 2018, 7 pages.
Updated Boston Scientific's Reply in Support of Motion for Summary Judgement (Document 473), Updated Redacted Version of ECF No. 397-3, *Nevro Corp.* vs. *Boston Scientific Corporation and Boston Scientific Neuromodulation Corporation*, Case No. 3:16-cv-06830-VC-MEJ, filed Jul. 30, 2018, 27 pages.
Declaration of Carson D. Anderson in Support of Boston Scientific's Reply in Support of Motion for Summary Judgement (Document 398-1), Redacted Version of Document Sought to be Filed under Seal—Cross-Border HCP Arrangement Request, *Nevro Corp.* vs. *Boston Scientific Corporation and Boston Scientific Neuromodulation Corporation*, Case No. 3:16-cv-06830-VC-MEJ, filed May 24, 2018, 3 pages.
Exhibit 1 for Declaration of Carson D. Anderson in Support of Boston Scientific's Reply in Support of Motion for Summary Judgement (Document 398-2), Redacted Version of Document Sought to be Filed under Seal—May 2004 Email regarding Post-Market Studies for AB SCS System, *Nevro Corp.* vs. *Boston Scientific Corporation and Boston Scientific Neuromodulation Corporation*, Case No. 3:16-cv-06830-VC-MEJ, filed May 24, 2018, 5 pages.
Exhibit 2 for Declaration of Carson D. Anderson in Support of Boston Scientific's Reply in Support of Motion for Summary Judgement (Document 398-3), Redacted Version of Document Sought to be Filed under Seal —Corrected Rebuttal Expert Report of Ben Pless regarding Validity, dated Mar. 5, 2018, *Nevro Corp.* vs. *Boston Scientific Corporation and Boston Scientific Neuromodulation Corporation*, Case No. 3:16-cv-06830-VC-MEJ, filed May 24, 2018, 4 pages.
Exhibit 3 for Declaration of Carson D. Anderson in Support of Boston Scientific's Reply in Support of Motion for Summary Judgement (Document 398-4), U.S. Pat. No. 7,389,145 by Kilgore et al., *Nevro Corp.* vs. *Boston Scientific Corporation and Boston Scientific Neuromodulation Corporation*, Case No. 3:16-cv-06830-VC-MEJ, filed May 24, 2018, 12 pages.
Exhibit 4 for Declaration of Carson D. Anderson in Support of Boston Scientific's Reply in Support of Motion for Summary Judgement (Document 398-5), Redacted Version of Document Sought to be Filed under Seal—Videotaped Deposition of Robert Schiff, dated Mar. 15, 2018, *Nevro Corp.* vs. *Boston Scientific Corporation and Boston Scientific Neuromodulation Corporation*, Case No. 3:16-cv-06830-VC-MEJ, filed May 24, 2018, 19 pages.
Exhibit 5 for Declaration of Carson D. Anderson in Support of Boston Scientific's Reply in Support of Motion for Summary Judgement (Document 398-6), Filed under Seal—Document NEVRO_BSXCA0093092-109, *Nevro Corp.* vs. *Boston Scientific Corporation and Boston Scientific Neuromodulation Corporation*, Case No. 3:16-cv-06830-VC-MEJ, filed May 24, 2018, 1 page.
Exhibit 6 for Declaration of Carson D. Anderson in Support of Boston Scientific's Reply in Support of Motion for Summary Judgement (Document 398-7), Filed under Seal—Document NEVRO_BSXCA0067869-75, *Nevro Corp.* vs. *Boston Scientific Corporation and Boston Scientific Neuromodulation Corporation*, Case No. 3:16-cv-06830-VC-MEJ, filed May 24, 2018, 1 page.
Exhibit 7 for Declaration of Carson D. Anderson in Support of Boston Scientific's Reply in Support of Motion for Summary Judgement (Document 398-8), Filed under Seal—Document NEVRO_BSXCA0147580-86, *Nevro Corp.* vs. *Boston Scientific Corporation and Boston Scientific Neuromodulation Corporation*, Case No. 3:16-cv-06830-VC-MEJ, filed May 24, 2018, 1 page.
Exhibit 8 for Declaration of Carson D. Anderson in Support of Boston Scientific's Reply in Support of Motion for Summary Judgement (Document 398-9), Filed under Seal—Opening Expert Report of Ben Pless regarding Infringement, dated Jan. 18, 2018, *Nevro Corp.* vs. *Boston Scientific Corporation and Boston Scientific Neuromodulation Corporation*, Case No. 3:16-cv-06830-VC-MEJ, filed May 24, 2018, 7 pages.
Exhibit 9 for Declaration of Carson D. Anderson in Support of Boston Scientific's Reply in Support of Motion for Summary Judgement (Document 398-10), Filed under Seal—Expert Report of W. Todd Schoettelkotte Relating to Damages, dated Jan. 18, 2018, *Nevro Corp.* vs. *Boston Scientific Corporation and Boston Scientific Neuromodulation Corporation*, Case No. 3:16-cv-06830-VC-MEJ, filed May 24, 2018, 1 page.
Exhibit 10 for Declaration of Carson D. Anderson in Support of Boston Scientific's Reply in Support of Motion for Summary Judgement (Document 398-11), Redacted Version of Document Sought to be Filed under Seal—Design Change Analysis Form (DCAF), *Nevro Corp.* vs. *Boston Scientific Corporation and Boston Scientific Neuromodulation Corporation*, Case No. 3:16-cv-06830-VC-MEJ, filed May 24, 2018, 2 pages.
Exhibit 11 for Declaration of Carson D. Anderson in Support of Boston Scientific's Reply in Support of Motion for Summary Judgement (Document 398-12), Redacted Version of Document Sought to be Filed under Seal —Videotaped Deposition of Rafael Carbunaru, Ph.D., dated Nov. 14, 2017, *Nevro Corp.* vs. *Boston Scientific Corporation and Boston Scientific Neuromodulation Corporation*, Case No. 3:16-cv-06830-VC-MEJ, filed May 24, 2018, 9 pages.
Exhibit 12 for Declaration of Carson D. Anderson in Support of Boston Scientific's Reply in Support of Motion for Summary Judgement (Document 398-13), Declaration of Konstantinos Alataris under 37 CFR 1.1.32, dated Jun. 6, 2013, *Nevro Corp.* vs. *Boston Scientific Corporation and Boston Scientific Neuromodulation Corporation*, Case No. 3:16-cv-06830-VC-MEJ, filed May 24, 2018, 9 pages.
Exhibit 13 for Declaration of Carson D. Anderson in Support of Boston Scientific's Reply in Support of Motion for Summary Judgement (Document 398-14), Information Disclosure Statement SB-08 Form for U.S. Appl. No. 14/525,134, *Nevro Corp.* vs. *Boston Scientific Corporation and Boston Scientific Neuromodulation Corporation*, Case No. 3:16-cv-06830-VC-MEJ, filed May 24, 2018, 13 pages.
Exhibit 14 for Declaration of Carson D. Anderson in Support of Boston Scientific's Reply in Support of Motion for Summary Judgement (Document 398-15), Amendment in Response to Final Office Action for U.S. Appl. No. 12/765,685, filed Sep. 19, 2013, *Nevro Corp.* vs. *Boston Scientific Corporation and Boston Scientific Neuromodulation Corporation*, Case No. 3:16-cv-06830-VC-MEJ, filed May 24, 2018, 15 pages.
Exhibit 15 for Declaration of Carson D. Anderson in Support of Boston Scientific's Reply in Support of Motion for Summary Judgement (Document 398-16), Amendment in Response to Non-Final Office Action for U.S. Appl. No. 13/830,992, filed Feb. 24, 2014, *Nevro Corp.* vs. *Boston Scientific Corporation and Boston Scientific Neuromodulation Corporation*, Case No. 3:16-cv-06830-VC-MEJ, filed May 24, 2018, 15 pages.
Exhibit 16 for Declaration of Carson D. Anderson in Support of Boston Scientific's Reply in Support of Motion for Summary Judgement (Document 398-17), Amendment in Response to Final Office Action for U.S. Appl. No. 14/292,671, filed Jan. 17, 2017, *Nevro Corp.* vs. *Boston Scientific Corporation and Boston Scientific Neuromodulation Corporation*, Case No. 3:16-cv-06830-VC-MEJ, filed May 24, 2018, 12 pages.

(56) References Cited

OTHER PUBLICATIONS

Declaration of J. Lawrence Stevens in Support of Boston Scientific's Reply in Support of Motion for Summary Judgement (Document 398-18), *Nevro Corp. vs. Boston Scientific Corporation and Boston Scientific Neuromodulation Corporation*, Case No. 3:16-cv-06830-VC-MEJ, filed May 24, 2018, 34 pages.
Boston Scientific's Responsive Claim Construction Brief, Opposition to in Nevro's Motion for Summary Judgment and Opening Motion for Summary Judgment (Document 358), N*Nevro Corp. vs. Boston Scientific Corporation and Boston Scientific Neuromodulation Corporation*, Case No. 3:16-cv-06830-VC-MEJ, filed Apr. 26, 2018, 60 pages.
Declaration of Rafael Carbunaru in Support of Boston Scientific Administrative Motion to File under Seal Portions of Boston Scientific's Opposition to Nevro's Motion to Strike BSC's Undisclosed Invalidity Theories (Dkt No. 340) and Supporting Documents (Document 355-2), *Nevro Corp. vs. Boston Scientific Corporation and Boston Scientific Neuromodulation Corporation*, Case No. 3:16-cv-06830-VC-MEJ, filed Apr. 26, 2018, 3 pages.
Declaration of Sridhar Kothandaraman (Document 356-1), *Nevro Corp. vs. Boston Scientific Corporation and Boston Scientific Neuromodulation Corporation*, Case No. 3:16-cv-06830-VC-MEJ, filed Apr. 26, 2018, 4 pages.
Exhibit B to the Declaration of Clara W. Wang in Support of Nevro's Administrative Motion to File under Seal Portions of Nevro's Reply to Strike BSC's Invalidity Positions and Supporting Documents (Dkt No. 366) (Document 368-4), *Nevro Corp. vs. Boston Scientific Corporation and Boston Scientific Neuromodulation Corporation*, Case No. 3: 16-cv-06830-VC-MEJ, filed May 7, 2018, 10 pages.
Order Re: Claim Construction and Cross-Motions for Summary Judgement (Document 449), *Nevro Corp. vs. Boston Scientific Corporation and Boston Scientific Neuromodulation Corporation*, Case No. 3:16-cv-06830-VC-MEJ, filed Jul. 24, 2018, 9 pages.
Tentative Ruling (Document 422), *Nevro Corp. vs. Boston Scientific Corporation and Boston Scientific Neuromodulation Corporation*, Case No. 3:16-cv-06830-VC-MEJ, filed Jul. 5, 2018, 3 pages.
Nevro Written Submissions for European Patent No. 2207587, Opponents: Medtronic Inc., and Boston Scientific Neuromodulation Corporation, mailed Jul. 24, 2018, 9 pages.
Notice of Opposition for European Patent No. 3156099, Proprietor of the Patent: Nevro Corporation; Opponent: Boston Scientific Neuromodulation Corporation, Aug. 2, 2018, 27 pages.
Thomson et al., "Effects of Rate on Analgesia in Kilohertz Frequency Spinal Cord Stimulation: Results of the PROCO Randomized Controlled Trial," Neuromodulation: Technology at the Neural Interface, 2017, 10 pages.
"The Need for Mechanism-Based Medicine in Neuromodulation," Neuromodulation: Technology at the Neural Interface, 2012, 7 pages.
Abejon et al., "Is Impedance a Parameter to be Taken into Account in Spinal Cord Stimulation?" Pain Physician, 2007, 8 pages.
Acticare.com website, http://web.archive.org/web/*/acticare.com, Internet Archive Way Back Machine, 2012, 22 pages.
Advanced Neuromodulation Systems, Compustim SCS Systems, Clinical Manual, 1997, 52 pages.
Agnew et al., "Considerations for safety with chronically implanted nerve electrodes," Epilepsia, 31.s2, 1990, 6 pages.
Al-Kaisy et al., "10 KHz High-Frequency Spinal Cord Stimulation for Chronic Axial Low Back Pain in Patients With No History of Spinal Surgery: A Preliminary, Prospective, Open Label and Proof-of-Concept Study," Neuromodulation: Technology at the Neural Interface, 2016, 8 pages.
Al-Kaisy et al., "Prospective, Randomized, Sham-Control, Double Blind, Crossover Trial of Subthreshold Spinal Cord Stimulation at Various Kilohertz Frequencies in Subjects Suffering from Failed Back Surgery Syndrome," International Neuromodulation Society, 2018, 9 pages.
Al-Kaisy et al., "Sustained Effectiveness of 10kHz High-Frequency Spinal Cord Stimulation for Patients with Chronic, Low Back Pain: 24-month Results of Prospective Multicenter Study," Pain Medicine, 2014, 8 pages.
Al-Kaisy et al., "The Use of 10-Kilohertz Spinal Cord Stimulation in a Cohort of Patients with Chronic Neuropathic Limb Pain Refractory to Medical Management," Neuromodulation Technology at the Neural, Interface, 2015, 6 pages.
Al-Kaisy et al., Poster: "High-Frequency Spinal Cord Stimulation at 10 KHz for the Treatment of Chronic Back Pain Patients without Prior Back Surgery," 1 page.
Alo et al., "Factors Affecting Impedance of Percutaneous Leads in Spinal Cord Stimulation," International Neuromodulation Society, vol. 9, No. 2, 2006, 8 pages.
Alo et al., "New Trends in Neuromodulation for the Management of Neuropathic Pain," Neurosurgery, vol. 50, No. 4, Apr. 2002, 15 pages.
Amendment in Response to Ex Parte Office Action for U.S. Appl. No. 13/446,970, First Named Inventor: Konstantinos Alataris, Mailed: Nov. 28, 2012, 14 pages.
Amendment in Response to Non-Final Office Action for U.S. Appl. No. 13/245,450, First Named Inventor: Konstantinos Alataris, filed Feb. 7, 2012, 15 pages.
Amendment in Response to Non-Final Office Action for U.S. Appl. No. 12/765,747, First Named Inventor: Konstantinos Alataris, Mailed: Jan. 24, 2014, 21 pages.
Applicant-Initiated Interview Summary for U.S. Appl. No. 13/245,450, First Named Inventor: Konstantinos Alataris, Mailed: Feb. 1, 2012, 2 pages.
Applicant-Initiated Interview Summary for U.S. Appl. No. 13/725,770, First Named Inventor: Konstantinos Alataris, Mailed: Apr. 5, 2013, 3 pages.
Applicant-Initiated Interview Summary for U.S. Appl. No. 12/765,747, First Named Inventor: Konstantinos Alataris, Mailed: Sep. 11, 2013, 3 pages.
Application Data Sheet for U.S. Appl. No. 13/446,970 (U.S. Pat. No. 8,359,102), First Named Inventor: Konstantinos Alataris, filed Apr. 13, 2012, 6 pages.
Augustinsson et al., "Spinal Cord Stimulation in Cardiovascular Disease," Functional Neurosurgery, vol. 6, No. 1, Jan. 1995, 10 pages.
Bahdra et al., Stimulation of High-Frequency Sinusoidal Electrical Block of Mammalian Myelinated Axons, J Comput Neurosco, 22:313-326, 2007.
Bara et al., Poster re: High Frequency Spinal Cord Stimulation for Dominant Back Pain—1 year follow up, 2013, 1 page.
Barolat et al., "Multifactorial Analysis of Epidural Spinal Cord Stimulation," Sterotactic and Functional Neurosurgery, 1991; 56: 77-103.
Barolat et al., "Spinal Cord Stimulation for Chronic Pain Management," Seminars in Neurosurgery, vol. 15, Nos. 2/3, 2004, 26 pages.
Barolat et al., "Surgical Management of Pain—Spinal Cord Stimulation: Equipment and Implantation Techniques," Chapter 41, Thieme Medical Publishers, New York, 2002, 11 pages.
Bennett et al., "Spinal Cord Stimulation for Complex regional pain syndrome | [RSD]: a Retrospective Multicenter Experience from 1995 to 1998 of 101 patients." Neuromodulation, vol. 2, No. 3, 1999, 9 pages.
Benyamin et al., "A Case of Spinal Cord Stimulation in Raynaud's Phenomenon: Can Subthreshold Sensory Stimulation Have an Effect?" Pain Physician www.painphysicianjournal.com, 2007, 6 pages.
Bhadra et al., "High Frequency electrical conduction block of the pudendal nerve," Journal of Neural Engineering—Institute of Physics Publishing, ; 2006, 8 pages.
Bhadra MD, Niloy et al., "High-Frequency Electrical Conduction Block of Mammalian Peripheral Motor Nerve," Muscle and Nerve, Dec. 2005, 9 pages.
BionicNAVIGATOR Software Guide, Part MP9055261-001, 2004, 58 pages.
Boger et al., "Bladder Voiding by Combined High Frequency Electrical Pudendal Nerve Block and Sacral Root Stimulation," Neurourology and Urodynamics, 27, 2008, 5 pages.

(56) References Cited

OTHER PUBLICATIONS

Boston Scientific "Precision™ Spinal Cord Stimulator System Clinician Manual—Directions for Use," 2015, 74 pages.
Boston Scientific, News Release: "New Data Presented at NANS 2014 Demonstrate Long-Term, Low Back Pain Relief with Boston Scientific Precision Spectra™ Spinal Cord Stimulator System," Dec. 12, 2014, 8 pages.
Bowman and McNeal, Response of Single Alpha Motoneurons to High-Frequency Pulse Trains, Appl. Neurophysiol. 49, p. 121-138, 1986, 10 pages.
Bronstein et al., "The Rationale Driving the Evolution of Deep Brain Stimulation of Constant-Current Devices," International Neuromodulation Society 2014, 5 pages.
Broseta et al., "High-Frequency cervical spinal cord stimulation in spasticity and motor disorders," Advances in Stereotactic and Functional Neurosurgery 7. Springer Verlag 1987, 6 pages.
Burton, Charles, "Dorsal Column Stimulation: Optimization of Application," Surgical Neurology, vol. 4, No. 1, Jul. 1975, 10 pages.
Butt et al., "Histological Findings Using Novel Stimulation Parameters in a Caprine Model," European Journal of Pain Supplements, 2011, 2 pages.
Cahana et al., "Acute Differential Modulation of Synaptic Transmission and Cell Survival During Exposure to Pulsed and Continuous Radiofrequency Energy," Journal of Pain, vol. 4, No. 4, May 2003, 6 pages.
Cameron et al., "Effects of posture on stimulation parameters in spinal cord stimulation," Neuromodulation: Technology at the Neural Interface 1.4, 1998, 8 pages.
Camilleri et al., "Intra-abdominal vagal blocking (VBLOC therapy): clinical results with a new implantable medical device," Surgery 143.6, 2008, 9 pages.
Crapanzano et al., "High Frequency Spinal Cord Stimulation for Complex Regional Pain Syndrome: A Case Report," Pain Physician, 2017, 6 pages.
Crosby et al., "Stimulation Parameters Define the Effectiveness of Burst Spinal Cord Stimulation in a Rat Model of Neuropathic Pain," Neuromodulation Technology at the Neural Interface, International Neurmodulation Society, 2014, 8 pages.
Cuellar et al., "Effect of High Frequency Alternating Current ; on Spinal Afferent Nociceptive Transmission," Neuromodulation: Technology at the Neural Interface, 2012, 10 pages.
Curriculum Vitae and Declaration of Dr. Ganesan Baranidharan, 4 pages, 2016.
Curriculum Vitae and Declaration of Dr. Jonathan Miller, 20 pages, Oct. 25, 2016.
Curriculum Vitae and Declaration of Dr. Simon James Thomson, Oct. 24, 2016, 2 pages.
Curriculum Vitae and Declaration of Prof. Bengt Linderoth, Oct. 21, 2016, 3 pages.
Curriculum Vitae of Michael A. Moffitt, 2015, 2 pages.
De Carolis et al., Poster: "Efficacy of Spinal Cord Stimulation (SCS) in the Treatment of Failed Back Surgery Syndrome (FBSS): a comparative study," 2013, 1 page.
De Ridder et al., U.S. Appl. No. 60/895,061, Applicant: Dirk De Ridder, filed Mar. 15, 2007, 47 pages.
Decision and Minutes: Opposition of European Patent No. 2421600 by Boston Scientific Neuromodulation Corporation, Apr. 3, 2017, 28 pages.
Declaration of Cameron C. McIntyre, Ph.D., May 6, 2015, Attorney Ref: 1014.0248AB1, 88 pages.
Declaration of Cameron C. McIntyre, Ph.D., May 6, 2015, Attorney Ref: 1014.0248AB2, 57 pages.
Declaration of Dr. Jonathan Miller on behalf of European Patent No. 2853285, 26 pages, May 16, 2017.
Declaration of M. Jason D. Rahn for European Patent No. 2243510, dated Feb. 2, 2017, 2 pages.
Declaration of M. Jason D. Rahn, Jan. 7, 2015, 7 pages.
Declaration of Prof. Bengt Linderoth for European Patent No. 2421600, dated Dec. 16, 2016 2 pages.
Deridder et al., "Are Paresthesias necessary for pain suppression in SCS—Burst Stimulation," Brain, Brain Research Center Antwerp of Innovative and Interdisciplinary Neuromodulation, 2010, 27 pages.
Deridder et al., "Burst Spinal Cord Stimulation: Toward Paresthesia-Free Pain Suppression," www.neurosurgery-online.com, vol. 66, Nos. 5, May 2010, 5 pages.
Dorland's Illustrated Medical Dictionary, Twenty-sixth Edition, "Paresthesia," 1981, 4 pages.
Doug Atkins of Medtronic Neurological, "Medtronic Neurostimulation Leads, 510(k) Summary," Submission Prepared: Feb. 27, 2004, 6 pages.
Duyvendak et al., "Spinal Cord Stimulation With a Dual Quadripolar Surgical Lead Placed in General Anesthesia is Effective in Treating Intractable Low Back and Leg Pain," Neuromodulation: Technology at the Neural Interface, vol. 10, No. 2, 2007, 7 pages.
Eddicks et al., "Thoracic Spinal Cord Stimulation Improves Functional Status and Relieves Symptoms in Patients with Refractory Angina Pectoris: The First Placebo-Controlled Randomised Study," Heart Journal, 2007, 6 pages.
European Extended Search Report for European Patent Application No. 17154846.4, Applicant: Nevro Corporation, mailed Jul. 11, 2017, 6 pages.
European Search Report for European Application No. 10160641.6, Applicant: Nevro Corporation, mailed Apr. 12, 2011, 7 pages.
European Search Report, European Application No. EP10160569, Applicant: Nevro Corporation, mailed Jun. 9, 2010, 7 pages.
Ex Parte Office Action for U.S. Appl. No. 13/446,970, First Inventor Named: Konstantinos Alataris, Mailed: Oct. 15, 2012, 9 pages.
Feeling vs. Function Poster, Mager and Associates Consulting, 2009, 1 page.
First Preliminary Amendment for U.S. Appl. No. 13/446,970, First Named Inventor: Konstantinos Alataris, Mailed: May 18, 2012, 7 pages.
Geddes, "A Short History of the electrical stimulation of excitable tissue—Including Electrotherapeutic Applications," The Physiologist, vol. 27, No. 1, Feb. 1984, 51 pages.
Grill, Warren et al., "Stimulus Waveforms for Selective Neural Stimulation," IEEE Engineering in Medicine and Biology, Jul./Aug. 1995, pp. 375-385.
Gulve et al., Poster: "10KHz High Frequency Spinal Cord Stimulation: Middlesbrough Experience," 2013, 1 page.
Guo et al., "Design and Implement of a Mini-Instrument for Rehabilitation with Transcutaneous Electrical Nerve Stimulation," School of Medical Instrument and Food Engineering, University of Shanghai for Science and Technology, Shanghai China, Mar. 31, 2007, 5 pages.
Hefferman et al., "Efficacy of Transcutaneous Spinal Electroanalgesia in Acute Postoperative Pain Management," Anesthesiology, 2001, 2 pages.
Higuchi et al., "Exposure of the Dorsal Root Ganglion in Rats to Pulsed Radiofrequency Currents Activates Dorsal Horn Lamina I and II Neurons," Neurosurgery, vol. 50, No. 4, Apr. 2002, 7 pages.
Hilberstadt et al., "The Effect of Transcutaneous Spinal Electroanalgesia upon Chronic Pain: A single case study," Physiotherapy, vol. 86 No. 3, Mar. 2000, 2 pages.
Holsheimer—Effectiveness of Spinal Cord Stimulation in the Management of Chronic Pain: Analysis of Technical Drawbacks and Solutions, Neurosurgery, vol. 40, No. 5, May 1997, pp. 990-999.
Hopp et al., "Effect of anodal blockade of myelinated fibers on vagal c-fiber afferents," American Journal Physiological Society, Nov. 1980; 239(5), 9 pages.
Hoppenstein, Reuben, "Electrical Stimulation of the Ventral and Dorsal Columns of the Spinal Cord for Relief of Chronic Intractable Pain: Preliminary Report," Surgical Neurology, vol. 4, No. 1, Jul. 1975, 9 pages.
House et al., "Safety and Efficacy of the House/3M Cochlear Implant in Profoundly Deaf Adults," Otolaryngologic Clinics of North America, vol. 19, No. 2, May 1986, 12 pages.
Huxely et al., "Excitation and Conduction in Nerve: Quantitative Analysis," Science, Sep. 11, 1964; 145: 1154-9.

(56) References Cited

OTHER PUBLICATIONS

International Neuromodulation Society 10th World Congress, Neuromodulation: Technology that Improves Patient Care, London, England, May 21-26, 2011, 385 pages.
International Search Report and Written Opinion, International Application ; No. PCT/US10/32124, Applicant: Nevro Corporation, European Patent Office, mailed Jun. 16, 2010, 28 pages.
J.P. Morgan North America Equity Research, "Nevro—Let the Launch Begin: Senza Approved, Raising PT to $54," www.jpmorganmarkets.com, May 10, 2015, 8 pages.
J.P. Morgan North America Equity Research, "Nevro—Welcome to the Future of Spinal Cord Stimulation Initiating at OW with $34 Price Target," www.jpmorganmarkets.com, Dec. 1, 2014, 39 pages.
Jacques et al., "Development of a New Implantable Bio-Telestimulator," Surg. Neurol., vol. 13, May 1980, 2 pages.
Jain et al., Abstract—"Accelerate: A Prospective Multicenter Trial Evaluating the Use of High-Rate Spinal Cord Stimulation in the Management of Chronic Intractable Pain," The American Academy of Pain Medicine, 2015, 1 page.
Jang et al., "Analysis of Failed Spinal Cord Stimulation Trails in the Treatment of Intractable Chronic Pain," J. Korean Neurosurg Soc 43, 2008, 5 pages.
Jezernik et al., "Electrical Stimulation for the Treatment of Bladder Dysfunction: Current Status and Future Possibilities," Neurological Research, vol. 24, Jul. 2002, 18 pages.
JMP Securities, "Nevro Corp. (NVRO) Initiating Coverage on Nevro Corp. with a Market Outperform Rating—Investment Highlights," Dec. 1, 2014, 42 pages.
Kapural et al., "Comparison of 10-KHz High Frequency and Traditional Low-Frequency Spinal Cord Stimulation for the Treatment of Chronic Back and Leg Pain: 24-Month Results From a Multicenter, Randomized, Controlled Pivotal Trial," Neurosurgery, vol. 79, No. 5, Nov. 2016, 11 pages.
Kapural et al., "Novel 10-Khz High Frequency Therapy (HF10 Therapy) is Superior to Traditional Low-Frequency Spinal Cord Stimulation for Treatment of Chronic Back and Leg Pain," Anesthesiology The Journal of American Society of Anesthesiologists, Inc., 2015, 11 pages.
Kilgore et al. "Nerve Conduction Block Utilizing High-Frequency Alternating Current" Medical & Biology Engineering and Computing, 2004, vol. 24, pp. 394-406.
Kilgore et al. "Reversible Nerve Conduction Block Using Kilohertz Frequency Alternating Current," Neuromodulation Technology at the Neural Interface, International Neuromodulation Society, 2013, 13 pages.
Kreitler et al., "Chapter 15: Implantable Devices and Drug Delivery Systems—The Handbook for Chronic Pain," NOVA Biomedical Books, New York, 2007, 17 pages.
Krista Oakes of Neuromed, Inc., "Implanted Spinal Cord Stimulator Lead 510(k) Summary of Safety and Effectiveness," Submission Prepared Feb. 21, 1996, 3 pages.
Kuechmann et al., Abstract #853: "Could Automatic Position Adaptive Stimulation Be Useful in Spinal Cord Stimulation?" Medtronic, Inc., Minneapolis, MN, European Journal of Pain 13, 2009, 1 page.
Kumar et al., "Spinal Cord Stimulation in Treatment of Chronic Benign Pain: Challenges in Treatment Planning and Present Status, a 22-Year Experience," Neurosurgery, vol. 58, No. 3, Mar. 2006, 16 pages.
Kumar et al., "The Effects of Spinal Cord Stimulation in Neuropathic Pain Are Sustained: A 24-month Follow-Up of the Prospective Randomized Controlled Multicenter Trial of the Effectiveness of Spinal Cord Stimulation," www.neurosurgery-online.com, vol. 63, No. 4, Oct. 2008, 9 pages.
Lambru et al., "Safety and Efficacy of Cervical 10 KHz Spinal Cord Stimulation in Chronic Refractory Primary Headaches: A Retrospective Case Series," The Journal of Headache and Pain, 2016, 8 pages.
Lempka et al., "Computational Analysis of Kilohertz Frequency Spinal Cord Stimulation for Chronic Pain Management," Anesthesiology, vol. 122, No. 6, Jun. 2015, 15 pages.

Linderoth et al., "Mechanisms of Spinal Cord Stimulation in Neuropathic and Ischemic Pain Syndromes," Neuromodulation, Chapter 25, 2009, 19 pages.
Linderoth et al., "Mechanisms of Spinal Cord Stimulation in Painful Syndromes: Role of Animal Models," Pain Medicine, vol. 7, No. S1, 2006, 13 pages.
Linderoth et al., "Physiology of Spinal Cord Stimulation: Review and Update," Neuromodulation, vol. 2, No. 3, 1999, 15 pages.
MacDonald, Alexander J. R, and Coates, Tim W., "The Discovery of Transcutaneous Spinal Electroanalgesia and Its Relief of Chronic Pain," Physiotherapy, vol. 81. No. 11, Nov. 1995, 9 pages.
Manola et al., "Technical Performance of Percutaneous Leads for Spinal Cord Stimulation: A Modeling Study," International Neuromodulation Society, 2005, 12 pages.
Mavoori et al., "An Autonomous implantable computer for neural recording and stimulation in unrestrained primates," Journal of Neuroscience Methods, 2005, 7 pages.
McCreery et al., "Charge Density and Charge Per Phase as Cofactors in Neural Injury Induced by Electrical Stimulation," IEEE Transactions on Biomedical Engineering, vol. 37, No. 10, Oct. 1990.
McCreery et al., "Damage in Peripheral Nerve from Continuous Electrical Stimulation: Comparison of Two Stimulus Waveforms," Medical and Biological Engineering and Computing, Jan. 1992, 6 pages.
McCreery et al., "Relationship between Stimulus Amplitude, Stimulus Frequency and Neural Damage During Electrical Stimulation of Sciatic Nerve of a Cat," Medical and Biological Engineering and Computing, May 1995, 4 pages.
Mediati, R.D., "Mechanisms of Spinal Cord Stimulation," Florence, Oct. 2, 2002, 31 pages.
Medtronic—Neurological Division, QuadPlus, Model 3888, Lead Kit for Spinal Cord Stimulation (SCS) Implant Manual, 1996, 33 pages.
Medtronic—Neurological Division, Resume II, Model 3587A, Lead Kit for Spinal Cord Stimulation (SCS) and Peripheral Nerve Stimulation (PNS), Implant Manual, 1996, 32 pages.
Medtronic—Neurological Division, Resume TL, Model 3986, Lead Kit for Spinal Cord Stimulation (SCS) and Peripheral Nerve Stimulation (PNS), Implant Manual, 1996, 27 pages.
Medtronic—Neurostimulation Systems: Expanding the Array of Pain Control Solutions, 1999, 6 pages.
Medtronic commercial leaflet entitled: Surgical Lead Comparison, 1999, 4 pages.
Medtronic, "Medtronic Pain Therapy—Using Neurostimulation for Chronic Pain, Information for Prescribers" 2007, 29 pages.
Medtronic, Pain Therapy Product Guide, Dec. 2008, 31 pages.
Medtronic, Pisces Quad 3487A, Pisces Quad Compact model 3887, Pisces Quad Plus 3888 Lead Kit, Implant Manual, 2008, 16 pages.
Medtronic: Spinal Cord Stimulation Systems, 2013, 4 pages.
Melzack, Ronald et al., "Pain Mechanisms: A New Theory," Science, vol. 150, No. 3699, Nov. 19, 1965, 9 pages.
Merriam Webster's Collegiate Dictionary, Tenth Edition, definition of "Implantable," 1995, 3 pages.
Meyerson et al., Mechanisms of spinal cord stimulation in neuropathic pain, Neurological Research, vol. 22, Apr. 2000, 5 pages.
Miller, Jonathan, "Neurosurgery Survival Guide—A Comprehensive Guide to Neurosurgical Diagnosis and Treatment," http://d3jonline.tripod.com/neurosurgery/, Nov. 14, 2016, 4 pages.
Miller, Jonathan, "Parameters of Spinal Cord Stimulation and Their Role in Electrical Charge Delivery: A Review," Neuromodulation: Technology at the Neural Interface, 2016, 12 pages.
Morgan Stanley Research North America, "Nevro Corp—There's Something Happening Here," Dec. 15, 2014, 12 pages.
Mosby's Medical Dictionary, 8th Edition, "Paresthesia," 2009, 3 pages.
Mounaïm et al., "New Neurostimulation Strategy and Corresponding Implantable Device to Enhance Bladder Functions," Biomedical Engineering Trends in Electronics, Communications and Software, Chapter 5, 2011, 15 pages.
Mueller et al., "The Med-El Sonatati 100 Cochlear Implant: An evaluation of its safety in adults and children," Acta Oto-Laryngologica, vol. 131, No. 5, 2011, 8 pages.

(56) References Cited

OTHER PUBLICATIONS

Muller and Hunsperger, "Helvetica Physiologica Acta—Reversible Blockierung der Erregungsleitung im Nerven durch Mittelfrequenz-Daverstrom," Schwabe & Co. Basel, vol. 25, Fasc. 1, 1967, 4 pages.
Munglani, Rajesh, "The Longer Term Effect of Pulsed Radiofrequency for Neuropathic Pain," PAIN 80, 1999, 3 pages.
Nashold et al., "Dorsal col. Stimulation for Control Pain—Preliminary Report on 30 Patients," J. Neurosurg., vol. 36, May 1972, 8 pages.
Nevro—Chronic Pain and Treatments, http://www.nevro.com/English/Patients/Chronic-Pain-and-Treatments/default.aspx; 2016, 3 pages.
Nevro—Clinical Evidence, www.nevro.com/English/Physicians/Clinical-Evidence/default.aspx, 2016, 2 pages.
Nevro—HF10™ Therapy Fact Sheet, http://www.nevro.com/English/Newsroom/Resources/default.aspx, 2015, 4 pages.
Nevro—Leadership Through Innovation, J. P. Morgan 36th Annual Healthcare Conference, Jan. 8, 2018, 21 pages.
Nevro—Physician Overview www.nevro.com English/Physicians/Physician-Overview/default.aspx, 2016, 5 pages.
Nevro—Senza System http://www.nevro.com/English/Physicians/Senza-System/default.aspx, 2016, 3 pages.
Nevro HF10 Therapy—New Hope for Chronic Back Pain and Leg Pain Sufferers, http://s21.q4cdn.com/478267292/files/doc_downloads/HF10-Therapy-New-Hope-for-Chronic-Pain.pdf, 2016, 2 pages.
Nevro Senza Patient Manual, Jan. 16, 2015, 53 pages.
Nevro Senza Physician Implant Manual, Jan. 16, 2015, 31 pages.
Nevro website: HF10 Therapy Advantages, www.nevro.com/English/Patients/HF10-Therapy-Advantages/default.aspx, 2016, 3 pages.
Nevro, PMA Approval Letter and Referenced Summary of Safety and Effectiveness Data (SSED) May 8, 2015, 60 pages.
Nevro's presentation of HF10 therapy on Nevro's website, http://www.nevro.com/English/Home/default.aspx, 2016, 2 pages.
News Release Details, "Nevro Corp. Announces Pricing of Initial Public Offering," 2014, 1 page.
NIDCD-NIH 2011, Cochlear Implant Brochure, http://www.nidcd.nih.gov/health/hearing/pages/coch.aspx, Jun. 29, 2012, 2 pages.
Non-Final Office Action for U.S. Appl. No. 12/765,747, First Named Inventor: Konstantinos Alataris, Mailed: Jul. 25, 2013, 7 pages.
Non-Final Office Acton for U.S. Appl. No. 13/245,450, First Named Inventor: Konstantinos Alataris, Mailed Nov. 18, 2011, 11 pages.
North American Neuromodulation Society—14th Annual Meeting, "Neuromodulation: Vision 2010," Dec. 2-5, 2010, 9 pages.
North American Neuromodulation Society—16th Annual Meeting, "From Innovation to Reality Syllabus," Dec. 6-9, 2012, 198 pages.
North American Neuromodulation Society—Celebrating 20 years, 18th Annual Meeting Program Book, Dec. 11-14, 2014, 28 pages.
North American Neuromodulation Society, "Today's Vision, Tomorrow's Reality—17th Annual Meeting," Dec. 5-8, 2013, 12 pages.
North American Neuromodulation, "15th Annual Meeting, Our Crystal Anniversary," Dec. 8-11, 2011, 8 pages.
North et al., "Failed Back Surgery Syndrome: 5-year Follow-Up after Spinal; Cord Stimulator Implantation," Neurosurgery, Official Journal of thogress of Neurological Surgeons, vol. 28, No. 5, May 1991, 9 pages.
North et al., "Spinal Cord Stimulation for Axial Low Back Pain," Spine, vol. 30, No. 12, 2005, 7 pages.
North et al., "Spinal Cord Stimulation for Chronic, Intractable Pain: Experience over Two Decades," Neurosurgery, vol. 32, No. 2, Mar. 1993, 12 pages.
North et al., "Spinal Cord Stimulation With Interleaved Pulses: A Randomized, Controlled Trial," vol. 10, No. 4, 2007, 9 pages.
Notice of Allowance for U.S. Appl. No. 13/245,450, First Named Inventor: Konstantinos Alataris, Mailed: Mar. 14, 2012, 8 pages.
Oakley et al., "A New Spinal Cord Stimulation System Effectively Relieves Chronic, Intractable Pain: A Multicenter Prospective Clinical Study," Neuromodulation: Technology at the Neural Interface, vol. 10, No. 3, 2007, 17 pages.
Oakley et al., "Spinal Cord Stimulation in Axial Low Back Pain: Solving the Dilemma," Pain Medicine, vol. 7, No. S1, 2006, 6 pages.
Oakley, John C., "Spinal Cord Stimulation Mechanisms of Action," ; Spine vol. 27, No. 22, copyright 2002, 10 pages.
OHSIPP Summer Newsletter, The Official Newsletter for the Ohio Society of Interventional Pain Physicians, vol. 1 Ed. 2, Summer 2010, 8 pages.
Paicius et al., "Peripheral Nerve Field Stimulation for the Treatment of Chronic Low Back Pain: Preliminary Results of Long-Term Follow-up: A Case Series," Neuromodulation: Technology at the Neural Interface, vol. 10, No. 3, 2007, 12 pages.
Palmer et al., "Transcutaneous electrical nerve stimulation and ; transcutaneous spinal electroanalgesia: A preliminary efficacy and mechanisms-based investigation," Physiotherapy, 95, 2009, 7 pages.
Partial European Search Report, European Application No. EP10160641, Applicant: Nevro Corporation, mailed Aug. 30, 2010, 3 pages.
Patent Owner's Preliminary Response for Inter Partes Review for U.S. Pat. No. 8,359,102, Case No. IPR2015-01203, Petitioner: Boston Scientific Neuromodulation Corporation, Patent Owner: Nevro Corporation, mailed Sep. 1, 2015, 70 pages.
Patent Owner's Preliminary Response for Inter Partes Review for U.S. Pat. No. 8,359,102, Case No. IPR2015-01204, Petitioner: Boston Scientific Neuromodulation Corporation, Patent Owner: Nevro Corporation, mailed Sep. 1, 2015, 63 pages.
Perruchoud et al., "Analgesic Efficacy of High-Frequency Spinal Cord Stimulation: A Randomized Double-Blind Placebo-Controlled Study," Neuromodulation: Technology at Neural Interface, International Neuromodulation Society, 2013, 7 pages.
Petition for Inter Partes Review of Claims 1, 2, 11-15, 17-23, 25 and 26 for U.S. Pat. No. 8,359,102, Petitioner: Boston Scientific Neuromodulation Corporation, Patent Owner: Nevro Corporation, Attorney Ref: 1014.0248AB2, May 14, 2015, 45 pages.
Petition for Inter Partes Review of Claims 1, 2, 11-15, 17-23, 25 and 26 for U.S. Pat. No. 8,359,102, Petitioner: Boston Scientific Neuromodulation Corporation, Patent Owner: Nevro Corporation, Attorney Ref: 1014.0248AB1, May 14, 2015, 67 pages.
Prausnitz et al., "The Effects of Electric Current Applied to Skin: A Review for Transdermal Drug Delivery," Advanced Drug Delivery Reviews 18, ; 1996, 31 pages.
Precision—Physician System Handbook, Advanced Bionic Corporation, Part 9055253-0001, 2005, 92 pages.
Precision—Physician Trail Kit Insert, Advanced Bionic Corporation, Part 9055258-0001, 2005, 2 pages.
Precision Spinal Cord Stimulation—Charging System Insert, Advanced Bionic Corporation, Part 9055074-0001, 2004, 2 pages.
Precision Spinal Cord Stimulation—Charging System, Advanced Bionic Corporation, Part 9055259-0001, 2004, 2 pages.
Precision Spinal Cord Stimulation—Patient System Handbook, Advanced Bionic Corporation, Part 9055072-0001, 2004, 93 pages.
Precision Spinal Cord Stimulation—Patient Trial Journal, Advanced Bionic Corporation, Part 9055260-0001, 2004, 10 pages.
Precision Spinal Cord Stimulation—Physician Implant Manual, Advanced Bionic Corporation, Part 9055255-0001, 2005, 70 pages.
Precision Spinal Cord Stimulation—Physician Implant Manual, Advanced Bionic Corporation, Part 9055100, 2004, 62 pages.
Precision Spinal Cord Stimulation—Physician Lead Manual, Advanced Bionic Corporation, Part No. 9055183-001, May 2004, 31 pages.
Precision Spinal Cord Stimulation—Physician Lead Manual, Advanced Bionic Corporation, Part 9055095, 2004, 62 pages.
Precision Spinal Cord Stimulation—Physician Lead Manual, Advanced Bionic Corporation, Part 9055256-0001, 2005, 56 pages.
Precision Spinal Cord Stimulation—Physician Trail Handbook, Advanced Bionic Corporation, Part 9055254-0001, 2005, 66 pages.
Precision Spinal Cord Stimulation—Physician Trail Kit Model SC-7005, Part 9055066-001, Advanced Bionic Corporation, 2004, 2 pages.
Precision Spinal Cord Stimulation—Remote Control Model SC-5200, Part 9055107-001, 2004, Advanced Bionic Corporation, 2 pages.
Precision Spinal Cord Stimulation—Remote Control Model SC-5210, Advanced Bionic Corporation, Part 9055257-001, 2005, 2 pages.

(56) References Cited

OTHER PUBLICATIONS

Precision Spinal Cord Stimulation System—Patient System Handbook, Advanced Bionic Corporation, Part No. 9055184-001, May 2004, 86 pages.
Precision Spinal Cord Stimulation System, Patient Trial Handbook, Part 9055078, 2004, 74 pages.
Pudenz et al., "Development of an Implantable Telestimulator," Proc. 4th Ann. Nat'l Conf. Neuroelectric Soc., Mar. 10-12, 1971, 111-12 (Wulfsohn, Norman L. and Anthony Sances, Jr. (eds.) 1971, 4 pages.
Pudenz et al., "Neural Stimulation: Clinical and Laboratory Experiences", Surg. Neurol, 39:235-242 (1993).
Rapcan et al., Clinical Study, "High-Frequency—Spinal Cord Stimulation," Indexed and Abstracted in Science Citation Index Expanded and in Journal Citation Reports, 2015, 3 pages.
Reddy et al., "Comparison of Conventional and Kilohertz Frequency Epidural Stimulation in Patients Undergoing Trailing for Spinal Cord Stimulation: Clinical Considerations," World Neurosurgery, www.sciencedirect.com, 6 pages, 2015.
Remedi Pain Relief—ENM (Electronic Nerve Modulation), https://web.archive.org/web/20050906181041/http://www.remediuk.com/trials.htm, 2005, 5 pages.
Renew Neurostimulation System—Clinician's Manual—Advanced Neuromodulation Systems, Life Gets Better, 2000, 77 pages.
Resume of Jason D. Rahn, Jan. 7, 2015, 2 pages.
Robb et al., "Transcutaneous Electrical Nerve Stimulation vs. Transcutaneous Spinal Electroanalgesia for Chronic Pain Associated with ; Breast Cancer Treatments," Journal of Pain and Symptom Management, vol. 33, No. 4, Apr. 2007, 10 pages.
Rosenblueth et al., "The Blocking and Deblocking Effects of Alternating Currents on Nerve," Department of Physiology in Harvard Medical School, Nov. 1938, 13 pages.
Royle, John., "Transcutaneous Spinal Electroanalgesia and Chronic Pain," Physiotherapy, vol. 86, No. 5, May 2000, 1 page.
Schulman et al., "Battery Powered BION FES Network," Proceedings of the 26th Annual Conference of the IEEE EMBS, San Francisco, CA., Sep. 1-5, 2004, 4 pages.
Science Daily, "Chronic Pain Costs U.S. up to $635 billion, study shows," www.sciencedaily.com/releases/2012/09/120911091100.htm, Sep. 11, 2012, 2 pages.
Senza Spinal Cord Stimulation (SCS) System—P130022, http://www.fda.gov/MedicalDevices/ProductsandMedicalProcedures/DeviceApprovalsandClearanc es/Recently-ApprovedDevices/ucm449963.htm Oct. 14, 2016, 2 pages.
Sharan et al., "Evolving Patterns of Spinal Cord Stimulation in Patients Implanted for Intractable Low Back and Leg Pain," International Neuromodulation Society, vol. 5, No. 3, 2002, 13 pages.
Shealy et al., "Dorsal Column Electrohypalgesia," Jul. 1969, 8 pages.
Shealy MD, C. Norman et al., "Electrical Inhibition of Pain by Stimulation of the Dorsal Columns: Preliminary Clinical Report," Anesthesia and Analgesia Current Researches, vol. 446, No. 4, Jul.-Aug. 1967, 3 pages.
Shelden et al., "Depolarization in the Treatment of Trigeminal Neuralgia," Evaluation of Compression and Electrical Methods, Clinical Concept of Neurophysiological Mechanism, 1966, 8 pages.
Shelden et al., "Development and Clinical Capabilities of a New Implantable Biostimulator," The American J. of Surgery, vol. 124, Aug. 1972, 6 pages.
Shelden et al., Electrical Control of Facial Pain, Am. J. of Surgery, vol. 114, Aug. 1967, 6 pages.
Shelden et al., "Electrical stimulation of the nervous system," Surg. Neurol. vol. 4, No. 1, Jul. 1975, 6 pages.
Simpson et al., "A Randomized, Double-Blind, Crossover Study of the Use of Transcutaneous Spinal Electroanalgesia in Patients with Pain from ; Chronic Critical Limb Ischemia," Journal of Pain and Symptom Management, vol. 28, No. 5, Nov. 2004, 6 pages.
Simpson, BA "Spinal Cord Stimulation in 60 cases of Intractable Pain." Journal of Neurology, Neurosurgery and Psychiatry, 1991; 54 pp. 196-199.

Simpson, BA, "Spinal Cord Stimulation." British Journal of Neurosurgery, 1997, Feb. 11 (1), 5-11, 7 pages.
Sluijter et al., "The Effects of Pulsed Radiofrequency Fields Applied to the Dorsal Root Ganglion—A Preliminary Report," The Pain Clinic, vol. 11, No. 2, 1998, 12 pages.
Smet et al,., "Successful Treatment of Low Back Pain with a Novel Neuromodulation Device," AZ Nikolaas, 12 pages.
Smet et al., Poster: "High-Frequency Spinal Cord Stimulation at 10 KHz after Failed Traditional Spinal Cord Stimulation," NANS, 2013, 1 page.
Solomonow et al., "Control of Muscle Contractile Force through Indirect High-Frequency Stimulation," AM Journal of Physical Medicine, 1983, vol. 62, No. 3, pp. 71-82.
St. Jude Medical, "Clinician's Manual—Percutaneous Lead Kit, Models 3143, 3146, 3149, 3153, 3156, 3159, 3183, 3186, 3189," 2016, 24 pages.
St. Jude Medical, "Eon Mini™ Rechargeable IPG," Apr. 29, 2013, 3 pages.
St. Jude Medical, "Individualized Therapy through Diverse Lead Options," 2008, 6 pages.
Stimwave, News Release: "Stimwave Receives FDA Approval for High Frequency IDE," http://stimwave.com/newsroom/latest-news, Jun. 9, 2015, 2 pages.
Struijk et al., "Recruitment of Dorsal Column Fibers in Spinal Cord Stimulation: Influence of Collateral Branching," IEEE Transactions on Biomedical Engineering, vol. 39, No. 9, Sep. 1992, 10 pages.
Summons to Attend Oral Proceedings pursuant to Rule 115(1) EPC for European Patent No. 2207587, Applicant: Nevro Corporation, mailed Mar. 9, 2018, 15 pages.
Sweet et al., "Paresthesia-Free High Density Spinal Cord Stimulation for Postlaminectomy Syndrome in a Prescreened Population: A Prospective Case Series," Neuromodulation: Technology at the Neural Interface, 2015, 7 pages.
Swigris et al., "Implantable Spinal Cord Stimulator to Treat the Ischemic Manifestations of Thromboangiitis Obliterans (Buerger's disease)," Journal of Vascular Surgery, vol. 29, No. 5, 1998, 8 pages.
Tan et al., "Intensity Modulation: A Novel Approach to Percept Control in Spinal Cord Stimulation," Neuromodulation Technology at the Neural Interface, International Neuromodulation Society 2015, 6 pages.
Tanner, J.A., "Reversible blocking of nerve conduction by alternating-current; excitation," Nature, Aug. 18, 1962; 195: 712-3.
Taylor et al., "The Cross Effectiveness of Spinal Cord Stimulation in the Treatment of Pain: A Systematic Review of the Literature," Journal of Pain and Symptom Management, vol. 27, No. 4., Apr. 2001, 9 pages.
Tesfaye et al., "Electrical Spinal Cord Stimulation for Painful Diabetic Peripheral Neuropathy," The Lancet, vol. 348, Dec. 21-28, 1996, 4 pages.
Thompson et al., "A double blind randomised controlled clinical trial on the effect of transcutaneous spinal electroanalgesia (TSE) on low back pain," European Journal of Pain, vol. 12, Issue 3, Apr. 2008, 6 pages.
Tiede et al., "Novel Spinal Cord Stimulation Parameters in Patients with Predominate Back Pain," Neuromodulation: Technology at the Neural Interface, 2013, 6 pages.
Tollison et al., "Practical Pain Management; Neurostimulation Techniques," Chapter 12, Lippincott Williams and Wilkins, Third Edition, 2002, 13 pages.
Towell et al., "High Frequency non-invasive stimulation over the spine: Effects on mood and mechanical pain tolerance in normal subjects," Behavioral Neurology, vol. 10, 1997, 6 pages.
Urban et al., "Percutaneous epidural stimulation of the spinal cord for relief of pain—Long Term Results," Journal of Neurosurgery, vol. 48, ; Mar. 1978, 7 pages.
Van Butyen et al., "High Frequency Spinal Cord Stimulation for the Treatment of Chronic Back Pain Patients: Results of a Prospective Multicenter European Clinical Study," Neuromodulation Technology at the ; Neural Interface, International Neuromodulation Society, 2012, 8 pages.
Van Buyten et al., "Pain Relief for Axial Back Pain Patients," INS Meeting Poster, 1 page.

(56) References Cited

OTHER PUBLICATIONS

Van Den Honert et al. "Generation of Unidirectionally Propagated Action Potentials Nerve by Brief Stimuli" Science, vol. 26, pp. 1311-1312.
Van Den Honert, Mortimer JT, "A Technique for Collision Block of Peripheral; Nerve: Frequency Dependence," MP-11 IEEE Trans. Biomed, Eng. 28: 379-382, 1981.
Van Havenbergh et al., "Spinal Cord Stimulation for the Treatment of Chronic Back Pain Patients: 500-Hz vs. 1000-Hz Burst Stimulation," Neuromodulation: Technology at the Neural Interface, International Neurmodulation Society, 2014, 4 pages.
Verrills et al., "Peripheral Nerve Field Stimulation for Chronic Pain: 100 Cases and Review of the Literature," Pain Medicine, 2011, 11 pages.
Verrills et al., "Salvaging Failed Neuromodulation Implants with Nevro High Frequency Spinal Cord System," NANS Poster, 2013, 1 page.
Von Korff et al., "Assessing Global Pain Severity by Self-Report in Clinical and Health Services Research," Spine, vol. 25, No. 24, 2000, 12 pages.
Wallace et al., Poster: "Accelerate: A Prospective Multicenter Trial Evaluating the Use of High-Rate Spinal Cord Stimulation in the Management of Chronic Intractable Pain," Boston Scientific Corporation, 2015, 1 page.
Ward et al., "Electrical Stimulation Using Kilohertz-Frequency Alternating Current," Journal of the American Physical Therapy Association, vol. 89, No. 2, Feb. 2009, 12 pages.
Ward et al., "Variation in Motor Threshold with Frequency Using KHz Frequency Alternating Current," Muscle and Nerve, Oct. 2001, 9 pages.
Webster's Third New International Dictionary of the English Language Unabridged, "Paresthesia," 1993, 3 pages.
Weinberg et al., "Increasing the oscillation frequency of strong magnetic fields above 101 kHz significantly raises peripheral nerve excitation thresholds," Medical Physics Letter, May 2012, 6 pages.
Wesselink et al., Analysis of Current Density and Related Parameters in Spinal Cord Stimulation, IEEE Transaction on Rehabilitation Engineering vol. 6, No. 2, Jun. 1998, 8 pages.
Wolter et al., "Continuous Versus Intermittent Spinal Cord Stimulation: An Analysis of Factors Influencing Clinical Efficacy," Neuromodulation: Technology at Neural Interface, www.neuromodulationjournal.com, 2011, 8 pages.
Woo MY, Campbell B. "Asynchronous Firing and Block of Peripheral Nerve Conduction by 20KC Alternating Current," Los Angeles Neuro Society, 1964, June; 87-94, 5 pages.
Yearwood et al., "A Prospective Comparison of Spinal Cord Stimulation (SCS) Using Dorsal Column Stimulation (DCS), Intraspinal Nerve Root Stimulation (INRS), and Varying Pulse Width in the Treatment of Chronic Low Back Pain," Congress of Neurological Surgeons 56th Annual Meeting, Oct. 7-12, 2006, 2 pages.
Yearwood et al., "Pulse Width Programming in Spinal Cord Stimulation: A Clinical Study," Pain Physician Journal, Jul./Aug. 2010, 16 pages.
Yearwood et al., Case Reports: "A Prospective Comparison of Spinal Cord Stimulation (SCS) Using Dorsal col. Stimulation (DCS), Intraspinal Nerve Root Stimulation (INRS), and Varying Pulse Width in the Treatment of Chronic Low Back Pain," Presented at the Congress of Neurological Surgeons 56th Annual Meeting, Oct. 7-12, 2006, 7 pages.
Zhang et al., "Simulation Analysis of Conduction Block in Myelinated Axons Induced by High-Frequency Biphasic Rectangular Pulses," IEEE Transactions on Biomedical Engineering, vol. 53., No. 7, Jul. 2006, 4 pages.
Zhang et al., Changes Across Time in Spike Rate and Spike Amplitude of Auditory Nerve Fibers Stimulated by Electric Pulse Trains, Journal of the Association for Research of Otolaryngology, 2007, 17 pages.

Brief for Plaintiff-Appellant Nevro Corp., *Nevro Corp. vs. Boston Scientific Corporation and Boston Scientific Neuromodulation Corporation*, Case No. 3:16-cv-06830-VC-MEJ, filed Nov. 8, 2018, 341 pages.
Boston Scientific's Response to the Summons to Attend Oral Proceedings for European Patent No. 2853285, *Nevro Corp. vs. Boston Scientific Corporation and Boston Scientific Neuromodulation Corporation and Medtronic, Inc*, filed Nov. 30, 2018, 5 pages.
Clinicaltrials.gov, "Safety and Effectiveness Study of the Precision SCS System Adapted for High-Rate Spinal Cord Stimulation (ACCELERATE)," https://clinicaltrials.gov/ct2/show/NCT02093793?term=boston+scientific&recr=Open&cond=%22Pain%22&rank=3, Feb. 2015, 3 pages.
Medtronic's Response to the Summons to Attend Oral Proceedings for European Patent No. 2853285, *Nevro Corp. vs. Boston Scientific Neuromodulation Corporation and Medtronic, Inc.*, filed Nov. 30, 2018, 8 pages.
Decision Rejecting the Opposition (Art. 101(2) EPC) for European Patent No. 2207587, *Nevro Corp. vs. Boston Scientific Neuromodulation Corporation and Medtronic, Inc.*, Jan. 4, 2019, 18 pages.
Provision of Minutes in accordance with Rule 124(4) EPC for Opposition by Medtronic, Inc., and Boston Scientific Neuromodulation Corporation for European Patent No. 2207587, mailed Jan. 4, 2019, 10 pages.
Medtronic—Spinal Cord Stimulation (SCS) Patient Management Guidelines for Clinicians, 1999, 114 pages.
Medtronic's Submissions Commenting on the Auxiliary Requests for European Patent No. 2853285, *Nevro Corp. vs. Boston Scientific Neuromodulation Corporation and Medtronic, Inc*, filed Jan. 11, 2019, 13 pages.
Nevro—Leadership Through Innovation, J. P. Morgan 36th Annual Healthcare Conference, Jan. 24, 2019, 2 pages.
Notice of Opposition for European Patent No. 3156099, Proprietor of the Patent: Nevro Corporation; Opponent: Medtroni, Inc., Mar. 11, 2019, 31 pages.
Opponent Response to Patent Proprietor Comments to Declaration of Dr. Baranidharan for European Patent No. 2630984, mailed Nov. 8, 2016, 3 pages.
Opponents Medtronic, Inc.: Response to Grounds of Appeal for European Patent No. 2630984, mailed Dec. 19, 2017, 23 pages.
Opponents Boston Scientific Neuromodulation Corporation.: Statement Setting Out the Grounds of Appeal for European Patent No. 2207587, mailed May 2, 2019, 12 pages.
Opponents Medtronic, Inc.: Statement Setting Out the Grounds of Appeal for European Patent No. 2207587, mailed May 19, 2019, 21 pages.
Nevro Observations and Response to Notice of Oppositions filed by Medtronic Inc., and Boston Scientific for European Patent No. 2586488, mailed May 18, 2018, 87 pages.
Opponents Boston Scientific Neuromodulation Corporation: Response to Appeal in Opposition for European Patent No. 2243510, mailed May 2, 2018, 31 pages.
Opponents Medtronic, Inc.: Response to Appeal in Opposition for European Patent No. 2243510, mailed Apr. 30, 2018, 23 pages.
Additional Arguments to Notice of Opposition of European Patent No. 2853285, filed by Medtronic, Inc., on May 17, 2017, 9 pages.
Boston Scientific's Response to the Summons to Attend Oral Proceedings for European Patent No. 2207587, *Nevro Corp. vs. Boston Scientific Neuromodulation Corporation*, filed Sep. 6, 2018, 31 pages.
Reply of the Patent Proprietor, Nevro Corporation for European Patent No. 2207587, Opponent 1: Medtronic, Inc., and Opponent 2: Boston Scientific Neuromodulation Corporation, mailed Sep. 25, 2019.
Declaration of Rafael Carbunaru in Support of Boston Scientific's Invalidity Contentions, *Nevro Corp.* (Plaintiff) vs. *Boston Scientific Corporation and Boston Scientific Neuromodulation Corporation*, Case No. 3:16-cv-06830-VC, executed Mar. 17, 2017, 5 pages.
Exhibit A of Declaration of Rafael Carbunaru: "Physician Implant Manual—Precision," in Support in Support of Defendants Boston Scientific Corporation's and Boston Scientific Neuromodulation Corporation's Invalidity Contentions, Advanced Bionics, 2004, 62 pages.

(56) References Cited

OTHER PUBLICATIONS

Exhibit B of Declaration of Rafael Carbunaru: "Physician Lead Manual—Precision," in Support in Support of Defendants Boston Scientific Corporation's and Boston Scientific Neuromodulation Corporation's Invalidity Contentions, Advanced Bionics, 2004, 62 pages.
Exhibit C of Declaration of Rafael Carbunaru: "Patient System Handbook—Precision," in Support in Support of Defendants Boston Scientific Corporation's and Boston Scientific Neuromodulation Corporation's Invalidity Contentions, Advanced Bionics, 2004, 93 pages.
Plaintiff Nevro Corp's Motion to Strike Inequitable Conduct Allegations From Defendants' Twelfth Affirmative Defense; Memorandum of Points and Authorities, *Nevro Corp.* vs. *Boston Scientific Corporation and Boston Scientific Neuromodulation Corporation*, Case No. 3:16-cv-06830-VC, Aug. 3, 2017, 10 pages.
Boston Scientific's Opposition to Nevro's Motion to Strike Inequitable Conduct Allegations from Defendants' Twelfth Affirmative Defense (ECF No. 172), *Nevro Corp.* vs. *Boston Scientific Corporation and Boston Scientific Neuromodulation Corporation*, Case No. 3:16-cv-06830-VC, Aug. 17, 2017, 17 pages.
Non-Confidential Opening Brief of Appellant Stimwave Technologies, Inc. for Plaintiff-Appellee: *Nevro Corp* vs. Defendant-Appellant: *Stimwave Technologies, Inc.*, United States Court of Appeals for Federal Circuit, Case 19-CV-325, filed Sep. 24, 2019, 156 pages.
Principal and Response Brief for Defendants-Cross-Appellants Boston Scientific Corporation's and Boston Scientific Neuromodulation Corporation's, *Nevro Corp.* v. *Boston Scientific Corporation and Boston Scientific Neuromodulation Corporation*, Case No. 3:16-cv-06830-VC (N.D. Cal.), Jan. 17, 2019, 71 pages.
Reply Brief for Defendants-Cross-Appellants Boston Scientific Corporation's and Boston Scientific Neuromodulation Corporation's, *Nevro Corp.* v. *Boston Scientific Corporation and Boston Scientific Neuromodulation Corporation*, Case No. 3:16-cv-06830-VC (N.D. Cal.), Jun. 3, 2019, 26 pages.
Response and Reply Brief for Plaintiff-Appellant Nevro Corp., *Nevro Corp.* v. *Boston Scientific Corporation and Boston Scientific Neuromodulation Corporation*, Case No. 3:16-cv-06830-VC (N.D. Cal.), Apr. 12, 2019, 68 pages.
Memorandum Opinion, Plaintiff: *Nevro Corp.* vs. Defendant-Appellant: *Stimwave Technologies, Inc.*, United States Court for the District of Delaware, Civil Action No. 19-325-CFC, Case 19-CV-325, filed Jul. 24, 2019, 46 pages.
Summons to Attend Oral Proceedings pursuant to Rule 115(1) EPC for European Patent No. 3156099, Applicant: Nevro Corporation, mailed Nov. 22, 2019, 21 pages.
Siegel et al., "Prospective Randomized Feasibility Study Assessing the Effect of Cyclic Sacral Neuromodulation on Urinary Urge Incontinence in Women," Female Pelvic Med Reconstr Surg. 2018, 5 pages.
Cadish, "Stimulation Latency and Comparison of Cycling Regimens in Women Using Sacral Neuromodulation," Feb. 1, 2016, 4 pages.
Cappaert et al., "Efficacy of a New Charge-Balanced Biphasic Electrical Stimulus in the Isolated Sciatic Nerve and the Hippocampal Slice," International Journal of Neural Systems, vol. 23, No. 1, 2013, 16 pages.
Hofmann et al., "Modified Pulse Shapes for Effective Neural Stimulation," Frontiers in Neuroengineering, Sep. 28, 2011, 10 pages.
Petition for Inter Partes Review of U.S. Pat. No. 9,333,357, Case No. IPR2021-01023, Petitioner: Nalu Medical, Inc.; Patent Owner: Nevro Corporation, May 27, 2021, 117 pages.
Exhibit 1002—"File History of U.S. Pat. No. 9,333,357," Petition for Inter Partes Review of U.S. Pat. No. 9,333,357, Case No. IPR2021-01023, Petitioner: Nalu Medical, Inc.; Patent Owner: Nevro Corporation, May 27, 2021, 454 pages.
Exhibit 1003—Declaration of Dr. Gerald E. Loeb, M.D. in Support of Petition for Inter Partes Review of U.S. Pat. No. 9,333,357, Case No. IPR2021-01023, Petitioner: Nalu Medical, Inc.; Patent Owner: Nevro Corporation, May 27, 2021, 166 pages.
Exhibit 1004—"Curriculum Vitae of Gerald E. Loeb, M.D.," in Support of Petition for Inter Partes Review of U.S. Pat. No. 9,333,357, Case No. IPR2021-01023, Petitioner: Nalu Medical, Inc.; Patent Owner: Nevro Corporation, May 27, 2021, 39 pages.
Exhibit 1007—Declaration of Thomas L. Yearwood M.D., Ph.D. in Support of Petition for Inter Partes Review of U.S. Pat. No. 9,333,357, Case No. IPR2021-01023, Petitioner: Nalu Medical, Inc.; Patent Owner: Nevro Corporation, May 27, 2021, 10 pages.
Exhibit 1008—"Curriculum Vitae of Thomas L. Yearwood M.D., Ph.D.—Apr. 16, 2021," in Support of Petition for Inter Partes Review of U.S. Pat. No. 9,333,357, Case No. IPR2021-01023, Petitioner: Nalu Medical, Inc.; Patent Owner: Nevro Corporation, May 27, 2021, 8 pages.
Exhibit 1009—"United States Food and Drug Administration Premarket Approval ("PMA") Documents for PMA No. P030017, Precisiontm Spinal Cord Stimulation (SCS) System, dated Apr. 27, 2004 ("Precision SCS PMA")—Apr. 27, 2004" in Support of Petition for Inter Partes Review of U.S. Pat. No. 9,333,357, Case No. IPR2021-01023, Petitioner: Nalu Medical, Inc.; Patent Owner: Nevro Corporation, May 27, 2021, 8 pages.
Exhibit 1016—"Nakamura, S., Takahashi, K., Takahashi, Y., Yamagata, M., Moriya, H., The Afferent Pathways of Discogenic Low-Back Pain, 1996." in Support of Petition for Inter Partes Review of U.S. Pat. No. 9,333,357, Case No. IPR2021-01023, Petitioner: Nalu Medical, Inc.; Patent Owner: Nevro Corporation, May 27, 2021, 7 pages.
Exhibit 1017—"DKT. 185-1 Sep. 21, 2017 Ex. A Nevro Proposed Claim Construction, No. 3:16-cv-06830-VC." in Support of Petition for Inter Partes Review of U.S. Pat. No. 9,333,357, Case No. IPR2021-01023, Petitioner: Nalu Medical, Inc.; Patent Owner: Nevro Corporation, May 27, 2021, 118 pages.
Exhibit 1018—"Villavicencio et al.—Laminectomy versus Percutaneous Electrode Placement for Spinal Cord Stimulation—2000" in Support of Petition for Inter Partes Review of U.S. Pat. No. 9,333,357, Case No. IPR2021-01023, Petitioner: Nalu Medical, Inc.; Patent Owner: Nevro Corporation, May 27, 2021, 8 pages.
Exhibit 1020—"Demand for Jury Trial—Nevro First Amended Complaint, DKT. 14, Nevro v. Nalu, Case No. C.A. No. 20-291—Jun. 1, 2020" in Support of Petition for Inter Partes Review of U.S. Pat. No. 9,333,357, Case No. IPR2021-01023, Petitioner: Nalu Medical, Inc.; Patent Owner: Nevro Corporation, May 27, 2021, 36 pages.
Exhibit 1021—"North et al.—History of Spinal Cord Stimulation—2018" in Support of Petition for Inter Partes Review of U.S. Pat. No. 9,333,357, Case No. IPR2021-01023, Petitioner: Nalu Medical, Inc.; Patent Owner: Nevro Corporation, May 27, 2021, 10 pages.
Exhibit 1026—"2006 Program of Annual Meeting of Congress of Neurological Surgeons, Oct. 7-12, 2006" in Support of Petition for Inter Partes Review of U.S. Pat. No. 9,333,357, Case No. IPR2021-01023, Petitioner: Nalu Medical, Inc.; Patent Owner: Nevro Corporation, May 27, 2021, 84 pages.
Exhibit 1027—"Medtronic—Itrel EZ Model 7434A Patient Programmer User Manual" in Support of Petition for Inter Partes Review of U.S. Pat. No. 9,333,357, Case No. IPR2021-01023, Petitioner: Nalu Medical, Inc.; Patent Owner: Nevro Corporation, May 27, 2021, 154 pages.
Exhibit 1028—"Federal Register / vol. 69, No. 189 / Sep. 30, 2004" in Support of Petition for Inter Partes Review of U.S. Pat. No. 9,333,357, Case No. IPR2021-01023, Petitioner: Nalu Medical, Inc.; Patent Owner: Nevro Corporation, May 27, 2021, 3 pages.
Exhibit 1029—"Erickson DL.—Percutaneous trial of stimulation for patient selection for implantable stimulating devices. J Neurosurg. 1975" in Support of Petition for Inter Partes Review of U.S. Pat. No. 9,333,357, Case No. IPR2021-01023, Petitioner: Nalu Medical, Inc.; Patent Owner: Nevro Corporation, May 27, 2021, 5 pages.
Exhibit 1030—"North et al.—Chronic stimulation via percutaneously inserted epidural electrodes. Neurosurgery. 1977" in Support of Petition for Inter Partes Review of U.S. Pat. No. 9,333,357, Case No. IPR2021-01023, Petitioner: Nalu Medical, Inc.; Patent Owner: Nevro Corporation, May 27, 2021, 4 pages.

(56) References Cited

OTHER PUBLICATIONS

Petition for Inter Partes Review for U.S. Pat. No. 8,892,209—IPR2022-00510, *Boston Scientific Corporation and Boston Scientific Neuromodulation Corporation* (Petitioners) v. *Nevro Corporation* (Patent Owner), Filed Feb. 10, 2022, 102 pages.
Petitioner' Statement on Parallel Petitions for U.S. Pat. No. 8,892,209—IPR2022-00510, *Boston Scientific Corporation and Boston Scientific Neuromodulation Corporation* (Petitioners) v. *Nevro Corporation* (Patent Owner), Filed Feb. 10, 2022, 7 pages.
Petitioner' Updated Exhibit List for U.S. Pat. No. 8,892,209—IPR2022-00510, *Boston Scientific Corporation and Boston Scientific Neuromodulation Corporation* (Petitioners) v. *Nevro Corporation* (Patent Owner), Filed Feb. 14, 2022, 10 pages.
Patent Owner's Mandatory Notices for U.S. Pat. No. 8,892,209—IPR2022-00510, *Boston Scientific Corporation and Boston Scientific Neuromodulation Corporation* (Petitioners) v. *Nevro Corporation* (Patent Owner), Filed Feb. 25, 2022, 5 pages.
Petition for Inter Partes Review for U.S. Pat. No. 8,892,209—IPR2022-00509, *Boston Scientific Corporation and Boston Scientific Neuromodulation Corporation* (Petitioners) v. *Nevro Corporation* (Patent Owner), Filed Feb. 7, 2022, 95 pages.
Petitioner' Statement on Parallel Petitions for U.S. Pat. No. 8,892,209—IPR2022-00509, *Boston Scientific Corporation and Boston Scientific Neuromodulation Corporation* (Petitioners) v. *Nevro Corporation* (Patent Owner), Filed Feb. 7, 2022, 7 pages.
Petitioner' Updated Exhibit List for U.S. Pat. No. 8,892,209—IPR2022-00509, *Boston Scientific Corporation and Boston Scientific Neuromodulation Corporation* (Petitioners) v. *Nevro Corporation* (Patent Owner), Filed Feb. 14, 2022, 10 pages.
Patent Owner's Mandatory Notices for U.S. Pat. No. 8,892,209—IPR2022-00509, *Boston Scientific Corporation and Boston Scientific Neuromodulation Corporation* (Petitioners) v. *Nevro Corporation* (Patent Owner), Filed Feb. 25, 2022, 5 pages.
Exhibit 1007: Declaration of Marom Bikson, Ph. D., Feb. 10, 2022, 191 pages for Petition for Inter Partes Review for U.S. Pat. No. 8,892,209—IPR2022-00510 and Petition for Inter Partes Review for U.S. Pat. No. 8,892,209—IPR2022-00509, *Boston Scientific Corporation and Boston Scientific Neuromodulation Corporation* (Petitioners) v. *Nevro Corporation* (Patent Owner).
Exhibit 1008: Curriculum Vitae of Marom Bikson, Ph.D., 72 pages, for Petition for Inter Partes Review for U.S. Pat. No. 8,892,209—IPR2022-00510 and Petition for Inter Partes Review for U.S. Pat. No. 8,892,209—IPR2022-00509, *Boston Scientific Corporation and Boston Scientific Neuromodulation Corporation* (Petitioners) v. *Nevro Corporation* (Patent Owner).
Exhibit 1022: Declaration of Natalie Bryan, Feb. 7, 2022, 15 pages, for Petition for Inter Partes Review for U.S. Pat. No. 8,892,209—IPR2022-00510 and Petition for Inter Partes Review for U.S. Pat. No. 8,892,209—IPR2022-00509, *Boston Scientific Corporation and Boston Scientific Neuromodulation Corporation* (Petitioners) v. *Nevro Corporation* (Patent Owner).
Exhibit 1024: Declaration of Thomas L. Yearwood, M.D., Ph.D., 13 pages, for Petition for Inter Partes Review for U.S. Pat. No. 8,892,209—IPR2022-00510 and Petition for Inter Partes Review for U.S. Pat. No. 8,892,209—IPR2022-00509, *Boston Scientific Corporation and Boston Scientific Neuromodulation Corporation* (Petitioners) v. *Nevro Corporation* (Patent Owner).
Exhibit 1036: Declaration of Michael Henry Verdolin, M.D. Feb. 7, 2022, 30 pages, for Petition for Inter Partes Review for U.S. Pat. No. 8,892,209—IPR2022-00510 and Petition for Inter Partes Review for U.S. Pat. No. 8,892,209—IPR2022-00509, *Boston Scientific Corporation and Boston Scientific Neuromodulation Corporation* (Petitioners) v. *Nevro Corporation* (Patent Owner).
Exhibit 1037: Curriculum Vitae of Michael Henry Verdolin, M.D, for Petition for Inter Partes Review for U.S. Pat. No. 8,892,209—IPR2022-00510 and Petition for Inter Partes Review for U.S. Pat. No. 8,892,209—IPR2022-00509, *Boston Scientific Corporation and Boston Scientific Neuromodulation Corporation* (Petitioners) v. *Nevro Corporation* (Patent Owner).
Exhibit 1081: Inter Partes Review 2021-01023 for U.S. Pat. No. 9,333,357—Patent Owner's Preliminary Response, *Nalu Medical, Inc.* v. *Nevro Corp.*, Sep. 16, 2021, 85 pages, for Petition for Inter Partes Review for U.S. Pat. No. 8,892,209—IPR2022-00510 and Petition for Inter Partes Review for U.S. Pat. No. 8,892,209—IPR2022-00509, *Boston Scientific Corporation and Boston Scientific Neuromodulation Corporation* (Petitioners) v. *Nevro Corporation* (Patent Owner).
Exhibit 1083: Curriculum Vitae of Thomas L. Yearwood, M.D, for Petition for Inter Partes Review for U.S. Pat. No. 8,892,209—IPR2022-00510 and Petition for Inter Partes Review for U.S. Pat. No. 8,892,209—IPR2022-00509, *Boston Scientific Corporation and Boston Scientific Neuromodulation Corporation* (Petitioners) v. *Nevro Corporation* (Patent Owner).
Exhibit 1092: Patent Owner's Contingent Motion to Amend for Inter Partes Review 2020-01562 for U.S. Pat. No. 9,002,460, *Boston Scientific Corporation and Boston Scientific Neuromodulation Corporation* (Petitioners) v. *Nevro Corporation* (Patent Owner), Jul. 25, 2021, 34 pages, for Petition for Inter Partes Review for U.S. Pat. No. 8,892,209—IPR2022-00509, *Boston Scientific Corporation and Boston Scientific Neuromodulation Corporation* (Petitioners) v. *Nevro Corporation* (Patent Owner).
Exhibit 1095: Declaration of Wendy Gu, Ph.D., Jan. 31, 2021 for Petition for Inter Partes Review for U.S. Pat. No. 8,892,209—IPR2022-00509, *Boston Scientific Corporation and Boston Scientific Neuromodulation Corporation* (Petitioners) v. *Nevro Corporation* (Patent Owner).
Advanced Bionics—Precision, Physician Implant Manual, Implantable Pulse Generator model SC1100, https://www.fcc.gov/oet/ea/fccid, 2003, 45 pages.
Aronow et al., "Spinal Cord Stimulation for Treatment of Angina Pectoris," Coronary Artery Disease, 2004, 5 pages.
Barolat et al., "Mapping of sensory responses to epidural stimulation of intraspinal neural structures in man," Jourcal of Neurosurgery, vol. 78, Feb. 1993, 7 pages.
Congress of Neurological Surgeons—Preliminary Program, Annual Meeting Chicago, Illinois Oct. 7-12, 2006, 84 pages.
De Jongste et al., "Efficacy of Spinal Cord Stimulation as Adjuvant Therapy for Intractable Angina Pectoris: A Prospective, Randomized Clinical Study," JACC, vol. 7, Jun. 1994, 6 pages.
Falowski et al., "Spinal Cord Stimulation: An Update," Neurotherapeutics: The Journal of the American Society for Experimental Neuro Therapeautics, vol. 5, Jan. 2008, 14 pages.
FDA—Premarket Approval, PMA P030017-S008, Approval for Artisan 2x8 Paddle Lead, Model SC-8116-XX for the Precision SCS System, https://www.accessdata.fda.gov/scripts/cdrh/cfdocs/cfpma/pma.cfm?id=P030017S008, Aug. 18, 2005, 3 pages.
FDA, Premarket Approval—PMA P840001-S037, Itrel 3 Spinal Cord Stimulation (SCS) for Treatment of Chronic Intractable Pain of hte Trunk and or Limbs, https://www.accessdata.fda.gov/scripts/cdrh/cfdocs/cfpma/pma.cfm?id=P840001S037, Aug. 29, 1995, 3 pages.
Mannheimer et al., "Electrical Stimulation Versus Coronary Artery Bypass Surgery in Severe Angina Pectoris—The ESBY Study," American Heart Association, Inc., 1998, 7 pages.
Manuscript of Eddicks et al., "Thoracic Spinal Cord Stimulation Improves Functional Status and Relieves Symptoms in Patients with Refactory Angina Pectoris: The First Placebo-Controlled Randomized Study," Heart Online First, Jan. 19, 2007, 19 pages.
Medtronic—Itrel 3 Neurostimulator 7425 Neurostimulator, Implant Manual, https://www.neuromodulation.ch/sites/default/files/pictures/itrel3_implant_manual.pdf, 1995, 20 pages.
Medtronic—Itrel EZ Model 7437A Patient Programmer, User Manual, https://fcc.gov/oet/ea/fccid, 2001, 154 pages.
Medtronic—Neuromodulation Product Performance, https://www.medtronic.com/content/dam/medtronic-com/products/product-performance/ppr-reports/product-performance-report-2009.pdf, 2009, 61 pages.
Medtronic—Product Performance Report, https://www.medtronic.com/content/dam/medtronic-com/products/product-performance/ppr-reports/product-performance-report-2010.pdf, 2010, 86 pages.

(56) References Cited

OTHER PUBLICATIONS

Medtronic—Spinal Cord Stimulation, Patient Management Guidelines for Clinicians, https://web.archive/org/web/20060522070227/http://medtronic.com/neuro/paintherapies/pain_treat ment_ladder/library.html, 1999, 19 pages.
Medtronic—Synergy EZ Model 7435 Patient Programmer, User Manual, https://www.fcc.gov/oet/ea/fccid, 1998, 110 pages.
Medtronic—Synergy, Synergy Versitrel 7427 7427V, Dual-Program Neurostimulators for Spinal Cord Stimulation (SCS), http://www.neuromodulation.ch/sites/default/files/pictures/synergy_implant_manual.pdf, 2003, 96 pages.
Medtronic Activa Parkinson's Control Therapy, Summary of Safety and Effectiveness Data for a Supplemental Premarket Approval Application, PMA P960009/S7, https://www.accessdata.fda.gov/cdrh_docs/pdf/p960009S007b.pdf, Aug. 29, 1995, 30 pages.
Merrill et al., "Electrical Stimulation of Excitable Tissue: Design of Efficacious and Safe Protocols," Journal of Neuroscience Methods, 2005, 28 pages.
Summary of Safety and Effectiveness, PMA P030017, Precision Spinal Cord Stimulator (SCS) System, https://www.accessdata.fda.gov/cdrh_docs/pdf3/P030017B.pdf, 2004, 18 pages.
Petition for Inter Partes Review for U.S. Pat. No. 10,576,286—IPR2022-00512, *Boston Scientific Corporation and Boston Scientific Neuromodulation Corporation* (Petitioners) v. *Nevro Corporation* (Patent Owner), Filed Feb. 15, 2022, 95 pages.
Notice of Filing Date Accorded to Petition and Time for Filing Patent Owner Preliminary Response for U.S. Pat. No. 10,576,286—IPR2022-00512, *Boston Scientific Corporation and Boston Scientific Neuromodulation Corporation* (Petitioners) v. *Nevro Corporation* (Patent Owner), Feb. 24, 2022, 5 pages.
Patent Owner's Mandatory Notices for U.S. Pat. No. 10,576,286—IPR2022-00512, *Boston Scientific Corporation and Boston Scientific Neuromodulation Corporation* (Petitioners) v. *Nevro Corporation* (Patent Owner), Filed Mar. 2, 2022, 5 pages.
Petition for Inter Partes Review for U.S. Pat. No. 10,556,112—IPR2022-00511, *Boston Scientific Corporation and Boston Scientific Neuromodulation Corporation* (Petitioners) v. *Nevro Corporation* (Patent Owner), Filed Feb. 15, 2022, 95 pages.
Notice of Filing Date Accorded to Petition and Time for Filing Patent Owner Preliminary Response for U.S. Patent No. 10,556,112—IPR2022-00511, *Boston Scientific Corporation and Boston Scientific Neuromodulation Corporation* (Petitioners) v. *Nevro Corporation* (Patent Owner), Feb. 24, 2022, 5 pages.
Patent Owner's Mandatory Notices for U.S. Pat. No. 10,556,112—IPR2022-00511, *Boston Scientific Corporation and Boston Scientific Neuromodulation Corporation* (Petitioners) v. *Nevro Corporation* (Patent Owner), Filed Mar. 2, 2022, 5 pages.
Exhibit 1003: Declaration of Marom Bikson, Ph.D., Feb. 15, 2022, 128 pages, for Petition for Inter Partes Review for U.S. Pat. No. 10,576,286—IPR2022-00512 and Petition for Inter Partes Review for U.S. Pat. No. 10,556,112—IPR2022-00511, *Boston Scientific Corporation and Boston Scientific Neuromodulation Corporation* (Petitioners) v. *Nevro Corporation* (Patent Owner).
Exhibit 1004: Curriculum Vitae of Marom Bikson, Ph.D., 72 pages, for Petition for Inter Partes Review for U.S. Pat. No. 10,576,286—IPR2022-00512 and Petition for Inter Partes Review for U.S. Pat. No. 10,556,112—IPR2022-00511, *Boston Scientific Corporation and Boston Scientific Neuromodulation Corporation* (Petitioners) v. *Nevro Corporation* (Patent Owner).
Exhibit 1014: Declaration of Natalie Bryan, Feb. 7, 2022, 15 pages for Petition for Inter Partes Review for U.S. Pat. No. 10,576,286—IPR2022-00512 and Petition for Inter Partes Review for U.S. Pat. No. 10,556,112—IPR2022-00511, *Boston Scientific Corporation and Boston Scientific Neuromodulation Corporation* (Petitioners) v. *Nevro Corporation* (Patent Owner).
Exhibit 1015: Declaration of Dr. Erik Shaw, Feb. 14, 2022, for Petition for Inter Partes Review for U.S. Pat. No. 10,576,286—IPR2022-00512 and Petition for Inter Partes Review for U.S. Patent No. 10,556, 112—IPR2022-00511, *Boston Scientific Corporation and Boston Scientific Neuromodulation Corporation* (Petitioners) v. *Nevro Corporation* (Patent Owner).
Exhibit 1019: Declaration of Michael Henry Verdolin, Feb. 15, 2022, for Petition for Inter Partes Review for U.S. Pat. No. 10,576,286—IPR2022-00512 and Petition for Inter Partes Review for U.S. Pat. No. 10,556,112—IPR2022-00511, *Boston Scientific Corporation and Boston Scientific Neuromodulation Corporation* (Petitioners) v. *Nevro Corporation* (Patent Owner).
Exhibit 1022: Declaration of Thomas L. Yearwood, M.D., Ph.D., 13 pages, for Petition for Inter Partes Review for U.S. Pat. No. 10,576,286—IPR2022-00512 and Petition for Inter Partes Review for U.S. Pat. No. 10,556,112—IPR2022-00511, *Boston Scientific Corporation and Boston Scientific Neuromodulation Corporation* (Petitioners) v. *Nevro Corporation* (Patent Owner).
Exhibit 1034: Curriculum Vitae of Dr. Erik Shaw, 4 pages, for Petition for Inter Partes Review for U.S. Pat. No. 10,576,286—IPR2022-00512 and Petition for Inter Partes Review for U.S. Pat. No. 10,556,112—IPR2022-00511, *Boston Scientific Corporation and Boston Scientific Neuromodulation Corporation* (Petitioners) v. *Nevro Corporation* (Patent Owner).
Exhibit 1035: Declaration of Dr. Richard Boydston North, Feb. 12, 2022, 10 pages, for Petition for Inter Partes Review for U.S. Pat. No. 10,576,286—IPR2022-00512 and Petition for Inter Partes Review for U.S. Pat. No. 10,556,112—IPR2022-00511, *Boston Scientific Corporation and Boston Scientific Neuromodulation Corporation* (Petitioners) v. *Nevro Corporation* (Patent Owner).
Exhibit 1036: Curriculum Vitae of Dr. Richard Boydston North, 53 pages, for Petition for Inter Partes Review for U.S. Pat. No. 10,576,286—IPR2022-00512 and Petition for Inter Partes Review for U.S. Pat. No. 10,556,112—IPR2022-00511, *Boston Scientific Corporation and Boston Scientific Neuromodulation Corporation* (Petitioners) v. *Nevro Corporation* (Patent Owner).
Exhibit 1051: Response to Certificate of Corrections for U.S. Pat. No. 9,002,549, Jan. 25, 2022, 2 pages, for Petition for Inter Partes Review for U.S. Pat. No. 10,576,286—IPR2022-00512 and Petition for Inter Partes Review for U.S. Pat. No. 10,556,112—IPR2022-00511, *Boston Scientific Corporation and Boston Scientific Neuromodulation Corporation* (Petitioners) v. *Nevro Corporation* (Patent Owner).
Exhibit 1052: Applicant's Reply to Response to the Request for Certificate of Corrections for U.S. Pat. No. 9,002,459, Jul. 28, 2021, 2 pages, for Petition for Inter Partes Review for U.S. Pat. No. 10,576,286—IPR2022-00512 and Petition for Inter Partes Review for U.S. Pat. No. 10,556,112—IPR2022-00511, *Boston Scientific Corporation and Boston Scientific Neuromodulation Corporation* (Petitioners) v. *Nevro Corporation* (Patent Owner).
FDA—Premarket Approval, PMA P030017-S002, Boston Scientific Corp., Precision Spinal Cord Stimulation (SCS), Stimulator, Spinal Cord, Totally Implanted for Pain Relief, Model No. SC-1110, https://www.accessdata.fda.gov/scripts/cdrh/cfdocs/cfpma/pma.cfm?id=P030017, Oct. 1, 2004, 3 pages.
New Release, "Boston Scientific Announces Launch of New Precision Plus Spinal Cord Stimulation System—Hardware and software innovations offer new benefits to physicans and patients," PRNewswire-First Call, https://news.bostonscientific.com/news-releases?item=58980, 2 pages.
Shaw et al., "1200Hz Sub-Threshold Epidural Stimulation for Pain Control," Shepherd Center, Interventional Pain Management Physician, Shephard Center, Atlanta, GA., 1 page.
Patent Owner's Preliminary Response for U.S. Pat. No. 8,892,209 for Inter Partes Review IPR2022-00509, *Boston Scientific Corporation and Boston Scientific Neuromodulation Corporation* (Petitioners) v. *Nevro Corporation* (Patent Owner), Filed May 16, 2022, 86 pages.
Patent Owner's Exhibit List for U.S. Pat. No. 8,892,209 for Inter Partes Review IPR2022-00509, *Boston Scientific Corporation and Boston Scientific Neuromodulation Corporation* (Petitioners) v. *Nevro Corporation* (Patent Owner), Filed May 16, 2022, 10 pages.
Patent Owner's Response to Petitioner's Statement on Parallel Petitions for U.S. Pat. No. 8,892,209 for Inter Partes Review IPR2022-00509, *Boston Scientific Corporation and Boston Scientific Neuromodulation Corporation* (Petitioners) v. *Nevro Corporation* (Patent Owner), Filed May 16, 2022, 8 pages.

(56) References Cited

OTHER PUBLICATIONS

Petitioner's Reply to Patent Owner's Preliminary Response for U.S. Pat. No. 8,892,209 for Inter Partes Review IPR2022-00509, *Boston Scientific Corporation and Boston Scientific Neuromodulation Corporation* (Petitioners) v. *Nevro Corporation* (Patent Owner), Filed Jun. 24, 2022, 12 pages.
Petitioner's Updated Exhibit List for U.S. Pat. No. 8,892,209 for Inter Partes Review IPR2022-00509, *Boston Scientific Corporation and Boston Scientific Neuromodulation Corporation* (Petitioners) v. *Nevro Corporation* (Patent Owner), Filed Jun. 24, 2022, 11 pages.
Patent Owner's Sur-Reply for U.S. Pat. No. 8,892,209 for Inter Partes Review IPR2022-00509, *Boston Scientific Corporation and Boston Scientific Neuromodulation Corporation* (Petitioners) v. *Nevro Corporation* (Patent Owner), Filed Jul. 5, 2022, 13 pages.
Joint Motion to Terminate Pursuant to 35 U.S.C. § 317 for U.S. Pat. No. 8,892,209 for Inter Partes Review IPR2022-00509, *Boston Scientific Corporation and Boston Scientific Neuromodulation Corporation* (Petitioners) v. *Nevro Corporation* (Patent Owner), Filed Aug. 5, 2022, 6 pages.
Joint Request that the Settlement Agreement be Treated as Business Confidential Information pursuant to 35 U.S.C. § 317 for U.S. Pat. No. 8,892,209 for Inter Partes Review IPR2022- 00509, *Boston Scientific Corporation and Boston Scientific Neuromodulation Corporation* (Petitioners) v. *Nevro Corporation* (Patent Owner), Filed Aug. 5, 2022, 4 pages.
Patent Owner's Preliminary Response for U.S. Pat. No. 8,892,209—IPR2022-00510, *Boston Scientific Corporation and Boston Scientific Neuromodulation Corporation* (Petitioners) v. *Nevro Corporation* (Patent Owner), Filed May 16, 2022, 80 pages.
Patent Owner's Exhibit List for U.S. Pat. No. 8,892,209—IPR2022-00510, *Boston Scientific Corporation and Boston Scientific Neuromodulation Corporation* (Petitioners) v. *Nevro Corporation* (Patent Owner), Filed May 16, 2023, 10 pages.
Petitioners' Reply to Patent Owner's Preliminary Response for U.S. Pat. No. 8,892,209—IPR2022-00510, *Boston Scientific Corporation and Boston Scientific Neuromodulation Corporation* (Petitioners) v. *Nevro Corporation* (Patent Owner), Filed Jun. 24, 2022, 12 pages.
Petitioners' Updated Exhibit List for U.S. Pat. No. 8,892,209—IPR2022-00510, *Boston Scientific Corporation and Boston Scientific Neuromodulation Corporation* (Petitioners) v. *Nevro Corporation* (Patent Owner), Filed Jun. 24, 2022, 11 pages.
Patent Owners' Sur-Reply for U.S. Pat. No. 8,892,209—IPR2022-00510, *Boston Scientific Corporation and Boston Scientific Neuromodulation Corporation* (Petitioners) v. *Nevro Corporation* (Patent Owner), Filed Jul. 5, 2022, 13 pages.
Joint Request that the Settlement Agreement Be Treated as Business Confidential Information Pursuant to 35 U.S.C.§ 317 for U.S. Pat. No. 8,892,209—IPR2022-00510, *Boston Scientific Corporation and Boston Scientific Neuromodulation Corporation* (Petitioners) v. *Nevro Corporation* (Patent Owner), Filed Aug. 5, 2022, 4 pages.
Decision—Settlement Prior to Institution of Trial 37 C.F.R. § 42.74 for U.S. Pat. No. 8,892,209—IPR2022-00510; U.S. Pat. No. 8,892,209 for Inter Partes Review IPR2022-00509; U.S. Pat. No. 10,576,286—Inter Partes Review for IPR2022-00512; U.S. Pat. No. 10,556,112—Inter Partes Review for IPR2022-00511—*Boston Scientific Corporation and Boston Scientific Neuromodulation Corporation* (Petitioners) v. *Nevro Corporation* (Patent Owner), Filed Aug. 8, 2022, 4 page.
Exhibit 2002: C.V. of Peter Crosby for U.S. Pat. No. 8,892,209—IPR2022-00510 and Petition for Inter Partes Review for U.S. Pat. No. 8,892,209—IPR2022-00509, *Boston Scientific Corporation and Boston Scientific Neuromodulation Corporation* (Petitioners) v. *Nevro Corporation* (Patent Owner).
Exhibit 2003: Declaration of Peter Crosby for U.S. Pat. No. 8,892,209—IPR2022-00510 and Petition for Inter Partes Review for U.S. Pat. No. 8,892,209—IPR2022-00509, *Boston Scientific Corporation and Boston Scientific Neuromodulation Corporation* (Petitioners) v. *Nevro Corporation* (Patent Owner).
Exhibit 2007: C.V. of Michael Fishman, M.D. for U.S. Pat. No. 8,892,209—IPR2022-00510 and Petition for Inter Partes Review for U.S. Pat. No. 8,892,209—IPR2022-00509, *Boston Scientific Corporation and Boston Scientific Neuromodulation Corporation* (Petitioners) v. *Nevro Corporation* (Patent Owner).
Exhibit 2008: Declaration of Michael Fishman, M.D. for U.S. Pat. No. 8,892,209—IPR2022-00510 and Petition for Inter Partes Review for U.S. Pat. No. 8,892,209—IPR2022-00509, *Boston Scientific Corporation and Boston Scientific Neuromodulation Corporation* (Petitioners) v. *Nevro Corporation* (Patent Owner).
Exhibit 2015: *Nevro Corp.* v. *Boston Scientific Corp.*, 955 F.3d 35 (Fed. Cir. 2020) for U.S. Pat. No. 8,892,209—IPR2022-00510; U.S. Pat. No. 8,892,209 for Inter Partes Review IPR2022-00509; U.S. Pat. No. 10,576,286—Inter Partes Review for IPR2022-00512; U.S. Pat. No. 10,556,112—Inter Partes Review for IPR2022-00511—*Boston Scientific Corporation and Boston Scientific Neuromodulation Corporation* (Petitioners) v. *Nevro Corporation* (Patent Owner).
Exhibit 2016: *Nevro Corp.* v. *Boston Scientific Corp.*, No. 16-cv-06830-VC, 2018 WL 4676501 (N.D. Cal. Jul. 24, 2018) for U.S. Pat. No. 8,892,209—IPR2022-00510 and Petition for Inter Partes Review for U.S. Pat. No. 8,892,209—IPR2022-00509, *Boston Scientific Corporation and Boston Scientific Neuromodulation Corporation* (Petitioners) v. *Nevro Corporation* (Patent Owner).
Exhibit 2022: *Nevro Corp.* v. *Boston Scientific Corp.*, No. 3:16-cv-6830, Dkt. 1, Complaint for Patent Infringement and Declaratory Judgment, Demand for Jury Trial (N.D. Cal. Nov. 28, 2016) for U.S. Pat. No. 8,892,209—IPR2022-00510; U.S. Pat. No. 8,892,209 for Inter Partes Review IPR2022-00509; U.S. Pat. No. 10,576,286—Inter Partes Review for IPR2022-00512; U.S. Patent No. 10,556,112—Inter Partes Review for IPR2022-00511—*Boston Scientific Corporation and Boston Scientific Neuromodulation Corporation* (Petitioners) v. *Nevro Corporation* (Patent Owner).
Exhibit 2023: *Nevro Corp.* v. *Boston Scientific Corp.*, No. 3:16-cv-06830-VC, Dkt. 554, Stipulation and [Proposed] Order of Dismissal (N.D. Cal. Dec. 14, 2020) for U.S. Pat. No. 8,892,209—IPR2022-00510; U.S. Pat. No. 8,892,209 for Inter Partes Review IPR2022-00509; U.S. Pat. No. 10,576,286—Inter Partes Review for IPR2022-00512; U.S. Pat. No. 10,556,112—Inter Partes Review for IPR2022-00511—*Boston Scientific Corporation and Boston Scientific Neuromodulation Corporation* (Petitioners) v. *Nevro Corporation* (Patent Owner).
Exhibit 2025: *Nevro Corp.* v. *Boston Scientific Corp.*, No. 1:21-cv-00258-UNA, Dkt. 1, Complaint (D.Del. Feb. 23, 2021) for U.S. Pat. No. 8,892,209—IPR2022-00510; U.S. Pat. No. 8,892,209 for Inter Partes Review IPR2022-00509; U.S. Pat. No. 10,576,286—Inter Partes Review for IPR2022-00512; U.S. Pat. No. 10,556,112—Inter Partes Review for IPR2022-00511—*Boston Scientific Corporation and Boston Scientific Neuromodulation Corporation* (Petitioners) v. *Nevro Corporation* (Patent Owner).
Exhibit 2026: *Nevro Corp.* v. *Stimwave Technologies, Inc.*, No. 1:19-cv-00325-UNA, Dkt. 1, Complaint for Patent Infringement, Declaratory Judgment of Patent Infringement, Violation of the Lanham Act, and Deceptive Trade Practices (D. Del Feb. 14, 2019) for U.S. Pat. No. 8,892,209—IPR2022-00510 and Petition for Inter Partes Review for U.S. Pat. No. 8,892,209—IPR2022-00509, *Boston Scientific Corporation and Boston Scientific Neuromodulation Corporation* (Petitioners) v. *Nevro Corporation* (Patent Owner).
Exhibit 2027: *Nevro Corp.* v. *Stimwave Technologies, Inc.*, No. 1:19-cv-00325-CFC, Dkt. 98, Stimwave's Answering Brief in Opposition to Plaintiff Nevro's Motion for a Preliminary Injunction (D.Del. Jun. 6, 2019) for U.S. Pat. No. 8,892,209—IPR2022-00510 and Petition for Inter Partes Review for U.S. Pat. No. 8,892,209—IPR2022-00509, *Boston Scientific Corporation and Boston Scientific Neuromodulation Corporation* (Petitioners) v. *Nevro Corporation* (Patent Owner).
Exhibit 2028: *Nevro Corp.* v. *Stimwave Technologies, Inc.*, No. 1:19-cv-00325-CFC, Dkt. 231, Stipulated Consent Judgment and Permanent Injunction (D.Del. Mar. 2, 2020) for U.S. Pat. No. 8,892,209—IPR2022-00510 and Petition for Inter Partes Review for U.S. Pat. No. 8,892,209—IPR2022-00509, *Boston Scientific Corporation and Boston Scientific Neuromodulation Corporation* (Petitioners) v. *Nevro Corporation* (Patent Owner).
Exhibit 2032: Ex parte Knudson, Appeal No. 2021-001841, Decision on Appeal (PTAB Oct. 26, 2021) for U.S. Pat. No. 8,892,209—IPR2022-00510 and Petition for Inter Partes Review for U.S. Pat.

(56) References Cited

OTHER PUBLICATIONS

No. 8,892,209—IPR2022-00509, *Boston Scientific Corporation and Boston Scientific Neuromodulation Corporation* (Petitioners) v. *Nevro Corporation* (Patent Owner).
Exhibit 2033: *Nevro Corp.* v. *Nalu Medical, Inc.*, No. 20-291 (CFC)(JLH), Nevro Corp.'s Response to Defendant Nalu Medical, Inc.'s First Set of Interrogatories (Nos. 1-10) (D. Del. May 7, 2021) for U.S. Pat. No. 8,892,209—IPR2022-00510 and Petition for Inter Partes Review for U.S. Pat. No. 8,892,209—IPR2022-00509, *Boston Scientific Corporation and Boston Scientific Neuromodulation Corporation* (Petitioners) v. *Nevro Corporation* (Patent Owner).
Exhibit 2035: *Boston Scientific Neuromodulation Corporation* v. *Nevro Corporation*, IPR2015-01203, Paper 10, Decision Denying Institution of Inter Partes Review (PTAB Nov. 30, 2015) for U.S. Pat. No. 8,892,209—IPR2022-00510; U.S. Pat. No. 8,892,209 for Inter Partes Review IPR2022-00509; U.S. Pat. No. 10,576,286; Inter Partes Review for IPR2022-00512; U.S. Pat. No. 10,556,112—Inter Partes Review for IPR2022-00511—*Boston Scientific Corporation and Boston Scientific Neuromodulation Corporation* (Petitioners) v. *Nevro Corporation* (Patent Owner).
Exhibit 2038: *Nevro Corp.* v. *Nalu Medical, Inc.*, No. 1:20-cv-00291-CFC, Dkt. 14, First Amended Complaint for Patent Infringement (D. Del Jun. 1, 2020) for U.S. Pat. No. 8,892,209—IPR2022-00510 and Petition for Inter Partes Review for U.S. Pat. No. 8,892,209—IPR2022-00509, *Boston Scientific Corporation and Boston Scientific Neuromodulation Corporation* (Petitioners) v. *Nevro Corporation* (Patent Owner).
Exhibit 2045: *Nevro Corp.* v. *Stimwave Technologies, Inc.*, No. 19-325-CFC, 2019 WL 3322368 (D.Del. Jul. 24, 2019) for U.S. Pat. No. 8,892,209—IPR2022-00510 and Petition for Inter Partes Review for U.S. Pat. No. 8,892,209—IPR2022-00509, *Boston Scientific Corporation and Boston Scientific Neuromodulation Corporation* (Petitioners) v. *Nevro Corporation* (Patent Owner).
Exhibit 2046: *Nevro Corp.* v. *Nalu Medical, Inc.*, No. 1:20-cv-00291-UNA, Dkt. 1, Complaint for Patent Infringement (D.Del. Feb. 28, 2020) for U.S. Pat. No. 8,892,209—IPR2022-00510 and Petition for Inter Partes Review for U.S. Pat. No. 8,892,209—IPR2022-00509, *Boston Scientific Corporation and Boston Scientific Neuromodulation Corporation* (Petitioners) v. *Nevro Corporation* (Patent Owner).
Exhibit 2052: U.S. Patent and Trademark Office, Declaration of James Thacker, U.S. Appl No. 13/705,021 (Dec. 4, 2012) (No. 3:16-cv-06830-VC, Dkt. 398-13, Exhibit 12 (May 24, 2018) for U.S. Pat. No. 8,892,209—IPR2022-00510 and Petition for Inter Partes Review for U.S. Pat. No. 8,892,209—IPR2022-00509, *Boston Scientific Corporation and Boston Scientific Neuromodulation Corporation* (Petitioners) v. *Nevro Corporation* (Patent Owner).
Exhibit 2055: *Nevro Corp.* v. *Boston Scientific Corp.*, No. 18-2220, Dkt. 32, Principal and Response Brief for Defendants-Cross-Appellants Boston Scientific Corporation and Boston Scientific Neuromodulation Corporation (Fed. Cir. Jan. 17, 2019) for U.S. Pat. No. 8,892,209—IPR2022-00510 and Petition for Inter Partes Review for U.S. Pat. No. 8,892,209—IPR2022-00509, *Boston Scientific Corporation and Boston Scientific Neuromodulation Corporation* (Petitioners) v. *Nevro Corporation* (Patent Owner).
Exhibit 2060: Inter Partes Review 2021-01203 for U.S. Pat. No. 8,359,102—Patent Owner's Preliminary Response, *Boston Scientific Neuromodulation Corporation.* v. *Nevro Corp.*, Sep. 1, 2015, 70 pages, for Petition for Inter Partes Review for U.S. Pat. No. 8,892,209—IPR2022-00510, *Boston Scientific Corporation and Boston Scientific Neuromodulation Corporation* (Petitioners) v. *Nevro Corporation* (Patent Owner).
Patent Owner's Preliminary Response for U.S. Pat. No. 10,576,286—Inter Partes Review for IPR2022-00512, *Boston Scientific Corporation and Boston Scientific Neuromodulation Corporation* (Petitioners) v. *Nevro Corporation* (Patent Owner), Filed May 24, 2022, 38 pages.
Joint Motion to Terminate Pursuant to 35 U.S.C. 317 for U.S. Pat. No. 10,576,286—Inter Partes Review for IPR2022-00512, *Boston Scientific Corporation and Boston Scientific Neuromodulation Corporation* (Petitioners) v. *Nevro Corporation* (Patent Owner), Filed Aug. 5, 2022, 6 pages.
Joint Request that the Settlement Agreement be Treated as Business Confidential Information Pursuant to 35 U.S.C. 317 for U.S. Pat. No. 10,576,286—Inter Partes Review for IPR2022-00512, *Boston Scientific Corporation and Boston Scientific Neuromodulation Corporation* (Petitioners) v. *Nevro Corporation* (Patent Owner), Filed Aug. 5, 2022, 4 pages.
Patent Owner's Preliminary Response for U.S. Pat. No. 10,556,112—Inter Partes Review IPR2022-00511, *Boston Scientific Corporation and Boston Scientific Neuromodulation Corporation* (Petitioners) v. *Nevro Corporation* (Patent Owner), Filed May 24, 2022, 37 pages.
Joint Motion to Terminate Pursuant to 35 U.S.C. § 317 for U.S. Pat. No. 10,556,112—Inter Partes Review IPR2022-00511, *Boston Scientific Corporation and Boston Scientific Neuromodulation Corporation* (Petitioners) v. *Nevro Corporation* (Patent Owner), Filed May 24, 2022, 37 pages.
Joint Request that the Settlement Agreement be Treated as Business Confidential Information Pursuant to 35 U.S.C. § 317 for U.S. Pat. No. 10,556,112—Inter Partes Review IPR2022-00511, *Boston Scientific Corporation and Boston Scientific Neuromodulation Corporation* (Petitioners) v. *Nevro Corporation* (Patent Owner), Filed May 24, 2022, 37 pages.
Exhibit 2002: *Boston Scientific Corp.* v. *Nevro Corp.*, No. 18-644 (CFC), Dkt. 27, Answer, Affirmative Defenses, and Counterclaims to First Amended Complaint (D. Del. Dec. 9, 2019) Inter Partes Review for IPR2022-00512; U.S. Pat. No. 10,556,112—Inter Partes Review for IPR2022-00511—*Boston Scientific Corporation and Boston Scientific Neuromodulation Corporation* (Petitioners) v. *Nevro Corporation* (Patent Owner).
Exhibit 2003: *Boston Scientific Corp.* v. *Nevro Corp.*, No. 16-1163 (CFC)(Consolidated), Dkt. 551, Claim Construction Order (D. Del. Feb. 25, 2021) Inter Partes Review for IPR2022-00512; U.S. Pat. No. 10,556,112—Inter Partes Review for IPR2022-00511—*Boston Scientific Corporation and Boston Scientific Neuromodulation Corporation* (Petitioners) v. *Nevro Corporation* (Patent Owner).
Exhibit 2036: *Boston Scientific Neuromodulation Corporation* v. *Nevro Corp.*, IPR2015-01204, Paper 10, Decision Denying Institution of Inter Partes Review (PTAB Nov. 30, 2015) Inter Partes Review for IPR2022-00512; U.S. Pat.No. 10,556,112—Inter Partes Review for IPR2022-00511—*Boston Scientific Corporation and Boston Scientific Neuromodulation Corporation* (Petitioners) v. *Nevro Corporation* (Patent Owner).
Lee et al., "Predicted Effects of Pulse Width Programming in Spinal Cord Stimulation: A Mathematical Modeling Study," Medical & Biological Engineering & Computing, 2011, 10 pages.
FDA Summary of Safety and Effectiveness Data, PMA P130022, Senza Spinal Cord Stimulation (SCS) System, 56 pages.
Nevro Senza Spinal Cord Stimulator (SCS) System—Patient Manual, 2021, 94 pages.
Boston Scientific, "Precision™ Spinal Cord Stimulator System Clinician Manual," 9108273-04, 2017, 74 pages.
St. Jude Medical, "Eon Mini™ Rechargeable IPG" 2015, 5 pages.
Nevro, News Release: "Neurosurgery Selects the SENZA-RCT 24-Month Outcomes Publication as the Top Pain Paper of the Year" Jun. 15, 2017, 2 pages.
Morgan Stanely Research, "Nevro Corp, Fundamentals are Very Much Intact," Nov. 8, 2016, 12 pages.
Morgan Stanley—Research, "Medical Technology: Disrupting Neuromodulation Abbott & Nevro are the Winners," Feb. 22, 2017, 27 pages.
Mills et al., Nevro, "Initation of Coverage: Compelling growth engine with plenty of fuel in the tank; initiate at Buy, $120 target," Canaccord Genuity, Mar. 23, 2017, 57 pages.
"WaveWriter Alpha Spinal Cord Stimulator System wins Best Overall Medical Device Solution Award," 222 Shares, May 24, 2021, 2 pages.
Boston Scientific, "Boston Scientific Launches WaveWriter Alpha™ Spinal Cord Stimulator Systems in U.S.," Jan. 14, 2021, 3 pages.
Foletti et al., "Neurostimulation technology for the treatment of chronic pain: a focus on spinal cord stimulation," Future Drugs Ltd, 2007, 14 pages.

(56) References Cited

OTHER PUBLICATIONS

"EQ-5D-3L, About," available at https://euroqol.org/eq-5dinstruments/eq-5d-3l-about/ Mar. 31, 2022, 3 pages.
Kloth, Luther C., "Electrical Stimulation Technologies for Wound Healing," Wound Healthing Society, 2014, 11 pages.
Kathuroju et al., "Effect of Low Frequency Pulsed DC on Human Skin in Vivo: Resistance Studies in Reverse Iontophoresis," 104 Sensors & Transducers Journal 47-57, 2009, 17 pages.
Bendel, Markus, "New Developments in Spinal Stimulation for Pain Management," Mayo Clinic, https://connect.mayoclinic.org/blog/adult-pain-medicine/newsfeed-post/new-developments-in-spinal-stimulation/, Nov. 2018, 13 pages.
J.P. Morgan, "Nevro—Quarterly Results In-line with Preannouncement; Hiring in Focus for 2H18," North America Equity Research, Aug. 2, 2018, 8 pages.
Mironer et al., "Pain Tolernace Threshold: A Pilot Study of an Objective Measurement of Spinal Cord Stimulator Trial Results," Pain Medicine, vol. 1, No. 2, 2000, 6 pages.
Smits et al., "Spinal cord stimulation induces c-Fos expression in the dorsal horn in rats with neuropathic pain after partial sciatic nerve injury," Neuroscience Letters 450, 2009, 4 pages.
Struijk et al., "Paresthesia Thresholds in Spinal Cord Stimulation: A Comparison of Theoretical Results with Clinical Data," IEEE Transactions on Rehabilitation Engineering, vol. 1, No. 2, Jun. 1993, 8 pages.
Wolter et al., "Effects of Sub-perception threshold spinal cord stimulation in neuropathic pain: A randomized controlled double-blind crossover study," European Journal of Pain, 2012, 8 pages.
Abejon et al., "Effects of Movement and Postural Positions in Spinal Cord Stimulation in the New Rechargeable Systems," Pain Physician, 2014, 8 pages.
Holsheimer et al., "Spinal Geometry and Paresthesia Coverage in Spinal Cord Stimulation," International Neuromodulation Society, 1998, 8 pages.
Kumar et al., "The use of spinal cord stimulation in pain management," Pain Management, 2012, 11 pages.
Kumar, Krishna, "Neuromodulation and Immortality," Neuromodulation, 2014, 3 pages.
Taylor et al., "Spinal cord stimulation in the treatment of refractory angina: systematic review and meta-analysis of randomised controlled trials," BioMed Central—BMC Cardiovascular Disorders, 2009, 13 pages.
Diedrichs et al., "Symptomatic Relief Precedes Improvement of Myocardial Blood Flow in Patients Under Spinal Cord Stimulation," Current Controlled Trials in Cardiovascular Medicine, 2005, 7 pages.
Wu et al., "Putative Mechanisms Behind Effects of Spinal Cord Stimulation on Vascular Diseases: A Review of Experimental Studies," Autonomic Neuroscience, 2008, 15 pages.
Webster's New World Medical Dictionary, pp. 317-318, Wiley Publishing, Inc., 3d edition, 2008, 5 pages.
Milligan et al., "Pathological and Protective Roles of Glia in Chronic Pain," Nat Rev Neurosci. 2009, pages.
Vallejo et al., "The Role of Glia and the Immune System in the Development and Maintenance of Neuropathic Pain," Pain Pract. 2010, pages.
De Leo et al., "The Tetrapartite Synapse: Path to CNS centralization and Chronic Pain," Pain. 2006, pages.
Dong et al., "Research on Stimulus Pattern for Inhibition of Detrusor Hyperreflexia," 3rd International Conference on Biomedical Engineering and Informatics, 2010, 4 pages.

\* cited by examiner

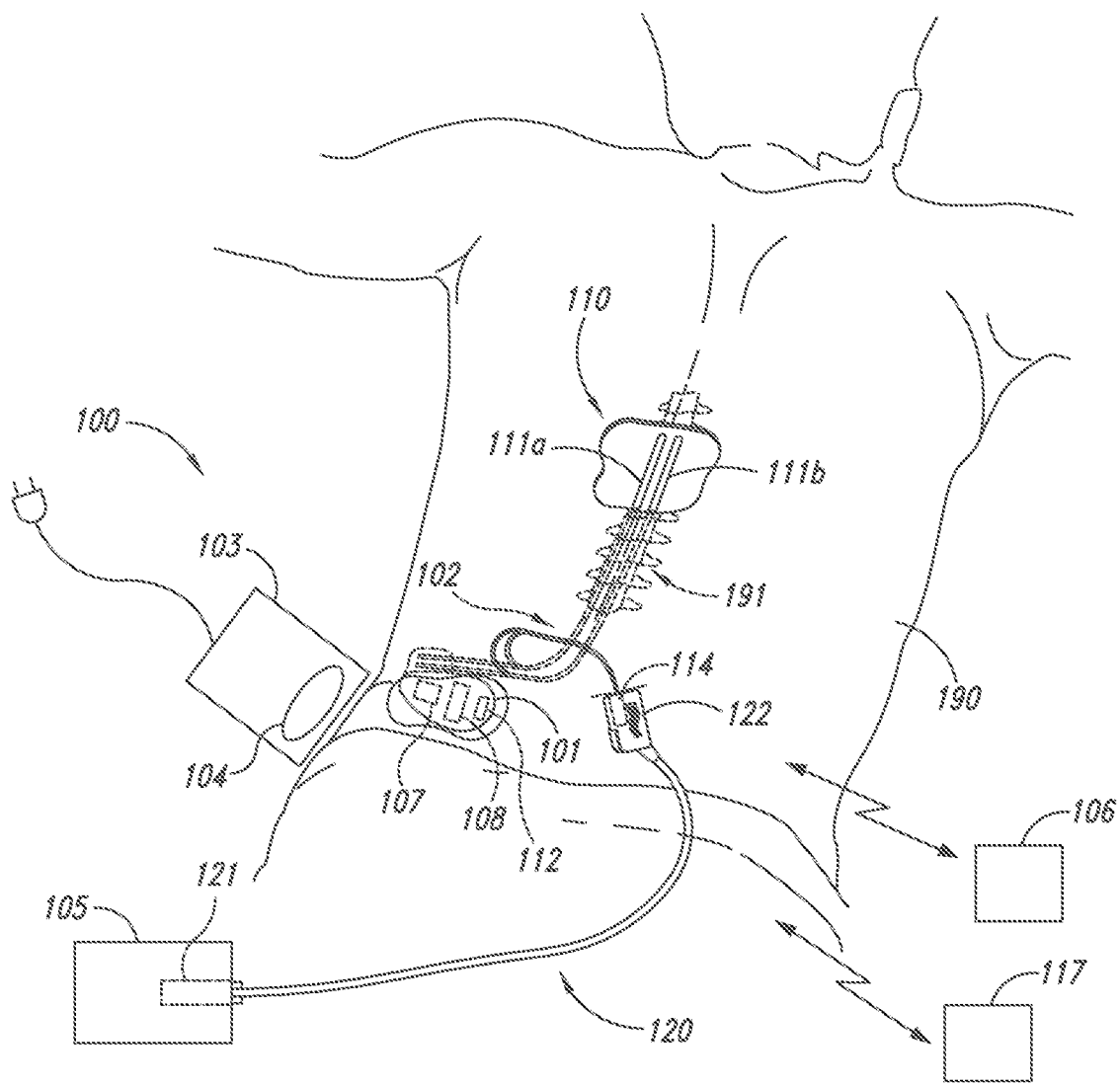

METHODS AND SYSTEMS FOR DISEASE TREATMENT USING ELECTRICAL STIMULATION

CROSS-REFERENCE TO RELATED APPLICATION

The present application is a continuation of U.S. patent application Ser. No. 16/322,304, filed on Jul. 7, 2020, which is a continuation of U.S. patent application Ser. No. 15/870,052, filed on Jan. 12, 2018, now issued as U.S. Pat. No. 10,751,536, which is a continuation of U.S. patent application Ser. No. 14/300,193, filed Jun. 9, 2014, now issued as U.S. Pat. No. 9,895,639, which claims priority to U.S. Provisional Application 61/833,392, filed on Jun. 10, 2013, which are incorporated herein by reference.

TECHNICAL FIELD

The present disclosure is directed generally to methods and systems for disease treatment using electrical stimulation. Particular embodiments include changing an activity, expression, or both activity and expression of a fast sodium channel, a glial cell, or both a fast sodium channel and a glial cell of the patient by applying electrical stimulation to a target neural population of a patient.

BACKGROUND

Neurological stimulators have been developed to treat pain, movement disorders, functional disorders, spasticity, cancer, cardiac disorders, and various other medical conditions. Implantable neurological stimulation systems generally have an implantable signal generator and one or more leads that deliver electrical pulses to neurological tissue or muscle tissue. For example, several neurological stimulation systems for spinal cord stimulation (SCS) have cylindrical leads that include a lead body with a circular cross-sectional shape and one or more conductive rings (i.e., contacts) spaced apart from each other at the distal end of the lead body. The conductive rings operate as individual electrodes and, in many cases, the SCS leads are implanted percutaneously through a needle inserted into the epidural space, with or without the assistance of a stylet.

Once implanted, the signal generator applies electrical pulses to the electrodes, which in turn modify the function of the patient's nervous system, such as by altering the patient's responsiveness to sensory stimuli and/or altering the patient's motor-circuit output. In SCS therapy for the treatment of pain, the signal generator applies electrical pulses to the spinal cord via the electrodes. In conventional SCS therapy, electrical pulses are used to generate sensations (known as paresthesia) that mask or otherwise alter the patient's sensation of pain. For example, in many cases, patients report paresthesia as a tingling sensation that is perceived as less uncomfortable than the underlying pain sensation.

Aspects of the present disclosure are directed to systems and methods that make use of, employ, rely on and/or otherwise use or incorporate aspects the interaction between electrical therapy and the patients to whom the therapy is applied.

BRIEF DESCRIPTION OF THE DRAWINGS

FIG. 1 is a partially schematic illustration of an implantable spinal cord modulation system positioned at the spine to deliver therapeutic signals in accordance with several embodiments of the present technology.

DETAILED DESCRIPTION

Neurological stimulators have been developed to treat pain, movement disorders, functional disorders, spasticity, cancer, cardiac disorders, and various other medical conditions. Implantable neurological stimulation systems generally have an implantable pulse generator and one or more leads that deliver electrical pulses to neurological tissue or muscle tissue. For example, several neurological stimulation systems for spinal cord stimulation (SCS) have cylindrical leads that include a lead body with a circular cross-sectional shape and one or more conductive rings spaced apart from each other at the distal end of the lead body. The conductive rings operate as individual electrodes and, in many cases, the SCS leads are implanted percutaneously through a large needle inserted into the epidural space, with or without the assistance of a stylet.

Once implanted, the pulse generator applies electrical pulses to the electrodes, which in turn modify the function of the patient's nervous system, such as by altering the patient's responsiveness to sensory stimuli, altering the patient's motor-circuit output, and/or otherwise modifying other neural function. Example neuromodulation systems, methods, and therapy parameters are described in co-owned published patent applications: US Patent Publication No. 2009/0204173; US Patent Publication No. 2007/0213771; US Patent Publication No. 2010/0191307; US Patent Publication No. 2010/0274312; US Patent Publication No. 2010/0274314; US Patent Publication No. 2012/0172946; and US Patent Publication No. 2013/0066411, which are all incorporated herein by reference in their entireties. To the extent the foregoing materials and/or any other materials incorporated herein by reference conflict with the present disclosure, the present disclosure controls.

Provided herein are various embodiments of neuromodulation systems, methods, and therapies for the treatment of medical conditions. The specific embodiments discussed are not to be construed as limitations on the scope of the disclosed technology. It will be apparent to one skilled in the art that various equivalents, changes, and modifications may be made without departing from the scope of the disclosed technology, and it is understood that such equivalent embodiments are to be included herein.

The following abbreviations are used herein: AIC, anterior limb internal capsule; BST, bed nucleus of the stria terminals; CMPF, centromedian and parafascicularis; CNS, central nervous system; DREZ, dorsal root entry zone; GF, genitofemoral; GNI, glial neuronal cell interaction; GPI, globus pallidus internus; MCS, motor cortex stimulation; MD, movement disorder; MI, primary motor cortex; ONS, occipital nerve stimulation; NAcc, nucleus accumbens; NTS, nucleus tractus solitarii; PVG, periventricular grey matter; PAG, periaqueductal grey matter; PPN, pedunculopontine nucleus; SCA, superior cerebellar artery; SCS, spinal cord stimulation; SMA, supplementary motor area; SPG, sphenopalatine ganglion; STN, subthalamic nucleus; Vcpc, ventro caudalis parvocellularis; VIP, ventral intermedia nucleus; VOA, ventralis oralis anterior; VOP, ventralis oralis posterior; VPL, ventral posterolateral nucleus; VPM, ventral posteromedial nucleus; WDR, wide dynamic range; ZI, zona incerta.

Recent animal studies have shown that application of electrical stimulation to the dorsal root entry zone (DREZ) at frequencies between 2 kHz and 100 kHz suppresses wide dynamic range (WDR) neuron response by 70% in response to noxious stimulation (Cuellar 2012). Inhibition of WDR firing was found to persist for seconds to minutes after stimulation ended. WDR neurons (also known as convergent neurons) are one of three types of second order projection neurons. WDR neuron firing is correlated with pain perception, with firing rate increasing steadily as stimulus intensity increases. Thus, these data suggest that electrical stimulation at the tested frequencies functions in part by direct axonal inhibition.

Glial cells were traditionally thought to play primarily a structural role in the nervous system, for example by surrounding neurons, holding neurons in place, providing electrical insulation, and destroying pathogens. However, glial cells may play a role in the transmission of chronic pain by releasing various mediators such as nitric oxide, proinflammatory cytokines, excitatory amino acids, and prostaglandins. Release of these mediators may cause the release of substance P and excitatory amino acids by peripheral nerves as well as modify local neural interactions in the CNS, which in turn results in action potential generation or neural responses to synaptic inputs. Substance P and excitatory amino acid release can also further activate glial cells, creating a positive feedback loop. Glial cells form a network with themselves and communicate via slow inward calcium currents, which are activated by a variety of factors including potassium. Electrical stimulation with appropriate signal parameters may be used to reduce extracellular potassium levels by primary afferent inhibition, thereby reducing glial cell activity.

Neurons and certain glial cells contain sodium channels that are responsible for the rising phase of action potentials. When exposed to low frequencies, all of these sodium channels exhibit changes in their conductance. At higher frequencies, however, these changes are specific to fast sodium channels such as NaV1.8 and NaV1.9, which are overly active in chronic pain. Without being bound to a particular theory, electrical stimulation with appropriate signal parameters may derive pain reduction in part from its ability to change the conductance of fast sodium channels in neurons and/or glial cells, thereby specifically downregulating those sodium channels that are most involved with chronic pain.

As disclosed herein, electrical stimulation, with the therapy signal parameters disclosed herein, can be used to normalize pathological neural networks associated with fast sodium channel activity and/or expression by attenuating pathology-induced sodium channel activity and modulating glial neuronal cell interaction (GNI). GNI accordingly refers generally to interactions with a glial/neuronal component, including interactions between (a) glial cells and other glial cells, (b) glial cells and neurons, (c) glial networks and neurons, and/or (d) glial networks and neural networks. Based on this, the present application provides methods and devices for attenuating pathology-induced sodium channel activity, (and/or other pathology-induced ionophores or membrane channel activity) modulating GNI, and treating various conditions associated with fast sodium channel activity and/or expression and GNI.

In certain embodiments, methods are provided for attenuating pathology-induced sodium channel activity by applying electrical stimulation, with the therapy signal parameters disclosed herein, to a target tissue or organ. This attenuation may result in decreased activity and/or expression of one or more fast sodium channels, including for example NaV1.8 or NaV1.9. In certain embodiments, decreased activity and/or expression of one or more fast sodium channels results in decreased glial cell and/or neuronal activity. In certain embodiments, attenuation of pathology-induced sodium channel activity may also result in increased activity and/or expression of one or more slow sodium channels, including for example NaV1.3.

In certain embodiments, methods are provided for modulating GNI by applying electrical stimulation, with the therapy signal parameters disclosed herein, to a target tissue or organ. In certain embodiments, this modulation may result in a decrease in the release of one or more mediators by glial cells, including for example nitric oxide, proinflammatory cytokines, excitatory amino acids, and prostaglandins. In certain embodiments, this decrease may result in a decrease in action potential generation by one or more peripheral nerves or neural elements in CNS networks, and in certain of these embodiments, the decrease may result in reduction or cessation of one or more symptoms of a medical condition (e.g., chronic pain).

In certain embodiments, methods are provided for treating a condition associated with fast sodium channel activity and/or expression, or a condition for which attenuated fast sodium channel activity and/or expression is expected to be beneficial, by applying electrical stimulation, with the therapy signal parameters disclosed herein, to a target tissue or organ. In certain embodiments, the condition being treated is selected from the group consisting of a chronic pain condition, a movement disorder, dysautonomia, an anxiety disorder, a cognitive disorder, a development disorder, a metabolic disease, or a mood disorder.

In certain embodiments, methods are provided for treating a chronic pain condition by applying electrical stimulation, with the therapy signal parameters disclosed herein, to a target tissue or organ. In certain of these embodiments the chronic pain condition is a headache pain syndrome, fascial pain syndrome, neck and brachial plexus pain syndrome, shoulder pain syndrome, elbow pain syndrome, other upper extremity pain syndrome, wrist pain syndrome, hand pain syndrome, chest wall pain syndrome, thoracic spine pain syndrome, abdominal & groin pain syndrome, lumbar spine & sacroiliac joint pain syndrome, pelvic pain syndrome, hip & lower extremity pain syndrome, knee pain syndrome, ankle pain syndrome, foot pain syndrome, visceral pain or whole body pain syndromes. In certain of these embodiments, the chronic pain disorder may be a condition listed in Table 1. Table 1 provides various spinal cord, cortical, sub-cortical, and/or peripheral targets for applying electrical stimulation in the treatment of each condition. Treatment may be carried out by applying electrical stimulation to any of the targets listed, or to a combination thereof. The list of targets is not exhaustive, meaning that there may be one or more additional targets for each condition.

TABLE 1

| Chronic pain conditions | | | | |
|---|---|---|---|---|
| Indication | Spinal Cord Target | Cortical Target | Sub-Cortical Target | Peripheral Target |
| Headache Pain Syndromes | C2-C4, (e.g., C2-C3) | Motor cortex stimulation (MCS), Posterior cingulum and cingulate gyrus. | Periventricular grey matter (PVG), periaqueductal grey matter (PAG), (nociceptive pain); internal capsule, ventral posterolateral nucleus (VPL), ventral posteromedial nucleus (VPM) (neuropathic pain) | Sphenopalatine ganglion (SPG) |
| Herpes Zoster (shingles) - Trigeminal | Appropriate spinal level | Posterior cingulum and cingulate gyrus. | Ventro caudalis parvocellularis (Vcpc), thalamus, NAcc | Gasserian ganglion, Sphenopalatine ganglion (SPG) |
| Migraine | C1-C2 | Posterior cingulum and cingulate gyrus. | Hypothalamus | Sphenopalatine ganglion (SPG), Gasserian ganglion, occipital nerve stimulation (ONS) |
| Cluster | | | Hypothalamus | SPG, Gasserian ganglion |
| Analgesic Rebound | | | PVG, PAG | |
| Occipital Neuralgia | C1-C2 | | PVG, PAG, Vcpc | ONS |
| Fascial Pain Syndromes | C2-C4, (e.g., C2-C3) | MCS, Posterior cingulum and cingulate gyrus. | Vcpc, thalamus | SPG, Gasserian ganglion |
| Trigeminal Neuralgia | | | Vcpc, thalamus | SPG, Gasserian ganglion |
| Temporomandibular Joint Dysfunction | | | Vcpc, thalamus | SPG, Gasserian ganglion, superficial temporal nerve |
| Trigeminal Neuropathy (aka Atypical Facial Pain) | | MCS, Posterior cingulum and cingulate gyrus | Vcpc, thalamus, NAcc | SPG, Gasserian ganglion, superficial temporal nerve |
| Myofascial Pain Syndrome - Face | | Posterior cingulum and cingulate gyrus | NAcc | SPG, Gasserian ganglion, superficial temporal nerve |
| Cancer Pain | | Insular cortex, Posterior cingulum and cingulate gyrus | PVG, PAG, nucleus accumbens (NAcc), Vcpc Thalamus | SPG, Gasserian ganglion, superficial temporal nerve |
| Hyoid Syndrome | C1-C3 | | | SPG, Gasserian ganglion, superficial temporal nerve |
| Reflex Sympathetic Dystrophy-Face | | Insular Cortex, Posterior cingulum and cingulate gyrus | Vcpc, thalamus, hypothalamus | SPG, Gasserian ganglion |
| Neck & Brachial Plexus Pain Syndromes | C2-C6, (e.g., C3-C4) | | | |
| Cervical Facet Syndrome | Appropriate somatotopic spinal level | | | |
| Cervical Radiculopathy | Appropriate somatotopic spinal level | | | |
| Fibromyalgia - Cervical Musculature | Appropriate somatotopic spinal level | | | |
| Myofascial Pain | Appropriate | | | |

TABLE 1-continued

Chronic pain conditions

| Indication | Spinal Cord Target | Cortical Target | Sub-Cortical Target | Peripheral Target |
|---|---|---|---|---|
| Syndrome - Cervical Musculature | somatotopic spinal level | | | |
| Brachial Plexopathy | C3-C8 (depending on site of pain) | MCS, Posterior cingulum and cingulate gyrus | Vcpc, thalamus, PAG, PVG, centromedian and parafascicularis (CMPF), NAcc | |
| Pancoast Syndrome | C3-C5 | Posterior cingulum and cingulate gyrus | PVG, PAG, pulvinar | |
| Thoracic Outlet Syndrome | C4 or C8 | | | |
| Shoulder Pain Syndromes | C2-C6, (e.g., C3-C5) | MCS, , Posterior cingulum and cingulate gyrus | Vcpc thalamus, PAG, PVG, CMPF, NAcc | Brachial plexus |
| Arthritis Pain - Shoulder | C3-C5 | MCS, Posterior cingulum and cingulate gyrus | Vcpc thalamus, PAG, PVG, CMPF, NAcc | Brachial plexus |
| Acromioclavicular Joint Pain | C4 | | | Brachial plexus |
| Myofascial Pain Syndrome - Shoulders | C4 | | | Brachial plexus |
| Subdeltoid Bursitis | C4 | | | Brachial plexus |
| Bicipital Tendonitis | C4 | | | Brachial plexus |
| Supraspinatus Syndrome | C2-C4 | | | Brachial plexus |
| Rotator Cuff Tear | C3-C5 (e.g., post-surgery) | | | Brachial plexus |
| Deltoid Syndrome | C-C5 | | | Brachial plexus |
| Teres Major Syndrome | C3-C6 | | | Brachial plexus |
| Scapulocostal Syndrome | C3-C7 | | | Brachial plexus |
| Elbow Pain Syndromes | C2-C6, (e.g., C3-C5) | | | Brachial plexus/ ulnar nerve |
| Arthritis Pain-Elbow | C4-C8 | | | |
| Tennis Elbow | C6-C8 | | | |
| Golfer's Elbow | C6-C8 | | | |
| Anconeus Compartment Syndrome | C6-C8 | | | |
| Supinator Syndrome | C6-C8 | | | |
| Brachioradialis Syndrome | C6-C8 | | | |
| Ulnar Nerve Entrapment At The Elbow | C6-C8 | | | |
| Lateral Antebrachial Cutaneous Nerve Syndrome | C6-C8 | | | |
| Olecranon Bursitis | C6-C8 | | | |
| Other Upper Extremity Pain Syndromes | C2-C6, (e.g., C3-C5) | | | Brachial plexus |
| Phantom Limb Pain | C2-C8, L1-S1 | MCS, post-cingulum, insula | Vcpc, cingulum, NAcc | |
| Wrist Pain Syndromes | C2-C6, (e.g., C3-C5) | | | |
| Arthritis Pain - Wrist | C6-C8 | | | |
| Carpal Tunnel Syndrome | C6-C8 (e.g., post-surgery) | | | |
| De Quervain's Tenosynovitis | C5-C6 | | | |
| Arthritis Pain - Carpometacarpal Joints | C6-T1 | | | |

TABLE 1-continued

Chronic pain conditions

| Indication | Spinal Cord Target | Cortical Target | Sub-Cortical Target | Peripheral Target |
|---|---|---|---|---|
| Hand Pain Syndromes | C2-C6, (e.g., C3-C5) | | | |
| Arthritis Pain - Fingers | C5-T1 | | | |
| Trigger Thumb | C5-C7 | | | |
| Trigger Finger | C5-C7 | | | |
| Ganglion Cysts of Wrist & Hand | C5-C7 | | | |
| Sesamoiditis of the Hand | C5-C7 | | | |
| Chest Wall Pain Syndromes | T1-T12 | | | |
| Intercostal Neuralgia | Level of neuralgia | | | Costal Nerve |
| Post-Thoracotomy Pain | Level of surgery +/−1 level | | | |
| Thoracic Spine Pain Syndromes | T1-T12 | | | |
| Cancer Pain | Level of pain +2 levels | Insular cortex, post cingulate cortex | PVG, PAG, cingulum, NAcc | |
| Costovertebral Arthritis Pain | Center on dermatome | | | |
| Postherpetic Neuralgia | Center on dermatome | | NAcc, Vc Thalmus | Center on dermatome |
| Abdominal & Groin Pain Syndromes | T6-T12 | | | Left vagus nerve, subdiaphragmatic right vagus nerve |
| Cancer Pain | | Insular cortex, posterior cingulate cortex | PVG, PAG, NAcc, cingulum | |
| Chronic Pancreatitis | | Insular cortex, posterior cingulate cortex | | Left vagus nerve, subdiaphragmatic right vagus nerve |
| Ilioinguinal Neuralgia | | | | Ilioinguinal nerve (field app) |
| Visceral Pain (peritoneum, stomach, duodenum, intestine, colon, liver, spleen, pancreas, kidney, adrenal gland, appendix, gall bladder) | | Insular cortex, posterior cingulate cortex | PVG, PAG, NAcc, cingulum | Left vagus |
| Post-vasectomy Pain Syndrome | | | | Genitofemoral (GF) nerve |
| Genitofemoral Neuralgia | | | | GF nerve |
| Lumbar Spine & Sacroiliac Joint Pain Syndromes | T8-T12 | Insular cortex, post cingulate cortex | PVG, PAG, NAcc, cingulum, Vcpc | |
| Myofascial Pain Syndrome | T8-T12 | | | |
| Lumbar Radiculopathy | Segment appropriate +/− 2 levels | | | |
| Latissimus Dorsi Muscle Syndrome | Upper thoracic | | | |
| Arachnoiditis | S1-L3 (tune to area of pain) | Insular cortex, posterior cingulate cortex | PVG, PAG NAcc, cingulum | |
| Sacroiliac Joint Pain | S1 and L1 | Insular cortex, post cingulate cortex | | |

TABLE 1-continued

Chronic pain conditions

| Indication | Spinal Cord Target | Cortical Target | Sub-Cortical Target | Peripheral Target |
|---|---|---|---|---|
| Pelvic Pain Syndromes | T12-L5 | | | |
| Cancer Pain | NO | Insular cortex, post cingulate cortex | PVG, PAG, NAcc, cingulum | |
| Gluteus Maximus Syndrome | | | | |
| Visceral Pain (pelvis, coccyx, ovaries, fallopian tube, uterus, vulva, clitoris, perineum, urinary bladder, testicles, rectum) | | Insular cortex, posterior cingulate cortex | PVG, PAG, NAcc, PO thalamus, cingulum | Pudendal nerve |
| Piriformis Syndrome | | Insular cortex, post cingulate cortex | | |
| Ischiogluteal Bursitis | | | | Pudendal nerve |
| Levator Ani Syndrome | S3-S4 | | | Pudendal nerve |
| Coccydynia | S3-S4 | | | Pudendal nerve |
| Hip & Lower Extremity Pain Syndromes | T8-T12 | | | |
| Arthritis Pain - Hip | T11-L3 | | | |
| Meralgia Paresthetica | L1 | | | |
| Phantom Limb Pain | | MCS | Vcpc | |
| Knee Pain Syndromes | T8-T12 | | | |
| Ankle Pain Syndromes | T8-T12 | | | |
| Foot Pain Syndromes | T8-T12 | | | |
| Arthritis - Toe Pain | T10-S1 | | | |
| Bunion Pain | T10-S1 | | | |
| Plantar Fasciitis | T11-L3 | | | |
| Calcaneal Spur Syndrome | T11-L3 | | | |
| Whole Body Pain Syndromes | C2-C4 | | | |
| Cancer Pain | | Insula cortex, post cingulate cortex | PVG, PAG, cingulum, posterior thalamus | |
| Chronic Regional Pain Syndrome - Multiple Limb | C4-C8, T8-T12 | Insular cortex, post cingulate cortex | Hypothalamus, posterior thalamus | |
| Phantom pain syndromes | | Insular cortex, posterior cingulate cortex, S1, S2 cortex | Cingulum, PVG, PAG, Vcpc, thalamus | |

In certain embodiments, methods are provided for treating a movement disorder by applying electrical stimulation, with the therapy signal parameters disclosed herein, to a target tissue or organ. In certain of these embodiments, the movement disorder may be a condition listed in Table 2. Table 2 provides various spinal cord, cortical, sub-cortical, and/or peripheral targets for applying electrical stimulation in the treatment of each condition. Treatment may be carried out by applying electrical stimulation to any of the targets listed, or to a combination thereof. The list of targets is not exhaustive, meaning that there may be one or more additional targets for each condition.

TABLE 2

Movement disorders

| Indication | Spinal Cord Target | Cortical Target | Sub-Cortical Target | Peripheral Target |
|---|---|---|---|---|
| Akathisia (inability to sit still) | | Primary motor cortex (MI), supplementary motor area (SMA) | STN, Globus pallidus internus (GPI), ventralis oralis anterior (VOA), ventralis oralis posterior (VOP), subthalamic nucleus (STN) | |
| Akinesia (lack of movement) | | | STN, Pedunculopontine nucleus (PPN), mid-thalamic intralaminar and reticular nuclei | |
| Associated Movements (Mirror Movements or Homolateral Synkinesis) | | MI, SMA | GPI, VOA, VOP, STN, zona incerta (ZI), area Q | |
| Athetosis (contorted torsion or twisting) | | MI, SMA | GPI, VOA, VOP, STN | |
| Ataxia (gross lack of coordination of muscle movements) | | MI, SMA | GPI, VOA, VOP, STN | |
| Ballismus (violent involuntary rapid and irregular movements) | | MI, SMA | GPI, VOA, VOP, STN | |
| Hemiballismus (affecting only one side of the body) | | | GPi, VoA, VoP, STN | |
| Bradykinesia (slow movement) | | MI, SMA | GPI, VOA, VOP, STN | |
| Cerebral Palsy | | MI, SMA | Deep cerebellar nuclei | |
| Chorea (rapid, involuntary movement) | | MI, SMA | GPI, VOA, VOP, STN | |
| Sydenham's Chorea | | MI, SMA | GPI, VOA, VOP, STN | |
| Rheumatic Chorea | | MI, SMA | GPI, VOA, VOP, STN | |
| Huntington's Disease | | MI, SMA | GPI, VOA, VOP, STN | |
| Dystonia (sustained torsion) | | MI, SMA | GPI, VOA, VOP, STN | |
| Dystonia DTY1, DTY11 and generalized dystonia | | MI, SMA | GPI, VOA, VOP, STN | |
| Blepharospasm | | MI, SMA | GPI, VOA, VOP STN | |
| Writer's Cramp | | MI, SMA | GPI, VOA, VOP STN | |
| Spasmodic Torticollis (twisting of head and neck) | | MI, SMA | GPI, VOA, VOP STN | |
| Dopamine-Responsive Dystonia (hereditary progressive dystonia with diurnal fluctuation or Segawa's disease) | | MI, SMA | GPI, VOA, VOP STN | |
| Geniospasm (episodic involuntary up and down movements of the chin and lower lip) | | MI, SMA | GPI, VOA, VOP STN | |
| Myoclonus (brief, involuntary twitching of a muscle or a group of muscles) | | MI, SMA | GPI, VOA, VOP STN | |
| Metabolic General Unwellness Movement Syndrome (MGUMS) | | MI, SMA | GPI, VOA, VOP STN | |
| Parkinson's Disease | | Motor cortex, pre-motor cortex | Subthalamic nucleus, GPI, ZI, pallidofugal fibers | |
| Spasms (contractions) | | | Superior cerebellar artery (SCA), Superior Cerebellar structures, deep cerebellar nuc | |
| Tardive dyskinesia | | | STN, GPI, VOA, VOP | |
| Tic Disorders (involuntary, compulsive, repetitive, stereotyped) | | | Anterior limb internal capsule (AIC), VOA, CMPF thalamus | |
| Tourette's Syndrome | | | AIC, GPI, VOA, VOP, STN, CMPF | |
| Tremor (oscillations) | | | Ventral intermedia nucleus (VIM), Area Q, ZI | |
| Rest Tremor (4-8 Hz) | | | STN, GPI, Area Q, ZI | |
| Postural Tremor | | | STN, VIM, Area Q, ZI | |
| Kinetic Tremor | | | VIM, Area Q, ZI | |
| Essential Tremor (6-8 Hz variable amplitude) | | | VIM, Area Q, ZI | |

TABLE 2-continued

Movement disorders

| Indication | Spinal Cord Target | Cortical Target | Sub-Cortical Target | Peripheral Target |
|---|---|---|---|---|
| Cerebellar tremor (6-8 Hz variable amplitude) | | | VIM, deep cerebellar nuclei, Area Q | |
| Parkinsonian tremors (4-8 Hz variable amplitude) | | | STN +/− VIM | |
| Physiological tremor (10-12 Hz low amplitude) | | | VIM, Area Q, ZI | |
| Wilson's disease | | | VIM and/or STN | |

In certain embodiments, methods are provided for treating a dysautonomic condition by applying electrical stimulation, with the therapy signal parameters disclosed herein, to a target tissue or organ. In certain of these embodiments, the dysautonomic condition may be a condition listed in Table 3. Table 3 provides various spinal cord, cortical, sub-cortical, and/or peripheral targets for applying electrical stimulation in the treatment of each condition. Treatment may be carried out by applying electrical stimulation to any of the targets listed, or to a combination thereof. The list of targets is not exhaustive, meaning that there may be one or more additional targets for each condition.

TABLE 3

Dysautonomic conditions

| Indication | Spinal Cord Target | Cortical Target | Sub-Cortical Target | Peripheral Target |
|---|---|---|---|---|
| Postural Orthostatic Tachycardia Syndrome (POTS) | T2-T5 | insula | Hypothalamus | |
| Inappropriate Sinus Tachycardia (IST) | T2-T5 | insula | Hypothalamus | |
| Vasovagal Syncope | T2-T5 | insula | NTS | |
| Neurocardiogenic Syncope (NCS) | | insula | Nucleus tractus solitarii (NTS) | Right vagus nerve, left vagus nerve |
| Neurally Mediated Hypotension (NMH) | | insula | Hypothalamus | |
| Autonomic Instability | T2-T5 | insula | | |

In certain embodiments, methods are provided for treating an anxiety disorder by applying electrical stimulation, with the therapy signal parameters disclosed herein, to a target tissue or organ. In certain of these embodiments, the anxiety disorder may be a condition listed in Table 4. Table 4 provides various spinal cord, cortical, intra-cortical, and/or peripheral targets for applying electrical stimulation in the treatment of each condition. Treatment may be carried out by applying electrical stimulation to any of the targets listed, or to a combination thereof. The list of targets is not exhaustive, meaning that there may be one or more additional targets for each condition.

TABLE 4

Anxiety disorders

| Indication | Spinal Cord Target | Cortical Target | Intra-Cortical Target | Peripheral Target |
|---|---|---|---|---|
| Generalized Anxiety Disorder | | Parietal, prefrontal | Amygdala, insula, cingulate, DM thalamus | |
| Phobic Disorder | | Insular cortex, medial prefrontal cortex, anterior cingulate cortex, ventromedial prefrontal cortex | Corpus callosum, hippocampus, ventral striatum, bed nucleus of the stria terminals (BST), amygdala, septal nuclei | |
| Specific Phobias (e.g., arachnophobia, acrophobia) | | Insular cortex, medial prefrontal cortex, anterior cingulate cortex, ventromedial prefrontal cortex | Amygdala, NAcc, septal nuclei | |
| Social Phobias, (e.g., public speaking, crowded areas) | | Insular cortex, medial prefrontal cortex, anterior cingulate cortex, ventromedial prefrontal cortex | Amygdala, NAcc, septal nuclei | |
| Agoraphobia | | Insular cortex, medial prefrontal cortex, anterior cingulate cortex, ventromedial prefrontal cortex | NAcc, BST, amygdala | |
| Panic Disorder | | Insular cortex, medial prefrontal cortex, anterior cingulate cortex, ventromedial prefrontal cortex | NAcc, BST, ventral striatum, DM thalamus | |
| Obsessive Compulsive Disorder (OCD) | | Cg 25-cingulate cortex, orbitofrontal cortex | AIC, CMPF thalamus | |

In certain embodiments, methods are provided for treating a cognitive disorder by applying electrical stimulation, with the therapy signal parameters disclosed herein, to a target tissue or organ. In certain of these embodiments, the cognitive disorder may be a condition listed in Table 5. Table 5 provides various spinal cord, cortical, sub-cortical, and/or peripheral targets for applying electrical stimulation in the treatment of each condition. Treatment may be carried out by applying electrical stimulation to any of the targets listed, or to a combination thereof. The list of targets is not exhaustive, meaning that there may be one or more additional targets for each condition.

TABLE 5

Cognitive disorders

| Indication | Spinal Cord Target | Cortical Target | Sub-Cortical Target | Peripheral Target |
|---|---|---|---|---|
| Dementia | | Entorhinal cortex, hippocampus | Precommissural fornix | |
| Amnesia | | Entorhinal cortex, hippocampus | Precommissural fornix | |

In certain embodiments, methods are provided for treating a development disorder by applying electrical stimulation, with the therapy signal parameters disclosed herein, to a target tissue or organ. In certain of these embodiments, the development disorder may be a condition listed in Table 6. Table 6 provides various spinal cord, cortical, sub-cortical, and/or peripheral targets for applying electrical stimulation in the treatment of each condition. Treatment may be carried out by applying electrical stimulation to any of the targets listed, or to a combination thereof. The list of targets is not exhaustive, meaning that there may be one or more additional targets for each condition.

TABLE 6

Development disorders

| Indication | Spinal Cord Target | Cortical Target | Intra-cortical Target | Peripheral Target |
|---|---|---|---|---|
| Motor disorders | | | GPI, VOA, VOP, deep cerebellar nuclei, Cerebellar vermis | |

In certain embodiments, methods are provided for treating a metabolic disease by applying electrical stimulation, with the therapy signal parameters disclosed herein, to a target tissue or organ. In certain of these embodiments, the metabolic disease may be selected from the group consisting of diabetes mellitus, an acid-base imbalance, a metabolic brain disease, a calcium metabolism disorder, a DNA repair deficiency disorder, an inborn metabolic error disorder, a mitochondrial disease, or a porphyria, and in certain of these embodiments the metabolic disease may be a condition listed in Table 7. Table 7 provides various spinal cord, cortical, sub-cortical, and/or peripheral targets for applying electrical stimulation in the treatment of each condition. Treatment may be carried out by applying electrical stimulation to any of the targets listed, or to a combination thereof. The list of targets is not exhaustive, meaning that there may be one or more additional targets for each condition.

TABLE 7

Metabolic diseases

| Indication | Spinal Cord Target | Cortical Target | Sub-Cortical Target | Peripheral Target |
|---|---|---|---|---|
| Diabetes Mellitus | | | | |
| Type I Diabetes | | | Hypothalamus | Splenic and gastric nerve |
| Type II Diabetes | | | Hypothalamus | Splenic and gastric nerve |
| Acid-Base Imbalance | | | Hypothalamus, subfornical organ of pines | |
| Acidosis+ | | | Hypothalamus, subfornical organ of pines | |
| Alkalosis+ | | | Hypothalamus, subfornical organ of pines | |
| Brain Diseases, Metabolic | | | | |
| Hepatic Encephalopathy (HE) | | | GPI, VOA, VOP, thalamus | |
| Kernicterus | | | GPI, VOA, VOP, thalamus | |
| Mitochondrial Encephalo-myopathies | | | GPI, VOA, VOP, thalamus | |
| Wernicke Encephalopathy | | Entorhinal cortex | Fornix, mammillary bodies | |
| DNA Repair Deficiency Disorders | | | | |
| Ataxia Telangiectasia | | | GPI, VOA, VOP, thalamus | |
| Bloom Syndrome | | | GPI, VOA, VOP, thalamus | |
| Cockayne Syndrome | | | GPI, VOA, VOP, thalamus | |
| Fanconi Anemia | | | GPI, VOA, VOP, thalamus | |
| Metabolism, Inborn Errors | | | GPI, VOA, VOP (to the extent subjects have movement disorders (MDs)) | |
| Amino Acid Metabolism, Inborn Errors+ | | | GPI, VOA, VOP (to the extent subjects have MDs) | |
| Amino Acid Transport Disorders, Inborn+ | | | GPI, VOA, VOP (to the extent subjects have MDs) | |
| Amyloidosis, Familial+ | | | GPI, VOA, VOP (to the extent subjects have MDs) | |
| Brain Diseases, Metabolic, Inborn+ | | | GPI, VOA, VOP (to the extent subjects have MDs) | |
| Carbohydrate Metabolism, Inborn Errors+ | | | GPI, VOA, VOP (to the extent subjects have MDs) | |
| Hyper-bilirubinemia, Hereditary+ | | | GPI, VOA, VOP (to the extent subjects have MDs) | |
| Lipid Metabolism, Inborn Errors+ | | | GPI, VOA, VOP (to the extent subjects have MDs) | |
| Lysosomal Storage Diseases+ | | | GPI, VOA, VOP (to the extent subjects have MDs) | |

TABLE 7-continued

Metabolic diseases

| Indication | Spinal Cord Target | Cortical Target | Sub-Cortical Target | Peripheral Target |
|---|---|---|---|---|
| Metal Metabolism, Inborn Errors+ | | | GPI, VOA, VOP (to the extent subjects have MDs) | |
| Peroxisomal Disorders+ | | | GPI, VOA, VOP (to the extent subjects have MDs) | |
| Porphyrias+ | | | GPI, VOA, VOP (to the extent subjects have MDs) | |
| Mitochondrial Diseases | | | GPI, VOA, VOP (to the extent subjects have MDs) | |
| Optic Atrophy, Autosomal Dominant | | CNS visual prosthesis @V1 | | |
| Optic Atrophy, Hereditary, Leber | | CNS visual prosthesis @V1 | | |
| Pyruvate Carboxylase Deficiency Disease | | | GPI, VOA, VOP (to the extent subjects have MDs) | |
| Pyruvate Dehydrogenase Complex Deficiency Disease | | | GPI, VOA, VOP (to the extent subjects have MDs) | |
| Porphyrias | | | | |
| Porphyria, Erythropoietic | | | GPI, VOA, VOP (to the extent subjects have MDs) | |

In certain embodiments, methods are provided for treating a mood disorder by applying electrical stimulation, with the therapy signal parameters disclosed herein, to a target tissue or organ. In certain of these embodiments, the mood disorder may be a condition listed in Table 8. Table 8 provides various spinal cord, cortical, sub-cortical, and/or peripheral targets for applying electrical stimulation in the treatment of each condition. Treatment may be carried out by applying electrical stimulation to any of the targets listed, or to a combination thereof. The list of targets is not exhaustive, meaning that there may be one or more additional targets for each condition.

TABLE 8

Mood disorders

| Indication | Spinal Cord Target | Cortical Target | Sub-Cortical Target | Peripheral Target |
|---|---|---|---|---|
| Depressive Disorders | | Dorsolater prefrontal cortex, orbitofrontal cortex, Cg25, Posterior cingulate cortex | Subgenual cingulum, posterior cingulum, NAcc, ventral capsule/ventral striatum, inferior thalamic peduncle, lateral habenula, AIC, BST | |
| Major depressive disorder (MDD) | | Cg25, Posterior cingulate cortex | Subgenual cingulum, posterior cingulum, NAcc, ventral capsule/ventral striatum, inferior thalamic peduncle, lateral habenula, AIC, BST | |
| Dysthymia | | Cg25, posterior cingulate cortex | Subgenual cingulum, posterior cingulum, NAcc, ventral capsule/ventral striatum, inferior thalamic peduncle, lateral habenula, AIC, BST | |
| Double depression | | Cg25, posterior cingulate cortex | Subgenual cingulum, posterior cingulum, NAcc, ventral capsule/ventral striatum, inferior thalamic peduncle, lateral habenula, AIC, BST | |
| Depressive Disorder Not Otherwise Specified (DD-NOS) | | Cg25, posterior cingulate cortex | Subgenual cingulum, posterior cingulum, NAcc, ventral capsule/ventral striatum, inferior thalamic peduncle, lateral habenula, AIC, BST | |

In certain embodiments, methods are provided for treating a visceral pain syndromes by applying electrical stimulation, with the therapy signal parameters disclosed herein, to a target tissue or organ. In certain of these embodiments, the visceral pain syndrome may be a condition listed in Table 9. Table 9 provides various spinal cord, cortical, sub-cortical, and/or peripheral targets for applying electrical stimulation in the treatment of each condition. Treatment may be carried out by applying electrical stimulation to any of the targets listed, or to a combination thereof. The list of targets is not exhaustive, meaning that there may be one or more additional targets for each condition.

TABLE 9

Visceral Pain Syndromes

| Indication | Spinal target | Cortical target | Subcortical target | Peripheral target |
|---|---|---|---|---|
| Cystitis | S2-4 | Insula, S1, S2 | Vc thalamus, posterior thalamic nuclei | Pudendal nerve |
| IBS | T3-9, L1 | Insula, S1, S2 | | R or L Vagus nerve, splanchnic nerves |
| Mesenteric ischemia | T3-9 | Insula | | |
| Idiopathic abdominal pain | T3-9 | Insula | Vc, DM thalamus, Posterior thalamic nuc. | Splanchnic nerve, R or L vagus nerve |

"Treating" or "treatment" as used herein with regard to a condition may refer to preventing the condition, reducing, or ending symptoms associated with the condition; generating a complete or partial regression of the condition; or some combination thereof. "Preventing" or "prevention" as used herein with regard to a condition may refer to total or partial prevention of the condition or symptoms associated with the condition.

In certain embodiments, electrical stimulation is performed with at least a portion of the therapy signal at a frequency in a frequency range between about 2 Hz and about 100 kHz; between about 1.5 kHz and about 50 KHz; between about 3 kHz and about 20 KHz; between about 3 kHz and about 15 kHz; or between about 5 kHz and about 15 KHz; or at frequencies of about 5 kHz, about 6 kHz, about 7 kHz, about 8 kHz, about 9 kHz, about 10 KHz, about 11 kHz, or about 12 kHz; and in one embodiment, surprisingly effective results have been found when treating certain medical conditions with frequencies between 5 KHz and 15 kHz, and in one embodiment 10 KHz. (The term "about" is intended to represent +/−10%, or a range as would be understood as reasonably equivalent by one of ordinary skill in the art.)

In various embodiments, the electrical stimulation may be applied with at least a portion of the therapy signal at amplitudes within amplitude ranges of: about 0.1 mA to about 20 mA; about 0.5 mA to about 10 mA; about 0.5 mA to about 7 mA; about 0.5 mA to about 5 mA; about 0.5 mA to about 4 mA; about 0.5 mA to about 2.5 mA; and in one embodiment, surprisingly effective results have been found when treating certain medical conditions with amplitudes below 7 mA.

In various embodiments, the electrical stimulation may be applied with at least a portion of the therapy signal having a pulse width within a pulse width range of from about 10 microseconds to about 333 microseconds; from about 10 microseconds to about 166 microseconds; from about 25 microseconds to about 166 microseconds; from about 25 microseconds to about 100 microseconds; from about 30 microseconds to about 100 microseconds; from about 33 microseconds to about 100 microseconds; from about 50 microseconds to about 166 microseconds; and in one embodiment, surprisingly effective results have been found when treating certain medical conditions with pulse widths from about 25 microseconds to about 100 microseconds; and from about 30 microseconds to about 40 microseconds. In a particular embodiment, the therapy signal at a frequency in a frequency range of 1.5 kHz to 100 kHz, a pulse width in a pulse width range of 10 microseconds to 333 microseconds and an amplitude in an amplitude range of 0.1 mA to 20 mA. The therapy signal can be applied at a duty cycle of 5% to 75%, and can be applied to thoracic spinal cord locations to treat back and/or leg pain, e.g., chronic back and/or leg pain. In another particular embodiment, a therapy signal having a pulse width is applied to the spinal cord at a pulse width in a pulse width range of 10 microseconds to 333 microseconds at any of a variety of suitable frequencies (within or outside the range of 1.5 kHz to 100 kHz) to treat a variety of pain indications, including but not limited to chronic low back pain and/or leg pain.

Application of electrical stimulation in conjunction with the methods disclosed herein can be carried out using suitable devices and programming modules specifically programmed to carry out any of the methods described herein. A variety of devices for administering an electrical signal to a target tissue or organ are taught in the references incorporated by reference above. Other examples of devices for administering an electrical signal in conjunction with SCS are disclosed in US Patent Publications Nos. 2010/0274316 and 2010/0211135, both of which are incorporated herein by reference in their entireties. In certain embodiments, a device that is used for applying an electrical signal to the spinal cord may be repurposed with or without modifications to administer an electrical signal to another target tissue or organ, e.g., a cortical, sub-cortical, intra-cortical, or peripheral target. Electrical stimulation may be applied directly to a target tissue or organ, or it may be applied in close proximity to the target tissue or organ (i.e., close enough for the target tissue or organ to receive the electrical signal). As such, any of the herein described systems, sub-systems, and/or sub-components serve as means for performing any of the herein described methods.

In certain embodiments, electrical stimulation is applied to a tissue or organ using a device that comprises a lead, wherein the lead in turn comprises an electrode. In these embodiments, administration of electrical stimulation comprises a positioning step (e.g., placing the lead such that an electrode is in proximity to the target tissue or organ) and a stimulation step (e.g., transmitting an electrical signal (i.e., therapy signal) through the electrode).

FIG. 1 schematically illustrates a representative treatment system 100 for administering electrical stimulation to the spinal cord 191 in conjunction with the methods disclosed herein. The system 100 can include a pulse generator 101, which may be implanted subcutaneously within a patient 190 and coupled to a signal delivery element 110. In a representative example, the signal delivery element 110 includes one or more leads or lead bodies 111 (shown as first and second leads 111a, 111b) that carry features for delivering therapy to the patient 190 after implantation. The pulse generator 101 can be connected directly to the lead 111, or it can be coupled to the lead 111 via a communication link 102 (e.g., an extension). Accordingly, the lead 111 can include a terminal section that is releasably connected to an extension at a break 114 (shown schematically in FIG. 1). This allows a single type of terminal section to be used with patients of different body types (e.g., different heights). The terms "lead" and "lead body" as used herein include any of a number of suitable substrates and/or support members that carry devices for providing therapy signals to the patient 190. For example, the lead 111 can include one or more electrodes or electrical contacts that direct electrical signals into the patient's tissue. In other embodiments, the signal delivery element 110 can include devices other than a lead body (e.g., a paddle) that also direct electrical signals to the patient 190.

The pulse generator 101 can transmit electrical signals to the signal delivery element 110 that attenuate pathology-induced sodium channel activity and/or modulate GNI. The pulse generator 101 can include a machine-readable (e.g., computer-readable) medium containing instructions for generating and transmitting suitable therapy signals. The pulse generator 101 and/or other elements of the system 100 can include one or more processors 107, memories 108 and/or input/output devices. Accordingly, the process of providing modulation signals and executing other associated functions can be performed by computer-executable instructions contained on computer-readable media, e.g., at the processor(s) 107 and/or memory(s) 108. The pulse generator 101 can include multiple portions, elements, and/or subsystems (e.g., for directing signals in accordance with multiple signal delivery parameters), housed in a single housing, as shown in FIG. 1, or in multiple housings.

The pulse generator 101 can also receive and respond to an input signal received from one or more sources. The input signals can direct or influence the manner in which the therapy instructions are selected, executed, updated and/or otherwise performed. The input signal can be received from one or more sensors 112 (one is shown schematically in FIG. 1 for purposes of illustration) that are carried by the pulse generator 101 and/or distributed outside the pulse generator 101 (e.g., at other patient locations) while still communicating with the pulse generator 101. The sensors 112 can provide inputs that depend on or reflect patient state (e.g., patient position, patient posture and/or patient activity level, or pathophysiology measurements defined as appropriate to the clinical disorder), and/or inputs that are patient-independent (e.g., time). In other embodiments, inputs can be provided by the patient and/or the practitioner, as described in further detail later.

In some embodiments, the pulse generator 101 can obtain power to generate the electrical signals from an external power source 103. The external power source 103 can transmit power to the implanted pulse generator 101 using electromagnetic induction (e.g., radiofrequency (RF) signals). For example, the external power source 103 can include an external coil 104 that communicates with a corresponding internal coil (not shown) within the implantable pulse generator 101. The external power source 103 can be portable for ease of use. In another embodiment, the pulse generator 101 can obtain the power to generate electrical signals from an internal power source, in addition to or in lieu of the external power source 103. For example, the implanted pulse generator 101 can include a non-rechargeable battery or a rechargeable battery to provide such power. When the internal power source includes a rechargeable battery, the external power source 103 can be used to recharge the battery. The external power source 103 can in turn be recharged from a suitable power source (e.g., conventional wall power).

In some cases, an external programmer 105 (e.g., a trial modulator) can be coupled to the signal delivery element 110 during an initial implant procedure, prior to implanting the pulse generator 101. For example, a practitioner (e.g., a physician and/or a company representative) can use the external programmer 105 to vary the modulation parameters provided to the signal delivery element 110 in real time, and select optimal or particularly efficacious parameters. These parameters can include the position of the signal delivery element 110, as well as the characteristics of the electrical signals provided to the signal delivery element 110. In a typical process, the practitioner uses a cable assembly 120 to temporarily connect the external programmer 105 to the signal delivery device 110. The cable assembly 120 can accordingly include a first connector 121 that is releasably connected to the external programmer 105, and a second connector 122 that is releasably connected to the signal delivery element 110. Accordingly, the signal delivery element 110 can include a connection element that allows it to be connected to a signal generator either directly (if it is long enough) or indirectly (if it is not). The practitioner can test the efficacy of the signal delivery element 110 in an initial position. The practitioner can then disconnect the cable assembly 120, reposition the signal delivery element 110, and reapply the electrical modulation. This process can be performed iteratively until the practitioner obtains the desired position for the signal delivery device 110. Optionally, the practitioner may move the partially implanted signal delivery element 110 without disconnecting the cable assembly 120. Further details of suitable cable assembly methods and associated techniques are described in US Patent Publication No. 2011/0071593, which is incorporated herein by reference in its entirety.

After the position of the signal delivery element 110 and appropriate signal delivery parameters are established using the external programmer 105, the patient 190 can receive therapy via signals generated by the external programmer 105, generally for a limited period of time. In a representative application, the patient 190 receives such therapy for one week. During this time, the patient wears the cable assembly 120 and the external programmer 105 outside the body. Assuming the trial therapy is effective or, shows the promise of being effective, the practitioner then replaces the external programmer 105 with the implanted pulse generator 101, and programs the pulse generator 101 with parameters selected based on the experience gained during the trial period. Optionally, the practitioner can also replace the signal delivery element 110. Once the implantable pulse generator 101 has been positioned within the patient 190, the signal delivery parameters provided by the pulse generator 101 can still be updated remotely via a wireless physician's programmer (e.g., a physician's remote) 117 and/or a wireless patient programmer 106 (e.g., a patient remote). Generally, the patient 190 has control over fewer parameters than does the practitioner. For example, the capability of the patient programmer 106 may be limited to starting and/or stopping the pulse generator 101, and/or adjusting the signal amplitude.

In any of the foregoing embodiments, the parameters in accordance with which the pulse generator 101 provides signals can be modulated during portions of the therapy regimen. For example, the frequency, amplitude, pulse width and/or signal delivery location can be modulated in accordance with a preset program, patient and/or physician inputs, and/or in a random or pseudorandom manner. Such parameter variations can be used to address a number of potential clinical situations, including changes in the patient's perception of one or more symptoms associated with the condition being treated, changes in the preferred target neural population, and/or patient accommodation or habituation.

In certain embodiments, electrical stimulation is applied to the dorsal column. In other embodiments, the electrical stimulation is applied to other neural tissue such as nerve roots and peripherals nerves on the spinal level, including for example the dorsal root (DN) and dorsal root ganglion (DRG) and the ventral root (VN). In other embodiments, electrical stimulation may be applied to one or more non-spinal cord tissues or organs. For example, electrical stimulation may be applied to various cortical, sub-cortical, intra-cortical, or peripheral targets. For certain conditions, electrical stimulation may be applied to a single target tissue or organ. For other conditions, electrical stimulation may be applied to multiple target tissues or organs sequentially or simultaneously. For example, where the condition is a chronic pain disorder, stimulation may be applied to the spinal cord, a cortical target, a sub-cortical target, or a combination thereof. In certain embodiments, electrical stimulation parameters are configured so as to not result in the patient experiencing paresthesia.

In certain embodiments, electrical stimulation is applied at an amplitude that is sub-threshold with regard to paresthesia and supra-threshold with regard to symptom reduction (e.g., therapy, such as pain relief). In certain of these embodiments, electrical stimulation is applied at an amplitude between about 0.5 mA to about 20 mA. In certain embodiments, electrical stimulation is applied at a duty cycle. Duty cycles can range from 1% to about 99%, or between about 5% and about 75%, or between about 10% and about 50%.

In certain embodiments of the methods provided herein, electrical stimulation may be administered on a pre-determined schedule. In other embodiments, electrical stimulation may be administered on an as-needed basis. Administration may continue for a pre-determined amount of time, or it may continue indefinitely until a specific therapeutic benchmark is reached, for example until an acceptable reduction in one or more symptoms. In certain embodiments, electrical stimulation may be administered one or more times per day, one or more times per week, once a week, once a month, or once every several months. In certain embodiments, administration frequency may change over the course of treatment. For example, a subject may receive less frequent administrations over the course of treatment as certain therapeutic benchmarks are met. The duration of each administration (e.g., the actual time during which a subject is receiving electrical stimulation) may remain constant throughout the course of treatment, or it may vary depending on factors such as patient health, internal pathophysiological measures, or symptom severity. In certain embodiments, the duration of each administration may range from 1 to 4 hours, 4 to 12 hours, 12 to 24 hours, 1 day to 4 days, or 4 days or greater.

In certain embodiments of the methods provided herein, administration of electrical stimulation may be combined with one or more additional treatment modalities. For example, electrical stimulation may be applied in combination with the administration of one or more pharmaceutical agents that block fast sodium channels. In other embodiments, electrical stimulation may be used as a replacement for other treatment modalities. For example, electrical stimulation may be administered to a subject who has previously received neuroleptics or other sodium channel blockers but who has experienced unsatisfactory results and/or negative side effects. In certain embodiments, application of electrical stimulation may result in a greater treatment effect than administration of other treatment modalities, including for example a larger reduction in symptoms or an increased duration of symptom reduction.

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention. It will be understood that many variations can be made in the procedures herein described while still remaining within the bounds of the present invention. It is the intention of the inventors that such variations are included within the scope of the invention.

EXAMPLES

Example 1. A method of attenuating pathology-induced sodium channel activity comprising applying electrical stimulation to a target neural location, wherein the electrical stimulation includes one or more system parameters as described in the embodiments above, and wherein the target neural location is chosen so as to treat the medical condition listed in Tables 1-9 above.

Example 2. A method of treating a condition associated with increased fast sodium channel comprising applying electrical stimulation to a target neural location, wherein the electrical stimulation includes one or more system parameters as described in the embodiments above, and wherein the target neural location is chosen so as to treat the medical condition listed in Tables 1-9 above.

Example 3. A method of modulating GNI comprising applying electrical stimulation to a target neural location, wherein the electrical stimulation includes one or more system parameters as described in the embodiments above, and wherein the target neural location is chosen so as to treat the medical condition listed in Tables 1-9 above.

Example 4. A neuromodulation system for treating a medical condition comprising: an implantable (or external) pulse generator configured to attenuate pathology-induced sodium channel activity by generating and applying a electrical stimulation to a target neural location, wherein the electrical stimulation includes one or more system parameters as described in the embodiments above, and wherein the target neural location is chosen so as to treat the medical condition listed in Tables 1-9 above.

Example 5. A neuromodulation system for treating a medical condition comprising: an implantable (or external) pulse generator configured to treat a condition associated with increased fast sodium channel by generating and applying a electrical stimulation to a target neural location, wherein the electrical stimulation includes one or more system parameters as described in the embodiments above, and wherein the target neural location is chosen so as to treat the medical condition listed in Tables 1-9 above.

Example 6. A neuromodulation system for treating a medical condition comprising: an implantable (or external) pulse generator configured to modulate GNI by generating and applying a electrical stimulation to a target neural location, wherein the electrical stimulation includes one or more system parameters as described in the embodiments above, and wherein the target neural location is chosen so as to treat the medical condition listed in Tables 1-9 above.

As stated above, the foregoing is merely intended to illustrate various embodiments of the present invention. The specific modifications discussed above are not to be construed as limitations on the scope of the invention. It will be apparent to one skilled in the art that various equivalents, changes, and modifications may be made without departing from the scope of the invention, and it is understood that such equivalent embodiments are to be included herein. All references cited herein are incorporated by reference as if fully set forth herein.

We claim:

1. A method for treating back or leg pain in a patient by modulating a glial neuronal cell interaction of the patient, the method comprising:
   programming a signal generator to deliver multiple electrical therapy signals to the patient's spinal cord via one or more implanted signal delivery elements to treat the patient,
   wherein the multiple electrical therapy signals have a frequency of 2 Hz to 100 KHz, and
   wherein the multiple electrical therapy signals modulate a glial neuronal cell interaction of the patient to reduce the back or leg pain in the patient.

2. The method of claim 1 wherein the multiple electrical therapy signals are delivered simultaneously.

3. The method of claim 1 wherein the one or more signal delivery elements include a lead having a plurality of electrical contacts, and wherein the multiple electrical therapy signals are delivered via different electrical contacts of the plurality of electrical contacts.

4. The method of claim 1 wherein the one or more signal delivery elements include multiple leads, and wherein the multiple electrical therapy signal are delivered via different leads.

5. The method of claim 1 wherein the multiple electrical therapy signals are delivered to the patient's spinal cord at a vertebral location between about T8 and T12.

6. The method of claim 1 wherein at least one of the multiple electrical signals does not create paresthesia in the patient.

7. The method of claim 1 wherein at least one of the multiple electrical signals has a pulse width in a pulse width range of from about 10 microseconds to about 333 microseconds.

8. The method of claim 1 wherein at least one of the multiple electrical signals has a frequency within a frequency range of from about 40 Hz to about 500 Hz.

9. The method of claim 1 wherein the multiple electrical signals include at least a first electrical signal and a second electrical signal, and wherein the first electrical signal has a different frequency than the second electrical signal.

10. The method of claim 1 wherein the multiple electrical therapy signals are delivered to multiple target tissues in the patient's spinal cord.

11. A method for treating back or leg pain in a patient by modulating a glial neuronal cell interaction of the patient, the method comprising:
    programming a signal generator to deliver multiple electrical therapy signals to multiple target tissues located in the patient's spinal cord via one or more implanted signal delivery elements to treat the patient,
    wherein the electrical therapy signals modulate a glial neuronal cell interaction of the patient to reduce the back or leg pain in the patient.

12. The method of claim 11 wherein the multiple electrical therapy signals are delivered simultaneously.

13. The method of claim 11 wherein the one or more signal delivery elements include a lead having a plurality of electrical contacts, and wherein the multiple electrical therapy signals are delivered via different electrical contacts of the plurality of electrical contacts.

14. The method of claim 11 wherein the one or more signal delivery elements include multiple leads, and wherein the multiple electrical therapy signal are delivered via different leads.

15. The method of claim 11 wherein the multiple target tissues located in the patient's spinal cord are at a vertebral location between about T8 and T12.

16. The method of claim 11 wherein at least one of the multiple electrical signals does not create paresthesia in the patient.

17. The method of claim 11 wherein at least one of the multiple electrical signals has a pulse width in a pulse width range of from about 10 microseconds to about 333 microseconds.

18. The method of claim 11 wherein the multiple electrical signals include at least a first electrical signal and a second electrical signal, and wherein the first electrical signal has a different frequency than the second electrical signal.

19. A method for treating back or leg pain in pain in a patient by changing an activity of a glial cell of the patient, the method comprising:
    programming a signal generator to deliver multiple electrical therapy signals to multiple target tissues located in the patient's spinal cord via one or more implanted signal delivery elements to treat the patient,
    wherein the electrical therapy signals produce changes in the activity of the glial cell of the patient to reduce the back or leg pain in the patient.

20. The method of claim 19 wherein the multiple target tissues located in the patient's spinal cord are at a vertebral location between about T8 and T12.

21. The method of claim 19 wherein the multiple electrical signals each have a frequency within a frequency range of from about 2 Hz to about 100 KHz.

22. The method of claim 19 wherein at least one of the multiple electrical signals has a frequency within a frequency range of from about 40 Hz to about 500 Hz.

23. The method of claim 19 wherein the multiple electrical signals include at least a first electrical signal and a second electrical signal, and wherein the first electrical signal has a different frequency than the second electrical signal.

24. The method of claim 19 wherein at least one of the multiple electrical signals does not create paresthesia in the patient.

25. A method for treating back or leg pain in a patient by changing an expression of a glial cell of the patient, the method comprising:
    programming a signal generator to deliver multiple electrical therapy signals to multiple target tissues located in the patient's spinal cord via one or more implanted signal delivery elements to treat the patient,
    wherein the electrical therapy signals produce changes in the expression of the glial cell of the patient to reduce the back or leg pain in the patient.

26. The method of claim 25 wherein the multiple target tissues located in the patient's spinal cord are at a vertebral location between about T8 and T12.

27. The method of claim 25 wherein the multiple electrical signals each have a frequency within a frequency range of from about 2 Hz to about 100 KHz.

28. The method of claim 25 wherein at least one of the multiple electrical signals has a frequency within a frequency range of from about 40 Hz to about 500 Hz.

29. The method of claim 25 wherein the multiple electrical signals include at least a first electrical signal and a second electrical signal, and wherein the first electrical signal has a different frequency than the second electrical signal.

30. The method of claim 25 wherein at least one of the multiple electrical signals does not create paresthesia in the patient.

* * * * *